(12) United States Patent
Walsh et al.

(10) Patent No.: US 12,202,862 B2
(45) Date of Patent: Jan. 21, 2025

(54) METHODS AND COMPOSITIONS FOR THE TREATMENT OF HEPATITIS B INFECTION

(71) Applicant: MELBOURNE HEALTH, Parkville (AU)

(72) Inventors: Renae Walsh, Yackandandah (AU); Stephen Locarnini, Balaclava (AU); Hans Netter, Clayton (AU); Ronald Farquhar, Boston, MA (US)

(73) Assignee: MELBOURNE HEALTH, Parkville (AU)

( * ) Notice: Subject to any disclaimer, the term of this patent is extended or adjusted under 35 U.S.C. 154(b) by 0 days.

(21) Appl. No.: 18/452,698

(22) Filed: Aug. 21, 2023

(65) Prior Publication Data

US 2024/0150412 A1 May 9, 2024

Related U.S. Application Data

(63) Continuation of application No. 17/053,835, filed as application No. PCT/US2019/031483 on May 9, 2019, now Pat. No. 11,773,141.

(60) Provisional application No. 62/669,663, filed on May 10, 2018.

(51) Int. Cl.
| | |
|---|---|
| A61K 39/29 | (2006.01) |
| A61K 39/00 | (2006.01) |
| A61K 39/295 | (2006.01) |
| A61K 39/385 | (2006.01) |
| A61P 31/20 | (2006.01) |
| C07K 14/005 | (2006.01) |
| C12N 7/00 | (2006.01) |

(52) U.S. Cl.
CPC .......... *C07K 14/005* (2013.01); *A61K 39/292* (2013.01); *A61P 31/20* (2018.01); *C12N 7/00* (2013.01); *A61K 2039/6031* (2013.01); *C07K 2319/00* (2013.01); *C12N 2730/10122* (2013.01); *C12N 2730/10123* (2013.01); *C12N 2730/10134* (2013.01); *C12N 2730/10171* (2013.01)

(58) Field of Classification Search
CPC .... A61K 2039/5258; A61K 2039/6031; A61K 2039/64; A61K 39/12; A61K 39/292
See application file for complete search history.

(56) References Cited

U.S. PATENT DOCUMENTS

| | | |
|---|---|---|
| 4,599,231 A | 7/1986 | Milich et al. |
| 2004/0146529 A1 | 7/2004 | Selby et al. |
| 2006/0246089 A1 | 11/2006 | Wu et al. |

FOREIGN PATENT DOCUMENTS

| | | |
|---|---|---|
| CN | 106459998 A | 2/2017 |
| EP | 2 292 642 A1 | 3/2011 |
| JP | 2004-504067 A | 2/2004 |
| WO | WO-02/10416 A1 | 2/2002 |
| WO | WO-2017/060504 A1 | 4/2017 |

OTHER PUBLICATIONS

International Preliminary Report on Patentability on PCT PCT/US2019/031483 dated Nov. 19, 2020 (9 pages).
International Search Report and Written Opinion in International Patent Application No. PCT/US2019/031483 dated Oct. 24, 2019 (13 pages).
Tsutsumi et al., "Validation of Cross-Genotype Neutralization by Hepatitis B Virus-Specific Monoclonal Antibodies by In Vitro and In Vivo Infection," PLoS One 10(2): E0118062, published Feb. 18, 2015.
Walsh et al., "A novel therapeutic vaccine achieves functional cure in a mouse model of chronic hepatitis B", Journal of Hepatology, 2021, vol. 75(2), pp. S739-S740.
Walsh et al., "Impact of various expression systems on efficacy of HBsAg therapeutic vaccines to achieve clearance in a mouse model of chronic hepatitis B", Hepatology, 2021, vol. 74(1), pp. 508a-509a.
Walsh et al., "Predicting HBsAg clearance in genotype A chronic hepatitis B using HBsAg epitope profiling: A biomarker for functional cure", Liver International, 2019, vol. 39, pp. 2066-2076.

*Primary Examiner* — Barry A Chestnut
(74) *Attorney, Agent, or Firm* — FOLEY & LARDNER LLP

(57) ABSTRACT

Disclosed herein are compositions and methods for the treatment of hepatitis B infection, including chronic hepatitis B (CHB).

31 Claims, 24 Drawing Sheets

Specification includes a Sequence Listing.

Generation 2: Expansion of cure-associated epitopes in native loop1 or loop 2 context:
Construct 8 (BNP 8):
Loop region duplicated (aa 120-147)

Parent HBsAg-S template: genotype D, serotype ayw

BNP-CP: HBsAg profiles

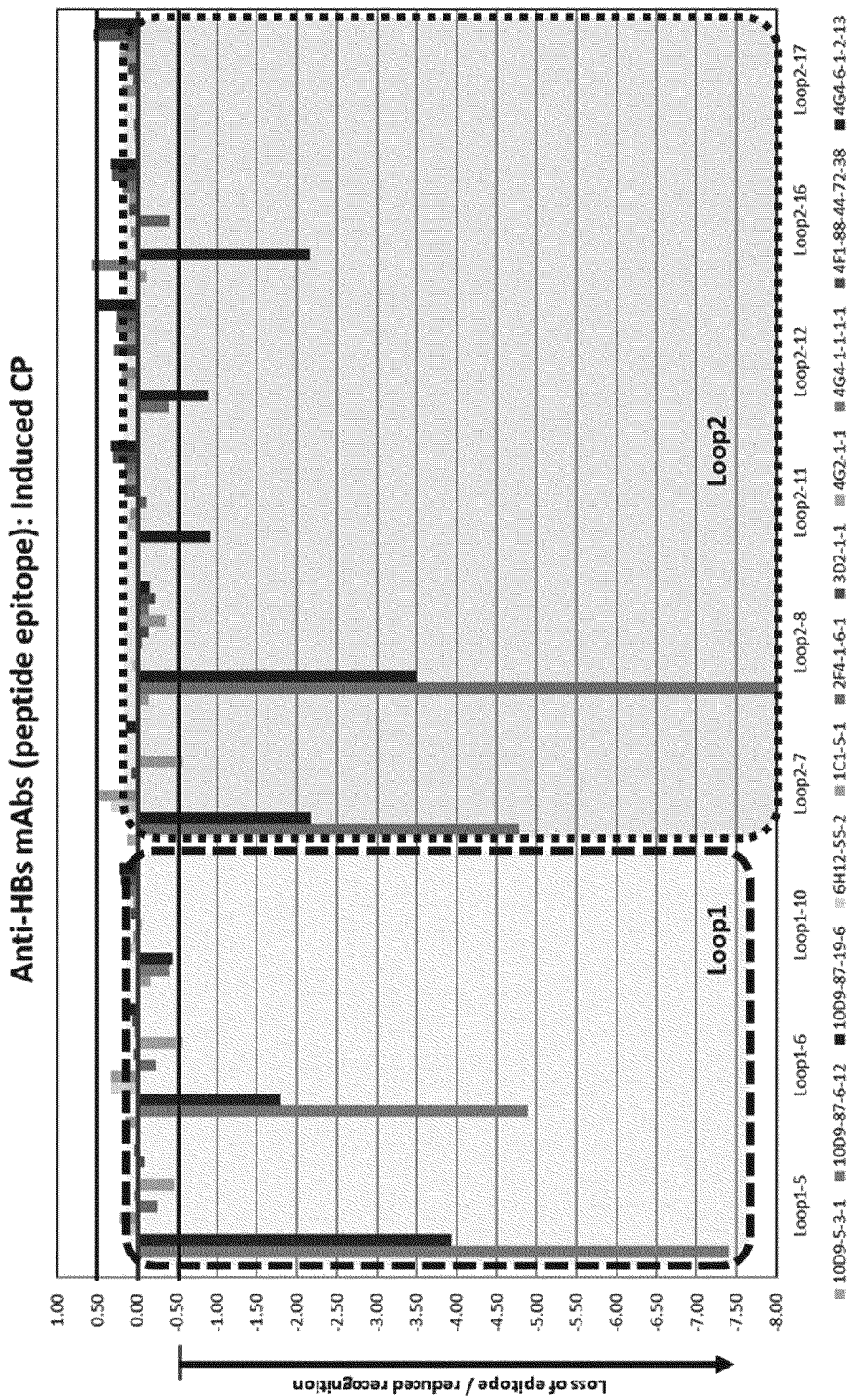

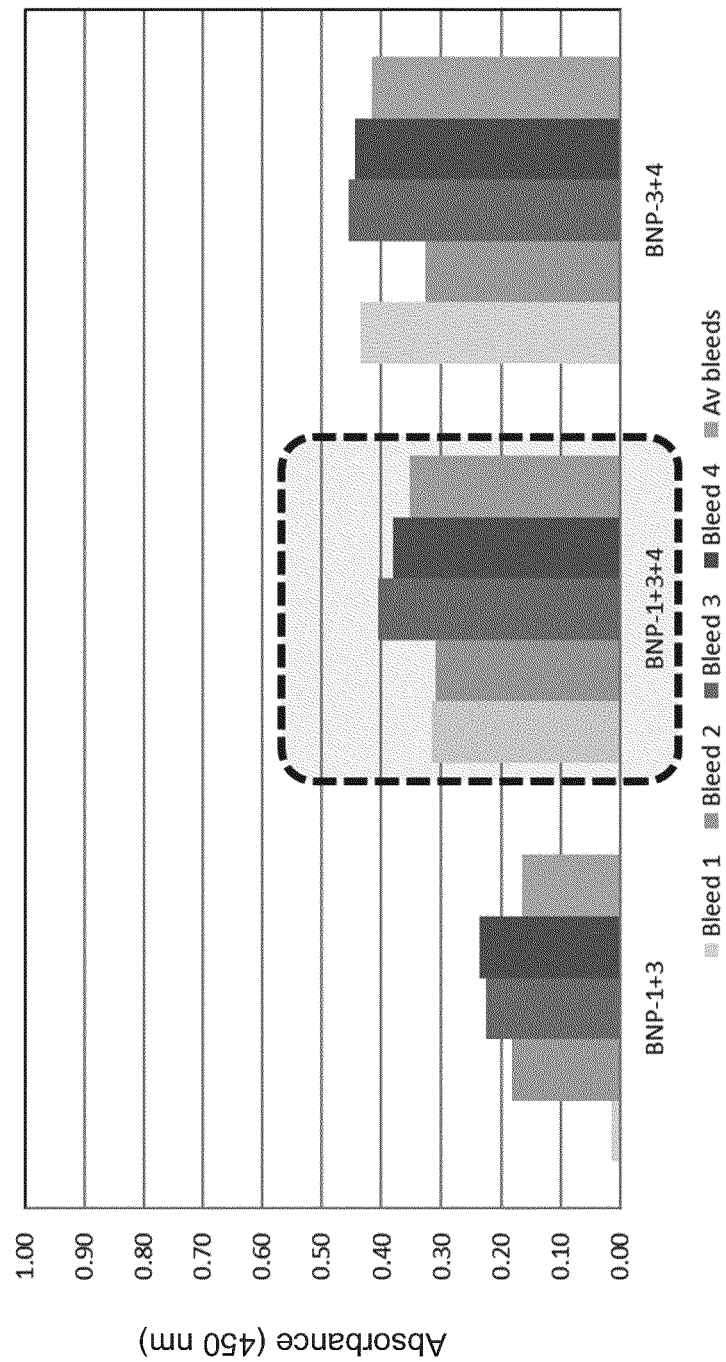

FIG. 14

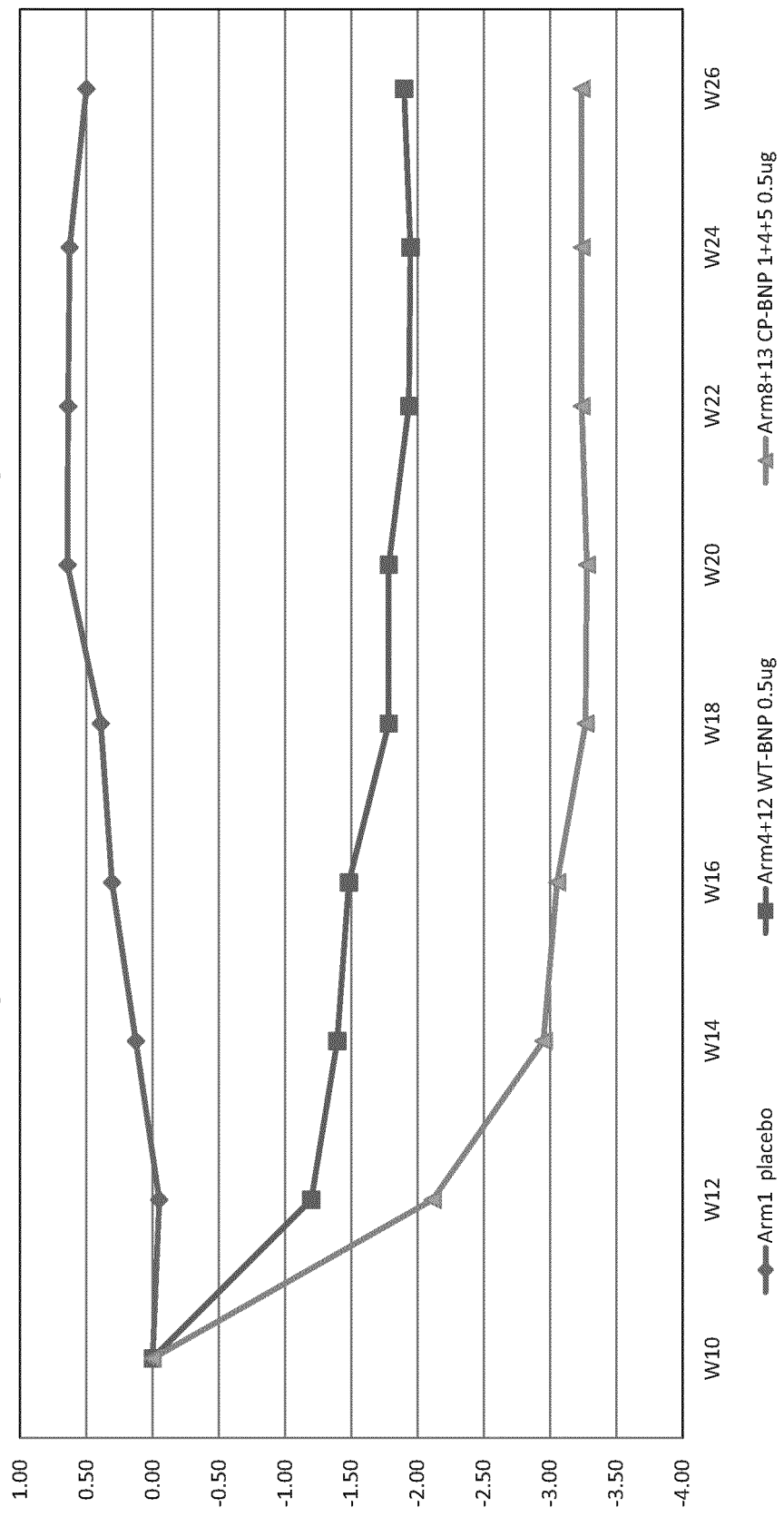

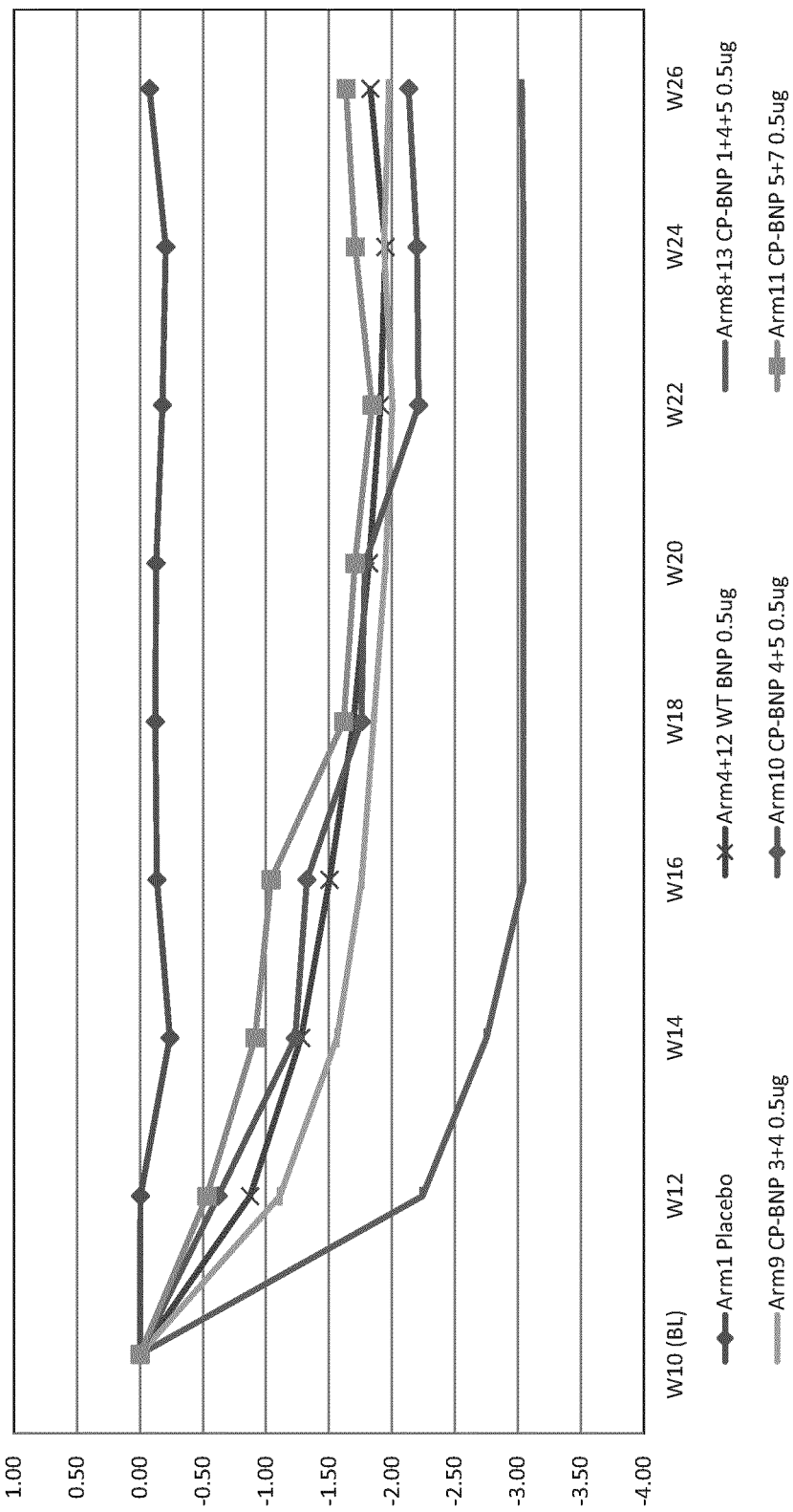

1. WT-BNP (with flag tag) purified protein, 1:400
2. WT-BNP DNA (with flag tag) transfection control, 1:100
3. Untreated control, 1:4
4. Reagent only control, 1:4
5. WT-BNP (no flag tag) mRNA transfection, neat
6. CP-BNP4 (no flag tag) mRNA transfection, neat

1. WT-BNP (with flag tag) purified protein, 1:400
2. Untreated control, neat
3. Reagent only control, neat
4. WT-BNP DNA (with flag tag) transfection control, 1:4
5. WT-BNP (no flag tag) mRNA transfection, 1:4
6. CP-BNP4 (no flag tag) mRNA transfection, neat

METHODS AND COMPOSITIONS FOR THE TREATMENT OF HEPATITIS B INFECTION

CROSS-REFERENCE TO RELATED APPLICATIONS

This application is a continuation of U.S. patent application Ser. No. 17/053,835, filed Nov. 9, 2020, now U.S. Pat. No. 11,773,141, which is a U.S. National Stage Application under 35 U.S.C. § 371 of International Patent Application No. PCT/US2019/031483, filed on May 9, 2019, which claims the benefit of and priority to U.S. Provisional Patent Application No. 62/669,663, filed May 10, 2018, the entire contents of which are incorporated herein by reference.

SEQUENCE LISTING

The instant application contains a Sequence Listing which has been submitted electronically in XML file format and is hereby incorporated by reference in its entirety. Said XML copy, created on Aug. 21, 2023, is named 117586-0122 Sequence List.XML and is 90,376 bytes in size.

FIELD OF TECHNOLOGY

The present technology relates to compositions and methods for the treatment of hepatitis B infection, including chronic hepatitis B (CHB).

BACKGROUND

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

Hepatitis B is the most common viral hepatitis, potentially life threatening, with long term complications and is one of the major public health challenges worldwide. Currently, vaccine is the most effective tool against hepatitis B infection. While the availability of a vaccine has reduced the number of new hepatitis B virus (HBV) infections, it does not benefit the 257 million people already chronically infected by the virus (WHO Fact Sheet 18 Jul. 2018). It is estimated that a cumulative 63 million new cases of chronic HBV infection and 17 million HBV-related deaths to occur between 2015 and 2030 (Nayagam et al. *Lancet Infectious Dis* 2016 16:1399-1408).

Chronic infection with hepatitis B virus (HBV) leads to the clinical outcome of liver disease, including cirrhosis and hepatocellular carcinoma (HCC). Despite the introduction of a preventative hepatitis B vaccine more than 30 years ago, chronic hepatitis B (CHB) infection remains a global health issue (Lozano R, et al. *Lancet* 2012; 380(9859):2095-128), contributing to more than 50% of the world's liver cancer burden. Approximately one-third of individuals with chronic hepatitis B (CHB) will die from serious liver diseases, such as cirrhosis, hepatocellular carcinoma (HCC), and liver failure, if left untreated. By numbers, there are estimated to be 260-350 million people living with the virus worldwide and more than 780,000 people dying each year from HBV-related liver disease including cirrhosis and liver cancer (Lozano R, et al. Lancet. 2012; 380(9859):2095-128). Current nucleos(t)ide analogue (NA) therapies for CHB effectively target viral DNA suppression (HBV DNA undetectable), but not the clearance of the HBV surface antigen (HBsAg), continued expression of which is associated with ongoing risk for developing HCC (Fattovich G, et al. *Am J Gastroenterol.* 1998;93(6):896-900; Yuen M F et al. *Gastroenterology* 2008; 135(4): 1192-1199). Hepatitis B complete cure is defined by the eradication of the virus and all its replicative intermediates (Revill P, et al. *Nature Reviews Gastroenterology and Hepatology,* 2016, 13(4):239-248), which is presently considered an unrealistic outcome. The clinical endpoint of HBsAg loss and/or seroconversion to anti-HBs is the current goal for CHB therapy, but is rarely achieved. The basis for this clearance is presumably the selective pressure of an effective host antiviral (antibody driven) response. However, the innate and adaptive immune responses in patients with CHB have been shown to be compromised, characterised by suboptimal antigen presentation, exhaustion of antigen-specific T-cells and insufficient antibody production (Wang L, et al. *World J Hepatol.* 2015, 7(30):2980-91). Accordingly, there is a need to develop additional therapeutic approaches for CHB.

At present, the preferred first-line treatment choices are pegylated-interferon alpha-2a (pegIFN-α), entecavir, and tenofovir, based on their superior antiviral efficacy and/or high resistance barrier. However, even with the first-line treatment options, pegIFN-α is effective in achieving sustained virological response in only 30% of HBeAg-positive and 40% of HBeAg-negative cases and is usually associated with severe side-effects. On the other hand, the nucleos(t)ide analogs are well tolerated and potently suppress HBV replication in the vast majority of treated patients. However, even the most potent nucleos(t)ide analogs rarely induce HBV surface antigen (HBsAg) seroconversion, the hallmark of a successful immunologic response to HBV with complete and durable control of infection, or a "functional cure." Hence, long-term, and possibly life-long, NA treatment is required to continuously suppress HBV replication, which may be associated with significant cost burden and limited by drug-associated toxicity. It is, therefore, a pressing need for the introduction of therapeutic regimens that are safer and effective in achieving a functional cure.

The infectious HBV virion is a spherical particle 42 nm in diameter consisting of an icosahedral nucleocapsid in which the viral DNA genome is packaged, and a lipoprotein envelope containing three related transmembrane proteins (HBsAg) referred to as HBsAg large (HBsAg-L), HBsAg-middle (HBsAg-M) and HBsAg-small (HBsAg-S). The synthesis of the envelope proteins is initiated at three different in-frame translation start sites. Consequently, the envelope proteins have a shared region known as the S-domain. HBsAg-S is composed only of the S-domain consisting of 226 amino acids (aa); HBsAg-M contains an additional N-terminal extensions, the 55 amino acid preS2 domain; and HBsAg-L contains the preS2 domain and an additional 108 or 119 amino acid (genotype dependent) N-terminal extensions called the preS1 domain.

The capacity of HBsAg-S to self-assemble in the presence of lipid at the endoplasmic reticulum (ER) results in the formation of secretion competent subviral particles (VLPs), which do not contain any other HBV viral component. HBsAg-S VLPs are 22-25 nanometer (nm) in diameter, highly compact, and it is estimated that one particle contains approximately one hundred HBsAg-S molecules. HBsAg-M also forms secretion competent VLPs. HBsAg-L also forms VLPs which may not be fully secretion competent.

HBsAg particle formation is an elaborate process. The first step in the particle formation is the cotranslational insertion of the protein into the ER membrane with a short luminal exposed N-terminal sequence, two transmembrane regions separated by a 57aa cytosolic loop, and a luminal external 70 aa domain containing the major B-cell epitopes ('a'-determinant). HBsAg-S VLPs represent a highly compact structure due to the large number of intra- and intermolecular disulfide bonds within and between the individual subunits.

VLPs are tools of a leading innovative bionanotechnology vector and vaccine development, and they have a number of advantages over traditional vaccines. VLPs do not contain viral genetic material and represent high-density displays of viral structural proteins that efficiently trigger key parts of the immune system for B cell and/or T cell responses (Buonaguro L. et al., (2011), *Expert Rev Vaccines* 10:1569-1583; Jennings G T and Bachmann M F. (2009) *Annu Rev Pharmacol Toxicol.* 2009, 49:303-326; Pushko P, et al., *Intervirology* 2013, 56:141-165).

Chimeric VLPs based on the capsid proteins of e.g., HBV, human papilloma virus (HPV), as well as Qβ phage have been engineered to express foreign antigenic sequences including non-pathogen associated antigens such as nicotine and angiotensin II for smoking cessation and to overcome hypertension, respectively (Ambühl PM et al. *J. Hypertension.* 2007, 25:63-72; Buonaguro L. et al. *Exp. Rev. Vaccines* 2011, 10:1569-1583; Cornuz J. et al. *PlosOne* 2008, 3:e2547). In contrast to capsid VLPs, which are composed of protein subunits only, HBV based HBsAg-S VLPs are composed of envelope proteins and lipid, the ER being the cellular location for assembly. For the presentation of antigenic sequences to the immune system, HBsAg-S VLPs have been modified to carry foreign epitopes (Delpeyroux F. et al. *Science* 1986, 233:472-475; Eckhart L., et al. *J. Gen. Virology* 1996, 77:2001-2008; Fomsgaard A. et al. *Scand. J. Immunol.* 1998, 47:289-295; Phogat S. et al. *Virology* 2008, 373:72-84; Netter H J et al. *J. Virology* 2001, 75:2130-2141). VLPs composed of HBsAg-L were developed as a delivery system for genes and drugs to human hepatocytes (Yamada T et al. *Nature Biotechnology* 2003, 21:885-890). Duck hepatitis B virus envelope proteins and other hepadnaviral envelope proteins have been modified to express antigens of interest as part of VLPs.

VLPs composed of the small envelope proteins (HBsAg-S) derived from HBV are the antigenic components of a successful protective vaccine (Jilg W et al. *Lancet ii* 1984, 1174-1175; Zuckerman J N. *J Med Virology* 2006, 78:169-177). Nevertheless, even with the availability of a vaccine, hepatitis B still represents an enormous health problem.

A significant issue in vaccine development is the diminished capacity of an aged immune system and immunosenescence being associated with a decreased vaccine efficacy in the elderly (Derhovanessian E and Pawelec G. *Microbial Biotechnology* 2012, 5:226-232; Pera A et al. *Maturitas* 2015, 82: 50-55).

The endpoint of HBsAg loss in the absence or presence of seroconversion to anti-HBs in combination with undetectable level of HBV DNA in the serum is the current goal for CHB therapy, but is rarely achieved. The basis for this clearance is presumably the selective pressure of an effective host antiviral (antibody driven) response. However, the innate and adaptive immune responses in patients with CHB have been shown to be compromised, characterised by suboptimal antigen presentation, exhaustion of antigen-specific T-cells and insufficient antibody production (Wang L, et al. *World J Hepatology* 2015, 7(30):2980-2991).

There is a need to develop an effective B-cell vaccine for the treatment of CHB. In particular, there is a need to develop a therapeutic protocol which enables a functional cure to be achieved.

SUMMARY

In one aspect, the present disclosure provides a recombinant virus-like particle antigen (VLP-Ag) comprising a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or wherein the one or more antigenic epitope repeat regions is defined by the amino acid sequence $PCX_8TCX_9X_{10}X_{11}$ (SEQ ID NO: 25) wherein $X_8$ is K or R, $X_9$ is T or M, $X_{10}$ is T, I or S, and $X_{11}$ is P, T or L.

In some embodiments, the one or more antigenic epitope repeat regions expressed in Loop 2 is defined by the consensus amino acid sequence $CCCTKPX_{12}DGNCX_{13}$ (SEQ ID NO: 26), wherein $X_{12}$ is T or S; and $X_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFPSCCCTKPTDGNC (SEQ ID NO: 40).

In some embodiments, the hepadnaviral envelope fusion protein comprises a spacer domain between the antigenic epitope repeat regions and the envelope protein.

In one aspect, the present disclosure provides a nucleic acid encoding a VLP-Ag of the present technology. In one aspect, the present disclosure provides an expression vector comprising the nucleic acid.

In one aspect, the present disclosure provides a composition comprising a VLP-Ag of the present technology and a pharmaceutically acceptable carrier.

In one aspect, the present disclosure provides a method of treating hepatitis B infection in a subject in need thereof, comprising administering to the subject a recombinant VLP-Ag comprising a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or wherein the one or more antigenic epitope repeat regions is defined by the amino acid sequence $PCX_8TCX_9X_{10}X_{11}$ (SEQ ID NO: 25) wherein $X_8$ is K or R, $X_9$ is T or M, $X_{10}$ is T, I or S, and $X_{11}$ is P, T or L.

In some embodiments, the one or more antigenic epitope repeat regions expressed in Loop 2 is defined by the consensus amino acid sequence CCCTKPX$_{12}$DGNCX$_{13}$ (SEQ ID NO: 26), wherein X$_{12}$ is T or S; and X$_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the hepadnaviral envelope fusion protein comprises a spacer domain between the antigenic epitope repeat regions and the envelope protein.

In one aspect, the present disclosure provides the use of a recombinant VLP-Ag in the manufacture of a medicament for treating hepatitis B infection in a subject in need thereof, wherein the VLP-Ag comprises a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence CX$_1$TCX$_2$X$_3$X$_4$X$_5$QGX$_6$SMX$_7$PC (SEQ ID NO: 24), wherein X$_1$ is K or R, X$_2$ is T or M, X$_3$ is T or I, X$_4$ is P T or L, X$_5$ is A or V, X$_6$ is N or T, and X$_7$ is F or Y; or wherein the one or more antigenic epitope repeat regions is defined by the amino acid sequence PCX$_8$TCX$_9$X$_{10}$X$_{11}$ (SEQ ID NO: 25) wherein X$_8$ is K or R, X$_9$ is T or M, X$_{10}$ is T, I or S, and X$_{11}$ is P, T or L.

In some embodiments, the one or more antigenic epitope repeat regions expressed in Loop 2 is defined by the consensus amino acid sequence CCCTKPX$_{12}$DGNCX$_{13}$ (SEQ ID NO: 26), wherein X$_{12}$ is T or S; and X$_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the hepadnaviral envelope fusion protein comprises a spacer domain between the antigenic epitope repeat regions and the envelope protein.

In one aspect, the present disclosure provides a method for inducing an immune response against hepatitis B virus in a subject comprising administering to the subject a recombinant VLP-Ag comprising a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence CX$_1$TCX$_2$X$_3$X$_4$X$_5$QGX$_6$SMX$_7$PC (SEQ ID NO: 24), wherein X$_1$ is K or R, X$_2$ is T or M, X$_3$ is T or I, X$_4$ is P T or L, X$_5$ is A or V, X$_6$ is N or T, and X$_7$ is F or Y; or wherein the one or more antigenic epitope repeat regions is defined by the amino acid sequence PCX$_8$TCX$_9$X$_{10}$X$_{11}$ (SEQ ID NO: 25) wherein X$_8$ is K or R, X$_9$ is T or M, X$_{10}$ is T, I or S, and X$_{11}$ is P, T or L.

In some embodiments, the one or more antigenic epitope repeat regions expressed in Loop 2 is defined by the consensus amino acid sequence CCCTKPX$_{12}$DGNCX$_{13}$ (SEQ ID NO: 26), wherein X$_{12}$ is T or S; and X$_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the hepadnaviral envelope fusion protein comprises a spacer domain between the antigenic epitope repeat regions and the envelope protein.

In one aspect, the present disclosure provides the use of a recombinant VLP-Ag in the manufacture of a composition for inducing an immune response against hepatitis B, wherein the VLP-Ag comprises a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence CX$_1$TCX$_2$X$_3$X$_4$X$_5$QGX$_6$SMX$_7$PC (SEQ ID NO: 24), wherein X$_1$ is K or R, X$_2$ is T or M, X$_3$ is T or I, X$_4$ is P T or L, X$_5$ is A or V, X$_6$ is N or T, and X$_7$ is F or Y; or wherein the one or more antigenic epitope repeat regions is defined by the amino acid sequence PCX$_8$TCX$_9$X$_{10}$X$_{11}$ (SEQ ID NO: 25) wherein X$_8$ is K or R, X$_9$ is T or M, X$_{10}$ is T, I or S, and X$_{11}$ is P, T or L.

In some embodiments, the one or more antigenic epitope repeat regions expressed in Loop 2 is defined by the consensus amino acid sequence CCCTKPX$_{12}$DGNCX$_{13}$ (SEQ ID NO: 26), wherein X$_{12}$ is T or S; and X$_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the hepadnaviral envelope fusion protein comprises a spacer domain between the antigenic epitope repeat regions and the envelope protein.

In one aspect, the present disclosure provides a kit for treating hepatitis B infection in a subject in need thereof comprising a recombinant VLP-Ag, wherein the VLP-Ag comprises a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence CX$_1$TCX$_2$X$_3$X$_4$X$_5$QGX$_6$SMX$_7$PC (SEQ ID NO: 24), wherein X$_1$ is K or R, X$_2$ is T or M, X$_3$ is T or I, X$_4$ is P T or L, X$_5$ is A or V, X$_6$ is N or T, and X$_7$ is F or Y;

or wherein the one or more antigenic epitope repeat regions is defined by the amino acid sequence PCX$_8$TCX$_9$X$_{10}$X$_{11}$ (SEQ ID NO: 25) wherein X$_8$ is K or R, X$_9$ is T or M, X$_{10}$ is T, I or S, and X$_{11}$ is P, T or L.

In some embodiments, the one or more antigenic epitope repeat regions expressed in Loop 2 is defined by the consensus amino acid sequence CCCTKPX$_{12}$DGNCX$_{13}$ (SEQ ID NO: 26), wherein X$_{12}$ is T or S; and X$_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the hepadnaviral envelope fusion protein comprises a spacer domain between the antigenic epitope repeat regions and the envelope protein.

In one aspect, the present disclosure provides a recombinant mRNA encoding a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence CX$_1$TCX$_2$X$_3$X$_4$X$_5$QGX$_6$SMX$_7$PC (SEQ ID NO: 24), wherein X$_1$ is K or R, X$_2$ is T or M, X$_3$ is T or I, X$_4$ is P T or L, X$_5$ is A or V, X$_6$ is N or T, and X$_7$ is F or Y; or wherein the one or more antigenic epitope repeat regions is defined by the amino acid sequence PCX$_8$TCX$_9$X$_{10}$X$_{11}$ (SEQ ID NO: 25) wherein X$_8$ is K or R, X$_9$ is T or M, X$_{10}$ is T, I or S, and X$_{11}$ is P, T or L.

In some embodiments, the one or more antigenic epitope repeat regions expressed in Loop 2 is defined by the consensus amino acid sequence CCCTKPX$_{12}$DGNCX$_{13}$ (SEQ ID NO: 26), wherein X$_{12}$ is T or S; and X$_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the modified hepadnaviral envelope fusion protein comprises a spacer domain between the antigenic epitope repeat regions and the envelope protein.

In one aspect, the present disclosure provides an expression vector comprising a recombinant mRNA of the present technology. In one aspect, the present disclosure provides a composition comprising the recombinant mRNA of and a pharmaceutically acceptable carrier.

In one aspect, the present disclosure provides a method of treating hepatitis B infection in a subject in need thereof, comprising administering to the subject a recombinant mRNA encoding a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence CX$_1$TCX$_2$X$_3$X$_4$X$_5$QGX$_6$SMX$_7$PC (SEQ ID NO: 24), wherein X$_1$ is K or R, X$_2$ is T or M, X$_3$ is T or I, X$_4$ is P T or L, X$_5$ is A or V, X$_6$ is N or T, and X$_7$ is F or Y; or wherein the one or more antigenic epitope repeat regions is defined by the amino acid sequence PCX$_8$TCX$_9$X$_{10}$X$_{11}$ (SEQ ID NO: 25) wherein X$_8$ is K or R, X$_9$ is T or M, X$_{10}$ is T, I or S, and X$_{11}$ is P, T or L.

In some embodiments, the one or more antigenic epitope repeat regions expressed in Loop 2 is defined by the consensus amino acid sequence CCCTKPX$_{12}$DGNCX$_{13}$ (SEQ ID NO: 26), wherein X$_{12}$ is T or S; and X$_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the hepadnaviral envelope fusion protein comprises a spacer domain between the antigenic epitope repeat regions and the envelope protein.

In one aspect, the present disclosure provides a method for inducing an immune response against hepatitis B virus in a subject comprising administering to the subject a recombinant mRNA encoding modified hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or wherein the one or more antigenic epitope repeat regions is defined by the amino acid sequence $PCX_8TCX_9X_{10}X_{11}$ (SEQ ID NO: 25) wherein $X_8$ is K or R, $X_9$ is T or M, $X_{10}$ is T, I or S, and $X_{11}$ is P, T or L.

In some embodiments, the one or more antigenic epitope repeat regions expressed in Loop 2 is defined by the consensus amino acid sequence $CCCTKPX_{12}DGNCX_{13}$ (SEQ ID NO: 26), wherein $X_{12}$ is T or S; and $X_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the modified hepadnaviral envelope fusion protein comprises a spacer domain between the antigenic epitope repeat regions and the envelope protein.

In one aspect, the present disclosure provides the use of a recombinant mRNA in the manufacture of a composition for inducing an immune response against hepatitis B, wherein the recombinant mRNA encodes a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or wherein the one or more antigenic epitope repeat regions is defined by the amino acid sequence $PCX_8TCX_9X_{10}X_{11}$ (SEQ ID NO: 25) wherein $X_8$ is K or R, $X_9$ is T or M, $X_{10}$ is T, I or S, and $X_{11}$ is P, T or L.

In some embodiments, the one or more antigenic epitope repeat regions expressed in Loop 2 is defined by the consensus amino acid sequence $CCCTKPX_{12}DGNCX_{13}$ (SEQ ID NO: 26), wherein $X_{12}$ is T or S; and $X_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the modified hepadnaviral envelope fusion protein comprises a spacer domain between the antigenic epitope repeat regions and the envelope protein.

In one aspect, the present disclosure provides a kit for treating hepatitis B infection in a subject in need thereof comprising a recombinant mRNA, wherein the recombinant mRNA encodes a hepadnaviral envelope HBsAg-S fusion protein comprising one or more antigenic epitope repeat regions, wherein said antigenic epitope repeat regions are selected from the group consisting of antigenic epitopes expressed in the Loop 1 and Loop 2 regions of HBsAg-S domain.

In some embodiments, the one or more antigenic epitope repeat regions expressed in Loop 1 is defined by the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or wherein the one or more antigenic epitope repeat regions is defined by the amino acid sequence $PCX_8TCX_9X_{10}X_{11}$ (SEQ ID NO: 25) wherein $X_8$ is K or R, $X_9$ is T or M, $X_{10}$ is T, I or S, and $X_{11}$ is P, T or L.

In some embodiments, the one or more antigenic epitope repeat regions expressed in Loop 2 is defined by the consensus amino acid sequence $CCCTKPX_{12}DGNCX_{13}$ (SEQ ID NO: 26), wherein $X_{12}$ is T or S; and $X_{13}$ is T or S.

In some embodiments, the one or more antigenic epitope repeat regions is selected from the group consisting of PCKTCTTP (SEQ ID NO: 28), PCRTCTTP (SEQ ID NO: 33), CTKPTDGNC (SEQ ID NO: 34), CKTCTT-PAQGNSMFPS (SEQ ID NO: 35), CTKP(T/S)TDGNC (SEQ ID NO: 36), PC(K/R)TC(T/M)TP (SEQ ID NO:37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), and PCKTCTTPAQGNSMFP-SCCCTKPTDGNC (SEQ ID NO: 40).

In some embodiments, the modified hepadnaviral envelope fusion protein comprises a spacer domain between the antigenic epitope repeat regions and the envelope protein.

In one aspect, the present disclosure provides a composition comprising one or more peptides selected from the group consisting of TCTTPAQGNSMFPSC (SEQ ID NO: 17), TCTIPAQGTSMFPSC (SEQ ID NO: 18), TCTT-PAQGTSMFPSC (SEQ ID NO: 19), CTKPTDGNCT (SEQ ID NO: 20), and CTKPSDGNCT (SEQ ID NO: 21).

In some embodiments, wherein the one or more peptides is conjugated to a carrier protein. In some embodiments, the carrier protein is keyhole limpet hemocyanin (KLH). In some embodiments, the one or more peptides is cyclic. In some embodiments, the composition further comprises a pharmaceutically acceptable carrier.

In one aspect, the present disclosure provides a method of treating hepatitis B infection in a subject in need thereof, comprising administering to the subject one or more peptides selected from the group consisting of TCTT-PAQGNSMFPSC (SEQ ID NO: 17), TCTIPAQGTSMFPSC (SEQ ID NO: 18), TCTTPAQGTSMFPSC (SEQ ID NO: 19), CTKPTDGNCT (SEQ ID NO: 20), and CTKPSDGNCT (SEQ ID NO: 21).

In some embodiments, the one or more peptides is conjugated to a carrier protein. In some embodiments, the carrier protein is keyhole limpet hemocyanin (KLH). In some embodiments, the one or more peptides is cyclic.

BRIEF DESCRIPTION OF THE DRAWINGS

Figure 5:
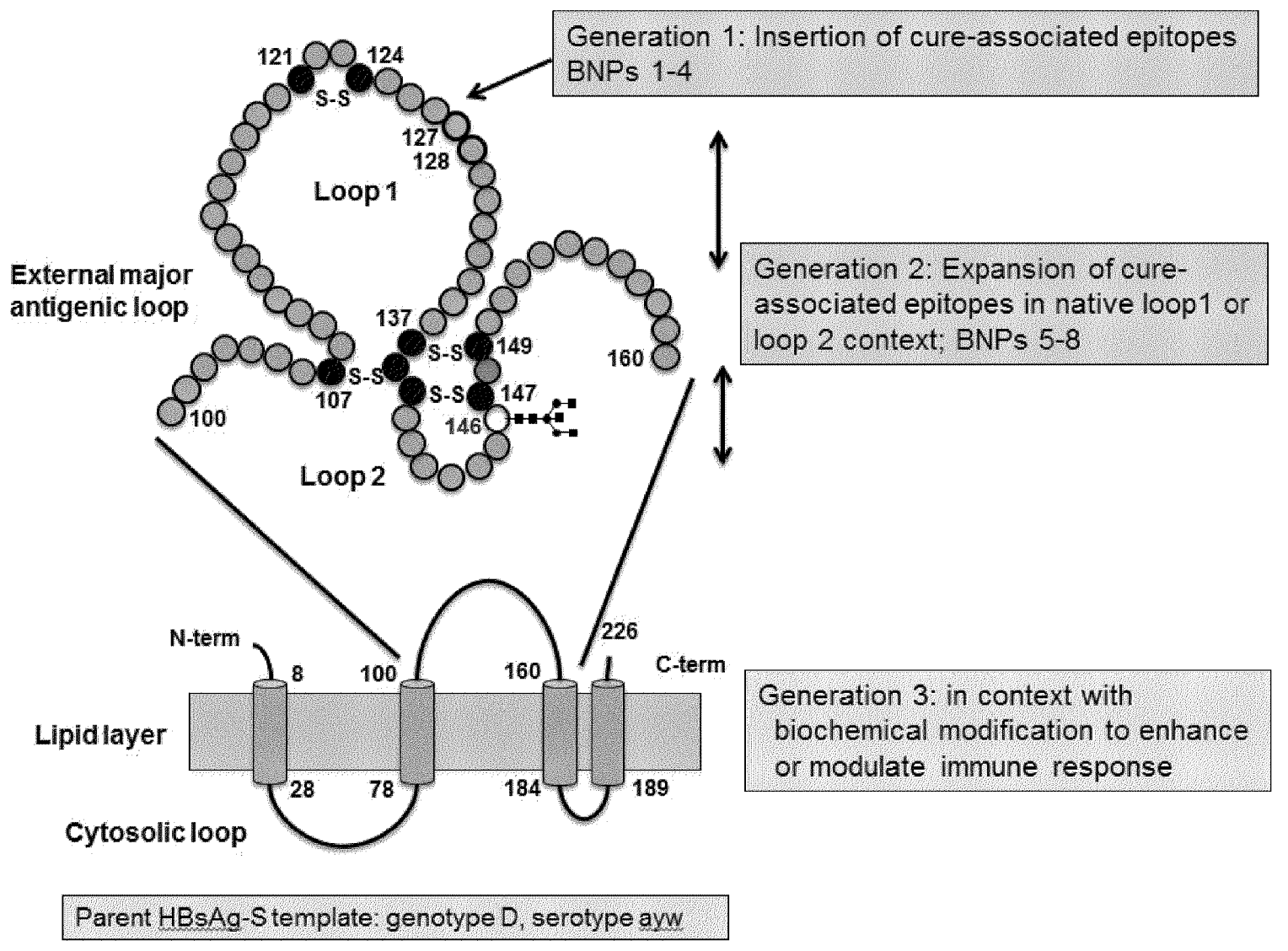

FIG. 5 is a schematic showing an overview of the proposed structure of the small hepatitis B surface (envelope) antigen (HBsAg-S), 226 amino acids in length and subtype ayw (genotype D). The external antigenic loop region between amino acids 100 and 160 of HBsAg-S is enlarged: each amino acid is represented by a grey circle, the cysteine residues are shown as black circles, the potential —S—S— disulfide bonds highlighted. The glycosylation site (asparagine) at position 146 is shown in white, and the glycan structure is indicated. The position used to insert foreign sequence is located at amino acid 127 and 128.

FIG. 10 is a schematic showing proposed folding of the HBsAg-S protein, 226 amino acids in length, for BNP 8. The external antigenic loop region between amino acids 100 and 160 of HBsAg-S is enlarged: each amino acid is represented by a grey circle, the cysteine residues are shown as black circles, the potential —S—S— disulfide bonds highlighted, the "GSGS" linker (SEQ ID NO: 53) is represented by striped circles. The glycosylation site (asparagine) at position 146 is shown in white, and the glycan structure indicated. The loop 1 and loop 2 regions were duplicated. The original amino acid positions for the wild type HBsAg-S sequence are unchanged, and the additional amino acids of the repeated loop 1 and loop 2 are marked with '. BNP-8 contains the original loop 1 and loop 2 region ('ayw', amino acid (aa) 120-147) followed by an additional loop 1 and loop 2 'adw' sequence (aa 120-147).

FIG. 12 is a chart showing a generated derived and purified monoclonal antibody analysis for the cyclic peptides. The chart shows the anti-HBs antibody induced CP profile (bioplex platform) analysis of selected generated monoclonal antibodies following immunization with loop 1 or loop 2 pan-genotypic/serotypic cyclised peptide formulations. The generated monoclonal anti-HBs antibodies n=8 were analysed for induction of an IndCP (e.g., loss of epitope recognition at both loop 1 and loop 2 epitopes) upon pre-incubation with reference VLP antigen, indicative of "clearing" or CP-associated anti-HBs profile.

FIGS. 13A-13D are charts showing the anti-HBs antibody reactivity analysis following CP-BNP antigen immunization. Standard enzyme immunoassay (EIA) analysis of sera was performed on animal bleeds (bleeds 1-4, or averaged across all bleeds) following n=3 immunizations with CP-BNP 1, 2, 3, and 4 preparations of CP-BNP 1+3, 1+3+4, and 3+4 formulations. The induced antibody response was analysed for specificity to: recombinant WT HBsAg (VLP) (FIG. 13A); HBsAg loop 1 specific cyclised peptides (FIG. 13B); and HBsAg loop 2 specific cyclised peptides (FIG. 13C). FIG. 13D reports the anti-Hbs reactivity for WT-BNP, loop1 peptide and loop2 peptide antigens. The strongest, most rapid and broadest or most conserved (to VLP and both loop 1 and loop 2 peptides) anti-HBs antibody immunogenicity responses were observed for CP-BNP formulation 1+3+4, 1+4+5, 5+7 and 5 which delivered target "clearing" epitopes for both loop 1 and loop 2 (encircled).

FIG. 14 is a chart showing the anti-HBs antibody induced CP profile (bioplex platform) analysis of selected sera responses following immunisation with single or combinations of CP-BNPs 1, 3, 4, 5, and 7 preparations. The terminal bleed sera following n=3 immunization schedule with the CP-BNP preparations and formulations were analyzed for anti-HBs antibody profile. The HBsAg epitope profile of reference VLP antigen +/− pre-incubation with anti-HBs positive individual mouse sera from the immunogenicity study was assessed for the induction of a CP due to "clearing" or CP-associated anti-HBs in the sera. This targeted "clearing" epitope anti-HBs development was most consistently observed in mice (9-5, 13-2, 16-5 and 17-3) that received CP-BNP 1+4+5, 1+3+4, 5, or 5+7 formulation immunization.

FIGS. 15A-15C are charts showing change in HBV DNA (log 10 IU/mL) levels from baseline (W10) after therapeutic vaccination of various CP-BNP combinations in a murine model of CHB infection. CP-BNP 1+4+5 at 0.5 µg dose had the most rapid and absolute sustained decline in HBV DNA relative to either placebo or WT-BNP at the same dose. Other combinations of CP-BNPs also declined in HBV DNA levels, but did so at a slower rate and less absolute decline compared to CP-BNP 1+4+5.

FIGS. 16A-16C are charts showing change in HBsAg (log 10 IU/mL) levels from baseline (W10) after therapeutic vaccination of various CP-BNP combinations in a murine model of CHB infection. CP-BNP 1+4+5 at 0.5 µg dose had the most rapid and absolute sustained decline in HBsAg relative to either placebo or WT-BNP at the same dose. Other combinations of CP-BNPs also declined in HBsAg levels, but did so at a slower rate and less absolute decline compared to CP-BNP 1+4+5.

DETAILED DESCRIPTION

Figure 1:
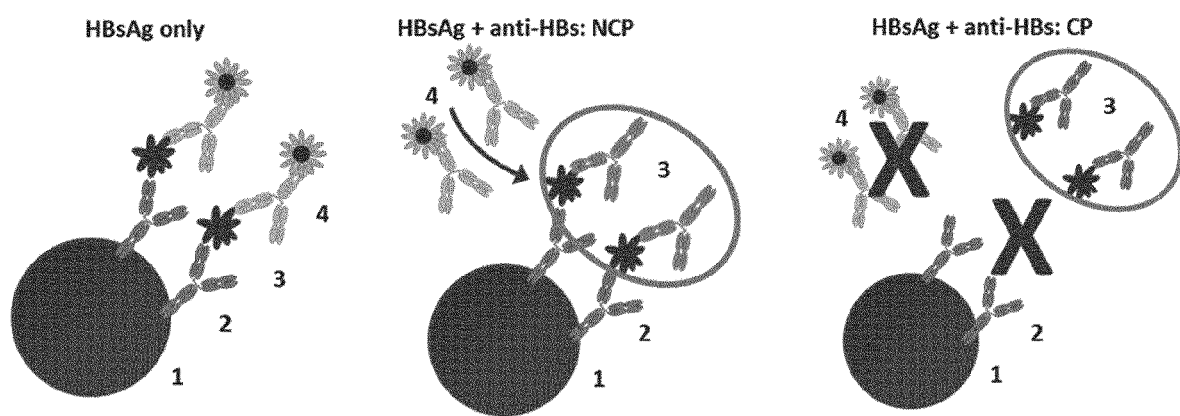
FIG. 1 is a diagrammatic representation showing HBsAg epitope occupancy assay. 1. Magnetic bead; 2. Capture Ab: mouse anti-HBs monoclonal Abs (mAbs) to HBsAg external region; 3. Reference HBsAg sample. Ag only vs Ag bound with anti-HBs sample; 4. Reporter Ab: PE conjugated polyclonal anti-HBs. NCP: non-clearance profile; CP: clearance profile.

It is to be appreciated that certain aspects, modes, embodiments, variations, and features of the present technology are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this present technology belongs.

I. General

Functional hepatitis B cure is defined as HBsAg loss with or without seroconversion to anti-HBsAg antibodies ("anti-HBS") whilst maintaining serum HBV DNA undetectability (Revill P, et al. *Nature Reviews Gastroenterology and Hepatology.* 2016, 13(4):239-248)). Described herein are HBsAg bio-nanoparticles (BNPs) incorporating enhanced antigenic display of clearance profile (CP)-associated epitopes to mimic the selective pressure of a CP and promote efficient and specific B cell anti-HBS immune responses for HBsAg clearance. The immunogenicity of BNPs is initially validated in normal BALB/c mice, prior to evaluation of therapeutic vaccination outcomes to drive HBsAg clearance and seroconversion in a newly developed and validated CBA Carter J (CBA/CaJ) murine model of CHB (see, e.g., Chen H H, et al. *PNAS* 112(7):2175-2180 (2015)). In some embodiments, the aim of a CP-expressing BNP therapeutic vaccine, when delivered to patients with CHB, is to accelerate and drive functional hepatitis B cure. In some embodiments, the therapeutic function of CP-expressing BNPs can be further enhanced by hyperglycosylation modification to enhance and accelerate B cell responses and promote HBsAg seroconversion, and/or modification of the BNP delivery backbone to induce "stealth" status of the BNPs to potentially pre-existing, neutralising, but not clearing, circulating anti-HBs antibodies in CHB patients.

II. Definitions

The following terms are used herein, the definitions of which are provided for guidance.

As used in the subject specification, the singular forms "a", "an" and "the" include plural aspects unless the context clearly dictates otherwise. Thus, for example, reference to "a profile" includes a single profile, as well as two or more profiles; reference to "an epitope" includes a single epitope, as well as two or more epitopes, "an antibody" includes a single antibody, as well as two or more antibodies; reference to "the disclosure" includes a single and multiple aspects taught by the disclosure; and so forth.

The term "about" and the use of ranges in general, whether or not qualified by the term about, means that the number comprehended is not limited to the exact number set forth herein, and is intended to refer to ranges substantially within the quoted range while not departing from the scope of the technology. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "antigen" is used herein in its broadest sense to refer to a substance that is capable of reacting in and/or inducing an immune response. Reference to an "antigen" includes an antigenic determinant or epitope.

By "antigenic determinant" or "epitope" is meant that part of an antigenic molecule against which a particular immune response is directed and includes a hapten. Typically, in an animal, antigens present several or even many antigenic determinants simultaneously. A "hapten" is a substance that can combine specificity with an antibody but cannot or only poorly induces an immune response unless bound to a carrier. A hapten typically comprises a single antigenic determinant or epitope.

As used herein, the term "bio-nanoparticle" or "BNP" refers to a virus-like particle (VLP) that has been modified to include or display one or more target insert epitopes. For the purposes of this disclosure the terms "bio-nanoparticle" or "BNP" also refer to "recombinant virus-like particle antigen" or "VLP-Ag."

As used herein, the terms "effective amount" or "therapeutically effective amount" or "pharmaceutically effective amount" refer to a quantity sufficient to achieve a desired biological, therapeutic, and/or prophylactic effect, e.g., an amount which results in the prevention of a disease, condition and/or symptom(s) thereof. In the context of therapeutic or prophylactic applications, the amount of a composition administered to the subject will depend on the type and severity of the disease and on the characteristics of the individual, such as general health, age, sex, body weight and tolerance to the composition drugs. It will also depend on the degree, severity and type of disease or condition. The skilled artisan will be able to determine appropriate dosages depending on these and other factors. In some embodiments, multiple doses are administered. Additionally or alternatively, in some embodiments, multiple therapeutic compositions or compounds (e.g., immunogenic compositions, such as vaccines) are administered.

As used herein, the term "functional cure" refers to a functional cure of CHB and is defined by loss of detectable HBsAg with or without presence of naturally occurring or introduced anti-HBsAg antibodies (also referred to herein as "anti-HBS antibodies" or "anti-HBS"), which include a population of antibodies that selectively bind to select epitopes on HBsAg, which when occupied by anti-HBs antibodies, results in clearance of HBsAg and ultimately HBV. HBV is non-detectable in a fully cured subject.

The term "immunogenic composition" is used herein to refer to a composition that will elicit an immune response in a mammal that has been exposed to the composition. In some embodiments, an immunogenic composition includes at least one of eight CP-BNPs (e.g., BNP 1, 2, 3, 4, 5, 6, 7, 8) and/or CP epitope cyclic peptides.

In some embodiments, the immunogenic compositions described herein may be formulated for administration in a number of forms. For example, in some embodiments, the immunogenic compositions are prepared for intravenous, intramuscular, subcutaneous, parenteral, oral, nasal, or topical administration. Compositions may also be formulated for specific dosage forms. For example, in some embodiments, the immunogenic composition may be formulated as a liquid, gel, aerosol, ointment, cream, lyophilized formulation, powder, cake, tablet, or capsule. In other embodiments, the immunogenic composition is formulated as a controlled release formulation, delayed release formulation, extended release formulation, pulsatile release formulation, and mixed immediate release formulation. In some embodiments, the immunogenic composition is provided as a liquid. In other embodiments, the immunogenic composition is provided in lyophilized form.

As used herein, the term "infected" refers to harboring a disease or pathogen, such as a virus. An infection can be intentional, such as by administration of a virus or pathogen (e.g., by vaccination), or unintentional, such as by natural transfer of the pathogen from one organism to another, or from a contaminated surface to the organism. In some embodiments, infection is induced in a model organism (e.g., murine model) by in vivo transfection of replication-competent DNA using a hydrodynamic injection approach.

As used herein "subject" and "patient" are used interchangeably and refer to an animal, for example, a member of any vertebrate species. In some embodiments, the subject is a human.

As used herein, the terms "treating" or "treatment" or "alleviation" refers to therapeutic treatment, wherein the object is to reduce, alleviate, or slow down the progression or advancement of, and/or reverse the progression of the targeted pathological condition or disorder. For example, a subject is successfully "treated" for an existing and/or persisting hepatitis B infection, including chronic hepatitis B (CHB) infection if, after receiving a therapeutic amount of the compositions of the present technology, according to the methods described herein, the subject shows observable and/or measurable induction of antibodies that clear HBsAg, and/or loss of detectable HBsAg, and/or reduced levels of HBsAg and/or HBV DNA.

The term "vaccine" is used herein to refer to a composition that is administered to a subject to produce or increase immunity to a particular disease. In some embodiments, vaccines include a pharmaceutically acceptable adjuvant and/or a pharmaceutically acceptable carrier.

As used herein, "BNP 1" or "CP-BNP 1" refers to SEQ ID NO: 1, nucleotide sequences encoding the amino acid sequence set forth in SEQ ID NO 1, such as the nucleotide sequence set forth in SEQ ID NO: 9, virus-like particles (VLPs) or bio-nanoparticles (BNPs) comprising SEQ ID NO: 1, immunogenic compositions comprising SEQ ID NO: 1, or a vaccine comprising SEQ ID NO: 1.

As used herein, "BNP 2" or "CP-BNP 2" refers to SEQ ID NO: 2, nucleotide sequences encoding the amino acid sequence set forth in SEQ ID NO: 2, such as the nucleotide sequence set forth in SEQ ID NO: 10, VLPs or BNPs comprising SEQ ID NO: 2, immunogenic compositions comprising SEQ ID NO: 2, or a vaccine comprising SEQ ID NO: 2.

As used herein, "BNP 3" or "CP-BNP 3" refers to SEQ ID NO: 3, nucleotide sequences encoding the amino acid sequence set forth in SEQ ID NO: 3, such as the nucleotide sequence set forth in SEQ ID NO: 11, VLPs or BNPs comprising SEQ ID NO: 3, immunogenic compositions comprising SEQ ID NO: 3, or a vaccine comprising SEQ ID NO: 3.

As used herein, "BNP 4" or "CP-BNP 4" refers to SEQ ID NO: 4, nucleotide sequences encoding the amino acid sequence set forth in SEQ ID NO: 4, such as the nucleotide sequence set forth in SEQ ID NO: 12, VLPs or BNPs comprising SEQ ID NO: 4, immunogenic compositions comprising SEQ ID NO: 4, or a vaccine comprising SEQ ID NO: 4.

As used herein, "BNP 5" or "CP-BNP 5" refers to SEQ ID NO: 5, nucleotide sequences encoding the amino acid sequence set forth in SEQ ID NO: 5, such as the nucleotide sequence set forth in SEQ ID NO: 13, VLPs or BNPs comprising SEQ ID NO: 5, immunogenic compositions comprising SEQ ID NO: 5, or a vaccine comprising SEQ ID NO: 5.

As used herein, "BNP 6" or "CP-BNP 6" refers to SEQ ID NO: 6, nucleotide sequences encoding the amino acid sequence set forth in SEQ ID NO: 6, such as the nucleotide sequence set forth in SEQ ID NO: 14, VLPs or BNPs comprising SEQ ID NO: 6, immunogenic compositions comprising SEQ ID NO: 6, or a vaccine comprising SEQ ID NO: 6.

As used herein, "BNP 7" or "CP-BNP 7" refers to SEQ ID NO: 7, nucleotide sequences encoding the amino acid sequence set forth in SEQ ID NO: 7, such as the nucleotide sequence set forth in SEQ ID NO: 15, VLPs or BNPs comprising SEQ ID NO: 7, immunogenic compositions comprising SEQ ID NO: 7, or a vaccine comprising SEQ ID NO: 7.

As used herein, "BNP 8" or "CP-BNP 8" refers to SEQ ID NO: 8, nucleotide sequences encoding the amino acid sequence set forth in SEQ ID NO: 8, such as the nucleotide sequence set forth in SEQ ID NO: 16, VLPs or BNPs comprising SEQ ID NO: 8, immunogenic compositions comprising SEQ ID NO: 8, or a vaccine comprising SEQ ID NO: 8.

As used herein, "clearance profile (CP) epitope cyclic peptide 1" refers to SEQ ID NO: 17. As used herein, "CP epitope cyclic peptide 2" refers to SEQ ID NO: 18. As used herein, "CP epitope cyclic peptide 3" refers to SEQ ID NO: 19. As used herein, "CP epitope cyclic peptide 4" refers to SEQ ID NO: 20. As used herein, "CP epitope cyclic peptide 5" refers to SEQ ID NO: 21.

As used herein, the antibodies within an anti-HBs response which result in functional cure are referred to as "clearance antibodies." These antibodies define a "clearance profile" of antibodies which target the specific HBsAg epitopes and which ultimately result in clearance of HBsAg and functional cure. The epitopes are referred to as "clearance epitopes" meaning once occupied by antibodies in the host subject, the subject will result or likely result in a functional cure. Hence, a "clearance profile" can refer to the fingerprint of non-available epitopes on HBsAg or the suite or population of an individual's antibodies which occupy these epitopes and when they do occupy the epitopes are predictive of a functional cure being achieved. The clearance profile of antibodies or epitopes on HBsAg represent biomarkers of the potential or likelihood that a subject on treatment will achieve a functional cure. Reference to a "likelihood" of a functional cure generally means that the likelihood is 100%, that is, once a clearance profile of antibodies is detected, the subject will reach a state of functional cure or, in the absence of circulating HBsAg, has achieved a functional cure. However, as in any biological system, variability can occur. Hence, for the purposes of the present technology, reference to a "likelihood" of a functional cure means at least 80% probability that a subject with a clearance profile of antibodies will achieve a functional cure. By "at least 80% means 80, 81, 82, 83, 84, 85, 86, 87, 88, 89, 90, 91, 92, 93, 94, 95, 96, 97, 98, 99 or 100%.

The "clearance profile of epitopes" or "CP of epitopes" on HBsAg is the presence of available or non-available epitopes on HBsAg which have the potential to be occupied by the clearance antibodies. When the clearance profile of epitopes on HBsAg comprise no epitopes available for binding, then the epitopes are deemed "non-available" and this means that the epitopes are occupied by antibodies and a functional cure will likely occur. Alternatively, if no HBsAg is detected nor any circulating HBV DNA, then a functional cure has been achieved and only the clearance profile of antibodies is present (or can be induced in an immune response following exposure to HBV).

The term "standardized" also encompasses "normalization" of level of HBsAg or HBsAg-Ab complex and represents optimal level of HBsAg or HBsAg-Ab complex for the assay. A "blood-derived sample" includes serum.

III. Chronic Hepatitis B (CHB) Functional Cure

The clearance of serum HBsAg and/or seroconversion to anti-HBs, with undetectable serum HBV DNA, is considered to be a functional cure for CHB, as it allows not only for the cessation of therapy, but is also associated with significant reduction in the rates of liver cirrhosis and the development of hepatocellular carcinoma (HCC), and an overall increased survival rate (Fattovich G, et al. *Am J Gastroenterol.* 1998; 93(6):896-900; Yuen M F, et al. *Gastroenterology* 2008, 135(4): 1192-1199; Simonetti J, et al. *Hepatology* 2010, 51: 1531-1537). During spontaneous resolution of acute hepatitis B infection, a coordinated interaction of HBV-specific T cells and B cells eliminate infected hepatocytes, suppress viral replication via non-cytolytic pathways, and neutralize virions through the production of virus-specific antibodies (anti-HBs). Chronic infection represents failure of the host immune response to control HBV replication, with spontaneous clearance of HBsAg being uncommon, and found to occur in only 1-2% of patients. This rate is not enhanced with current antiviral therapies, but a key factor associated with this spontaneous loss is a low serum level of HBsAg of <100 IU/ml (Tseng T C, et al. *Gastroenterology* 2011, 141(2):517-525, 25 e1-2), and strategies designed to achieve such a level will form part of the treatment armamentarium. The mechanism(s) associated with HBsAg loss and/or seroconversion are unknown, but an effective B-cell response has been shown to be essential to maintain a functional hepatitis B cure, with B-cell depleting therapies (e.g., rituximab, anti-CD 20) being associated with HBV reactivation leading to liver failure and death (Shouval D. *Semin Liver Dis.* 2013; 33(2): 167-177). Clinical and diagnostic observations suggest that B-cell clones encoding anti-HBs with low affinity to the homologous HBsAg exist in patients with CHB (Gerlich W H. *Clin Infect Dis.* 2007; 44(9):1170-1172). Concurrently expressed anti-HBs in HBsAg-positive patients with CHB further suggests that the anti-HBS response is quantitatively and/or qualitatively insufficient or inadequate (weak) to overcome chronic infection, but does indicate that specific antibody production is not completely inhibited (Zhang J M, et al. *Clin Infect Dis.* 2007; 44(9): 1161-1169).

IV. Chronic Hepatitis B (CHB) Disease

Chronic hepatitis B (CHB) is an infectious disease that covers five recognizable and separate phases: Phase 1 is the immune tolerant (IT) phase covering the time from infection and establishment of chronic infection to the first signs of active disease. It is typically asymptomatic (no significant liver disease) and these individuals acquired infection at birth or shortly thereafter, and they are HBeAg-positive. Phase 2 or the immune clearance (IC) phase is a disease active phase with significant progression in the person's liver disease. These patients are also HBeAg-positive. In phase 3 or the non-replicative phase (NR) there is little or no evidence of active liver disease; viruses can be identified at low level, and the person is HBeAg-negative. Phase 4 is a relapse or recrudescence in liver disease activity and viral replication and this phase is also known as HBeAg-negative disease. This phase tends to eventually burn itself out and then patients often have cirrhosis. The final phase, phase 5, is identified as HBsAg loss and anti-HBs seroconversion. This is also recognised as the functional cure (FC) phase.

CHB comprises at least 4 different diseases based on HBV genotypes. Thus, CHB can be considered under Asian CHB (genotypes B and C), European CHB (genotypes A-2 and D), African CHB (genotypes A-1 and E) and Latin American CHB (genotypes F and H) and each of these 4 groups have different ethnicities (Asian versus European/Caucasian versus African versus Latino), age of acquisition (perinatal versus early childhood versus early adult hood) and mode of transmission (mother-to-baby, child-to-child, cultural scarification, iatrogenic/parenteral and sexual), respectively. Recombination between different genotypes (e.g., A and D, or B and C) is not uncommon. CHB can be further stratified on the basis of HBeAg and disease status; either HBeAg-positive or HBeAg-negative, with or without liver disease.

Figure 2:
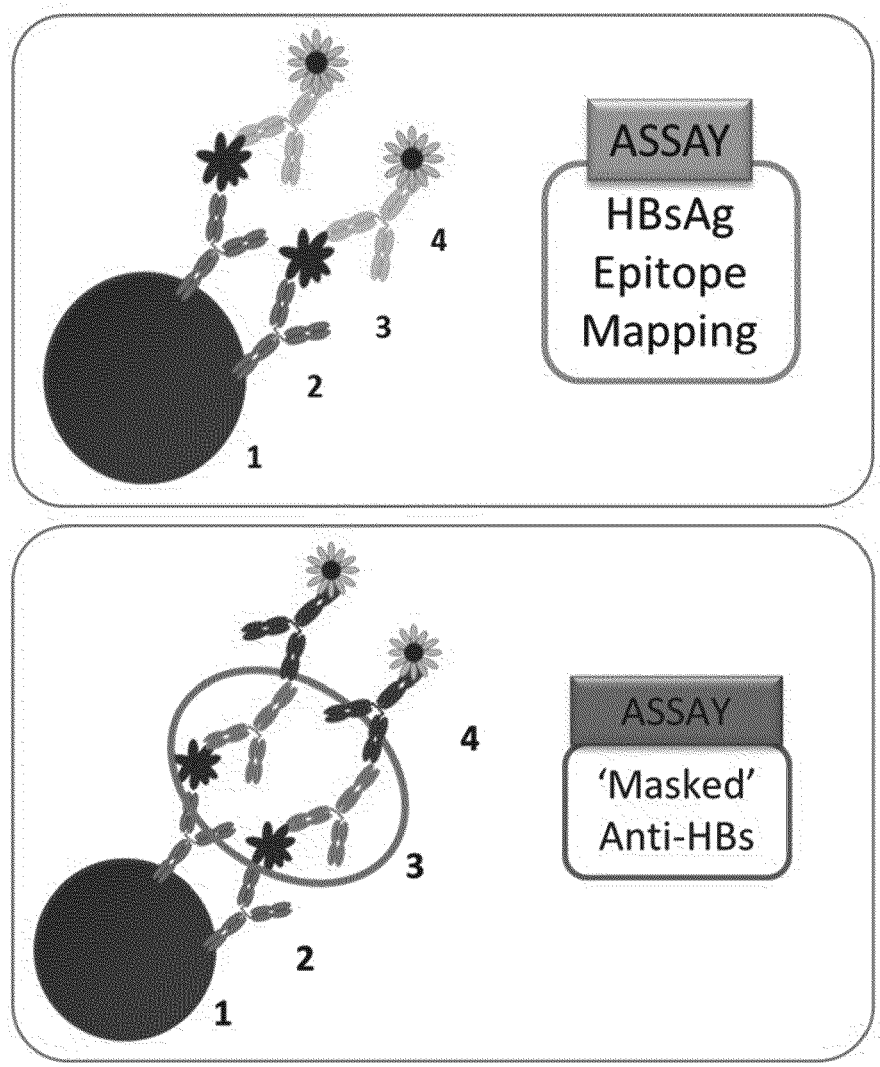
FIG. 2 is a diagrammatic representation of predictive biomarkers of
functional CHB cure (assay 1) and immune Ab response activity (assay2). Assay 1 (top panel): 1. Magnetic bead; 2. Capture Ab: multiplex mouse anti-HBs mAbs to HBsAg 'external region'; 3. Patient HBsAg sample; 4. Reporter Ab: PE conjugated polyclonal anti-HBS. Assay 2 (lower panel): 1. Magnetic bead; 2. Capture Ab: 2plex mouse anti-HBs mAbs to HBsAg 'external region'; 3. Patient sample: complexed anti-HBs (with HBsAg); 4. Reporter Ab: HRP conjugated goat anti-human IgG Fc domain.

A FC-P is associated with FC and is demonstrated by loss of epitope recognition at loop 1 and loop 2 within the external loop region, which includes the "a" determinant of HBsAg when using mAbs 5, 6, 7, and 8 (see FIGS. 1 and 2). Anti-HBS responses following a cure outcome "induce" an FC-P against reference HBsAg samples. In some embodiments described herein, vaccination using a BNP platform comprising FC-P associated epitopes (loop 1 +loop 2) generates an anti-HBs response associated with an FC-P enhancing the chance for cure.

V. HBsAg, anti-HBs, and CP/F-CP

Measurement of the epitope profile of the envelope protein (HBsAg) of the HBV circulating in a patient's blood is a direct measure of the virus; it comprises the detection of a foreign antigen found in the patient's blood. The logic or argument developed in the CP is that an infected person will mount an immune response against the virus and the effects of that immune response selection pressure on the virus can be measured. The effect can be demonstrated as HBsAg epitope changes on the envelope of the virus in that person. The CP is measured across a multiplex reporting panel (FIG. 2). The FC-P is reported against reactivity to a 4plex panel applied to a natural history cohort run at St. Vincent's Hospital Melbourne, within which the patients were HBeAg negative and had minimal or no disease activity, were in phase 4 and transitioning to phase 5, with the infecting genotype unrestricted (i.e., genotypes A, B, C, or D). In contrast, the measure of an antibody made by the patient is a direct measure of the host's response to the virus; it is also found circulating in the patient's blood. The logic or argument developed in the FC-P is that a person who has cured their CHB has successfully mounted an antibody response, whose effect can be measured. The effect can be demonstrated by the ability of that antibody to induce epitope changes onto exogenously supplied HBsAg of panels of HBV; that is, the patients' antibody "induces" an epitope profile response on supplied, exogenous antigen. An "induced" FC-P applies to the Natural History cohort of phase 4/5, HBeAg negative, genotype unrestricted, CHB patients, which is based on a 4plex reporting panel.

VI. HBsAg, VLPs, and BNPs

HBV encodes three HBsAg proteins that form the viral envelope; small (S), middle (M) and large (L) (Carman W F, et al. *J. Hepatol.* 1999; 31(2):195-201; Seeger C, et al. *Hepadnaviruses.* 2013). All share a common 226-residue HBsAg-S domain (Seeger C, et al. *Hepadnaviruses.* In "*Fields Virology*", 2013, 6th edition. pp. 2180-2221), whilst N-terminal extensions of M and L encode the PreS2 and PreS1 domains respectively. The HBsAg envelope proteins are key viral antigens; during infection, S, M, and L are expressed and co-packaged through the ER membrane of the host cell, for the formation of the envelope of infectious HBV particles. S proteins are the sole antigenic components of the hepatitis B vaccine able to induce protective antibodies mainly directed to the major antigenic 'a' determinant of the external loop region (residues 99-169). S proteins readily self-assemble into lipid-associated VLPs, and form the basis of the current recombinant vaccines, which are made in yeast and are not glycosylated. The S protein has not been crystallized but is considered a conformationally dynamic protein containing numerous cysteine and proline residues, predicted to form discrete loop domains (loop 1:aa 107-135; loop 2:aa 139-149) within the immunodominant 'a' determinant (Stirk H J, et al. *Intervirology.* 1992, 33(3):148-158). The cDNA sequence encoding the S protein is set forth in SEQ ID NO: 22. The cDNA sequence encoding the S protein with an AgeI restriction site and FLAG tag is set forth in SEQ ID NO: 23. Alterations (variants and antibody occupancy) within the 'a' determinant can modify HBsAg topology and directly influence the HBV neutralization phenotype (Carman W F, et al. *J Hepatol.* 1999; 31(2):195-201).

The cDNA sequence encoding the HBsAg-S protein having the amino acid sequence of SEQ ID NO: 50 is set forth in SEQ ID NO: 22. The cDNA sequence encoding the S protein having the amino acid sequence of SEQ ID NO: 51 is set forth in SEQ ID NO: 23. The HBsAg-S cDNA and amino acid sequences are provided below in Table A.

TABLE A

| HBsAg-S cDNA and Amino Acid Sequences |
|---|
| cDNA encoding the small version of the hepatitis B surface antigen (SEQ ID NO: 22)<br>Start ATG and stop codon TAA in bold<br>The sequence encoding the external loop region (amino acids 100-160) is underlined<br>ATGGAGAACATCACATCAGGATTCCTAGGACCCCTTCTCGTGTTACAGGCGGGGTTT<br>TTCTTGTTGACAAGAATCCTCACAATACCGCAGAGTCTAGACTCGTGGTGGACTTCT<br>CTCAATTTTCTAGGGGGAACTACCGTGTGTCTTGGCCAAAATTCGCAGTCCCCAACC<br>TCCAATCACTCACCAACCTCTTGTCCTCCAACTTGTCCTGGTTATCGCTGGATGTGT<br>CTGCGGCGTTTTATCATCTTCCTCTTCATCCTGCTGCTATGCCTCATCTTCTTGTTG |

TABLE A-continued

HBsAg-S cDNA and Amino Acid Sequences

```
GTTCTTCTGGACTATCAAGGTATGTTGCCCGTTTGTCCTCTAATTCCAGGATCCTCA
ACAACCAGCACGGGACCATGCCGGACCTGCATGACTACCGGTCAAGGAACCTCTATG
TATCCCTCCTGTTGCTGTACCAAACCTTCGGACGGAAATTGCACCTGTATTCCCATC
CCATCATCCTGGGCTTTCGGAAAATTCCTATGGGAGTGGGCCTCAGCCCGTTTCTCC
TGGCTCAGTTTACTAGTGCCATTTGTTCAGTGGTTCGTAGGGCTTTCCCCCACTGTT
TGGCTTTCAGTTATATGGATGATGTGGTATTGGGGGCCAAGTCTGTACAGCATCTTG
AGTCCCTTTTTACCGCTGTTACCAATTTTCTTTTGTCTTTGGGTATACATTTAA
``` cDNA encoding the small version of the hepatitis B surface
antigen, with the introduced AgeI restriction site, and a
cDNA sequence encoding the tag "FLAG" (SEQ ID NO: 23)
Start ATG and stop codon TAA in bold
FLAG-specific DNA sequence (highlighted in grey)
The introduced AgeI restriction site in italic
The sequence encoding the external loop region (amino acids
100-160) is underlined

```
ATGGACTATAAAGACGACGATGACAAAGAGAACATCACATCAGGATTCCTAGGACCC
CTTCTCGTGTTACAGGCGGGGTTTTTCTTGTTGACAAGAATCCTCACAATACCGCAG
AGTCTAGACTCGTGGTGGACTTCTCTCAATTTTCTAGGGGGAACTACCGTGTGTCTT
GGCCAAAATTCGCAGTCCCCAACCTCCAATCACTCACCAACCTCTTGTCCTCCAACT
TGTCCTGGTTATCGCTGGATGTGTCTGCGGCGTTTTATCATCTTCCTCTTCATCCTG
CTGCTATGCCTCATCTTCTTGTTGGTTCTTCTGGACTATCAAGGTATGTTGCCCGTT
TGTCCTCTAATTCCAGGATCCTCAACAACCAGCACGGGACCATGCCGGACCTGCATG
ACTACCGGTCAAGGAACCTCTATGTATCCCTCCTGTTGCTGTACCAAACCTTCGGAC
GGAAATTGCACCTGTATTCCCATCCCATCATCCTGGGCTTTCGGAAAATTCCTATGG
GAGTGGGCCTCAGCCCGTTTCTCCTGGCTCAGTTTACTAGTGCCATTTGTTCAGTGG
TTCGTAGGGCTTTCCCCCACTGTTTGGCTTTCAGTTATATGGATGATGTGGTATTGG
GGGCCAAGTCTGTACAGCATCTTGAGTCCCTTTTTACCGCTGTTACCAATTTTCTTT
TGTCTTTGGGTATACATTTAA
```

Hepatitis B surface antigen S (HBsAg-S) protein (SEQ ID
NO: 50)
External loop region between 100 and 160 amino acid position
is underlined
MENITSGFLGPLLVLQAGFFLLTRILTIPQSLDSWWTSLNFLGGTTVCLGQNSQSPT
SNHSPTSCPPTCPGYRWMCLRRFIIFLFLILLLCLIFLLVLLD*YQGMLPVCPLIPGSS*
*TTSTGPCRTCMTTGQGTSMYPSCCCTKPSDGNCTCIPIPSSWAFGKF*LWEWASARFS
WLSLLVPFVQWFVGLSPTVWLSVIWMMWYWGPSLYSILSPFLPLLPIFFCLWVYI*

Hepatitis B surface antigen S (HBsAg-S) protein and a FLAG
tag (SEQ ID NO: 51)
FLAG sequence (highlighted in grey)
External loop region between 100 and 160 amino acid position
is underlined
MDYKDDDDKENITSGFLGPLLVLQAGFFLLTRILTIPQSLDSWWTSLNFLGGTTVCL
GQNSQSPTSNHSPTSCPPTCPGYRWMCLRRFIIFLFILLLCLIFLLVLLDYQGMLPV
CPLIPGSSTTSTGPCRTCMTTGQGTSMYPSCCCTKPSDGNCTCIPIPSSWAFGKFLW
EWASARFSWLSLLVPFVQWFVGLSPTVWLSVIWMMWYWGPSLYSILSPFLPLLPIFF
CLWVYI*

HBsAg VLPs are highly compact due to the large number of intra- and intermolecular disulphide bonds within and between the individual subunits (Seeger C, et al. *Hepadnaviruses*. In "*Fields Virology*", 2013, 6th edition. pp. 2180-2221; Mangold C M, et al. *Arch Virol.* 1997, 142(11):2257-2267), and clinical trials have established that they can be successfully modified to display inserted foreign antigenic and medically-relevant sequences as bio-nanoparticle (BNP) delivery platforms (Beaumont E, et al. *Vaccine.* 2015, 33(8): 973-976; Buonaguro L, et al. *Expert Rev Vaccines.* 2011, 10(11):1569-1583; Cheong W S, et al. *Antiviral Res.* 2009, 81(2): 113-122; Moffat J M et al. *Vaccine.* 2013, 31(18): 2310-2316; Netter H J, et al. *J Virology* 2001;75(5):2130-2141; Phogat S et al. *Virology.* 2008, 373(1):72-84).

VII. Clearance Epitopes of HBsAg Loop 1 and Loop 2

The clearance epitopes on HBsAg are those that when occupied by antibodies in a subject, the likely result is a functional cure. The epitopes are located on each of Loop 1 and Loop 2 of HBsAg-S. In relation to the assay, monoclonal antibodies (mAbs) are selected for use in a multiplex assay which target a range of epitopes on HBsAg-S. One set of mAbs designated mAb5 and 6 targets the Loop 1 epitopes. Two Loop 1 epitopes are screened defined by the consensus amino acid sequence:

$CX_1TCX_2X_3X_4X_5QGX_6SMX_7PC$ (SEQ ID NO: 24), wherein:

$X_1$ is sK122 (Genotypes A1, A2, A6, B1, B2, B3, B6, C, F, G, H, I) or sR122 (Genotypes A3, A4, A5, B3, B4, B5, B7, B8, B9, C2, C4, D, E);

$X_2$ is sT125 (Genotype A, B, C, D, E, F, G, H, I) or sM125 (genotype D3, D5);

$X_3$ is sT126 (Genotypes A, B, C, D, E, F, G, H, I) or sI126 (Genotype C);

$X_4$ is sP127 (Genotypes A, B, E, C, D, G, I) or sT127 (genotype C4, D2, D5) or sL127 (genotype E, F, H);

$X_5$ is sA128 (A, B, C, D, E, F, G, H, I) or sV128 (D2);

$X_6$ is sN131 (Genotypes A, G, I) or sT131 (Genotypes B, C, D, E, F, H);

$X_7$ is sF134 (Genotype A, B, C, E, F, H) or sY134 (Genotype D, G, I);

and the consensus amino acid sequence to which mAb 10 binds $PCX_8TCX_9X_{10}X_{11}$ (SEQ ID NO: 25), wherein:

$X_8$ is sK122 (Genotypes A1, A2, A6, B1, B2, B3, B6, C, F, G, H, I) or sR122 (Genotypes A3, A4, A5, B3, B4, B5, B7, B8, B9, C2, C4, D, E);

$X_9$ is sT125 (Genotype A, B, C, D, E, F, G, H, I) or sM125 (genotype D3, D5);

$X_{10}$ is sT126 (Genotypes A, B, C, D, E, F, G, H, I) or sI126 (Genotype C) or sS126 or sA126 (common variants);

$X_{11}$ is sP127 (Genotypes A, B, E, C, D, G, I) or sT127 (genotype C4, D2, D5) or sL127 (genotype E, F, H);

Another set of mAbs (designated mAb, 7, 8, 11, 12, 16, and 17) targets an epitope on Loop 2 defined by the consensus amino acid sequence:

CCCTKPX$_{12}$DGNCX$_{13}$ (SEQ ID NO: 26)

wherein:

$X_{12}$ is sT140 (Genotype A, B, C, D, G, H, I) or sS140 (Genotype E or F); and $X_{13}$ is sT143 (Genotype A, B) or sS143 (Genotype C, D, E, F, G, H, I).

Without wishing to be bound by theory, it is proposed herein that when either epitope at Loop 1 is occupied, when the epitope at Loop 2 is occupied, or when either epitope at Loop 1 is occupied together with the epitope at Loop 2, then a clearance profile of antibodies has been achieved resulting in functional clearance.

In an embodiment, the epitopes occupied are CKTCTTPAQGNSMFPSC (SEQ ID NO: 27); and/or PCKTCTTP (SEQ ID NO: 28); and CCCTKPTDGNCT (SEQ ID NO: 29).

In an embodiment, the epitopes occupied are CKTCTIPAQGTSMFPSC (SEQ ID NO: 30); and/or PCKTCTTP (SEQ ID NO: 28); and CCTKPSDGNCT (SEQ ID NO: 31).

In an embodiment the epitopes occupied are CRTCTTPAQGTSMFPSC (SEQ ID NO: 32); and/or PCKTCTTP (SEQ ID NO: 28); and CCTKPSDGNCT (SEQ ID NO: 31).

VIII. Clearance Profile-Bio Nanoparticle (CP-BNP) Therapeutic Vaccine Formulations The disclosure of the present technology relates to the development of 8 CP-BNPs (SEQ ID NOs: 1-8) encompassing the pan-genotypic/serotypic loop 1 and loop 2 HBsAg target epitopes, alongside a control wild-type (WT) BNP. The BNP backbone consists of HBsAg-S envelope protein non-infectious subviral particles (virus-like particles, or VLPs, that do not contain all the components of the complete virus). In some embodiments, the HBV genotype is genotype A, A1, A2, A3, A4, A5, A6, B, B1, B2, B3, B4, B5, B6, B7, B8, B9, C, C1, C2, C4, D, D2, D3, D5, E, F, G, H, or I. In some embodiments, the HBV genotype is genotype D. In some embodiments, the serotype is ayw or adw. In some embodiments, the serotype is ayw. The modification of VLPs as bio-nanoparticles (BNPs) to deliver target insert epitopes represents an active approach, which stimulates the immune system to induce a response able to treat or cure (clear) a persistent hepatitis B virus infection. Antibodies will be generated which are able to induce a cure of an existing and persistent hepatitis B infection. The CP epitope target (insert) sequences are listed in Table 1 below. BNPs are produced and purified (endo-free), and assessed for immunogenicity individually and in formulations that consider combinations of loop 1 and loop 2 target epitopes. The formulations analysed are listed in Table 2 below.

TABLE 1

Target HBsAg CP Epitopes

| CP-BNP | CP epitope name | Insert CP epitope sequence | Insert epitope number | Insert location in BNP |
|---|---|---|---|---|
| 1 | Miniloop 1 (adw, geno A/C) | PCKTCTTP (residues 120-127) (SEQ ID NO: 28) | trimer | AgeI site (aa126-128) |
| 2 | Miniloop 1 (ayw, geno B/D) | PCRTCTTP (residues 120-127) (SEQ ID NO: 33) | trimer | AgeI site (aa126-128) |
| 3 | Loop 2 (adw/ayw) | CTKPTDGNC (residues 139-147) (SEQ ID NO: 34) | trimer | AgeI site (aa126-128) |
| 4 | Loop 1 extended (adw/ayw) | CKTCTTPAQGNSMFPS (residues 121-136) (SEQ ID NO: 35) | dimer | AgeI site (aa126-128) |
| 5 | Loop 2 (adw/ayw) | CTKP(T/S)TDGNC (residues 139-147) (SEQ ID NO: 36) | trimer | Native site, loop2 |
| 6 | Miniloop 1 (adw, geno A-D) | PC(K/R)TC(T/M)TP (residues 120-127) (SEQ ID NO: 37) | trimer | Native site, loop1 |
|   | Loop 2 (adw, geno A-D) | CTKP(T/S)TDGNC (residues 139-147) (SEQ ID NO: 36) | trimer | Native site, loop2 |
| 7 | Loop 1 extended (adw/ayw) | C(K/R)TC(T/M)T(P/T)AQG(N/T)SM(F/Y)PS (residues 121-136) (SEQ ID NO: 38) | trimer | Native site, loop1 |
| 8 | Loop 1 + Loop 2 (adw/ayw) | PCRTCMTTAQGTSMYPSCCCTKPSDGNC (residues 120-147) (SEQ ID NO: 39) PCKTCTTPAQGNSMFPSCCCTKPTDGNC (residues 120-147) (SEQ ID NO: 40) | dimer | Native site |

TABLE 2

CP-BNP Formulations

| CP-BNP formulation | Loop1 epitope retained | Loop2 epitope retained | Antigenic | Anti-HBs CP-associated (Induced CP) |
|---|---|---|---|---|
| 1 | Y | Y | Y | N |
| 2 | Y | Y | Y | N |
| 3 | Y | Y | Y | Y |
| 4 | Y | Y | Y | N |
| 1 + 3 | Y | Y | Y | Y |
| 1 + 3 + 4 | Y | Y | Y | Y |
| 3 + 4 | Y | Y | Y | Y |
| 5 | Y | Y | Y | Y |
| 6 | Y | Y | Y | Y |
| 7 | Y | Y | Y | NT |
| 8 | Y | Y | Y | Y |
| 5 + 7 | NT | NT | Y | Y |
| 1 + 4 + 5 | Y | Y | Y | Y |
| WT | Y | Y | Y | N |

The amino acid sequences of the 8 CP-BNP constructs are provided in Table 3, Construct 1 (BNP 1) (SEQ ID NO: 1), Construct 2 (BNP 2) (SEQ ID NO: 2), Construct 3 (BNP 3) (SEQ ID NO: 3), Construct 4 (BNP 4) (SEQ ID NO: 4), Construct 5 (BNP 5) (SEQ ID NO: 5), Construct 6 (BNP 6) (SEQ ID NO: 6), Construct 7 (BNP 7) (SEQ ID NO: 7), and Construct 8 (BNP 8) (SEQ ID NO: 8).

TABLE 3

CP-BNP Construct Amino Acid Sequences

```
Gene name: Construct 1 (BNP 1) (SEQ ID NO: 1)
Parent (vector sequence): HBsAg small, genotype D, serotype ayw
Insert via AgeI restriction site
Insertion: Miniloop 1 120-PCKTCTTP-127 (SEQ ID NO: 28) (trimer): genotype A-specific
insert, adw, (in bold)
linker: GSGS (SEQ ID NO: 53) (underlined and italics)
FLAG-tag (underlined)
MDYKDDDDKENITSGFLGPLLVLQAGFFLLTRILTIPQSLDSWWTSLNFLGGITVCLGQNSQSPTSN
HSPTSCPPTCPGYRWMCLRRFIIFLFILLLCLIFLLVLLDYQGMLPVCPLIPGSSITSTGPCRTCMT
TGSGSPCKTCTTPGSGSPCKTCTTPGSGSPCKTCTTPGSGSTGQGTSMYPSCCCTKPSDGNCTCIPI
PSSWAFGKFLWEWASARFSWLSLLVPFVQWFVGLSPTVWLSVIWMMWYWGPSLYSILSPFLPLLPIF
FCLWVYI*

Gene name: Construct 2 (BNP 2) (SEQ ID NO: 2)
Parent (vector sequence): HBsAg small, genotype D, serotype ayw
Insert via AgeI restriction site
Insertion: Miniloop 1 PCRTCTTP (SEQ ID NO: 33) (trimer): genotypes B/C-specific insert,
ayw (in bold)
linker: GSGS (SEQ ID NO: 53) (underlined and italics)
FLAG-tag (underlined)
MDYKDDDDKENITSGFLGPLLVLQAGFFLLTRILTIPQSLDSWWTSLNFLGGITVCLGQNSQSPTSN
HSPTSCPPTCPGYRWMCLRRFIIFLFILLLCLIFLLVLLDYQGMLPVCPLIPGSSITSTGPCRTCMT
TGSGSPCRICTTPGSGSPCRICTTPGSGSPCRICTTPGSGSTGQGTSMYPSCCCTKPSDGNCTCIPI
PSSWAFGKFLWEWASARFSWLSLLVPFVQWFVGLSPTVWLSVIWMMWYWGPSLYSILSPFLPLLPIF
FCLWVYI*

Gene name: Construct 3 (BNP 3) (SEQ ID NO: 3)
Parent (vector sequence): HBsAg small, genotype D, serotype ayw
Insert via AgeI restriction site
Insertion: Loop 2 139-CTKPTDGNC-147 (SEQ ID NO: 34) (trimer) (in bold)
linker: GSGS (SEQ ID NO: 53) (underlined and italics)
FLAG-tag (underlined)
MDYKDDDDKENITSGFLGPLLVLQAGFFLLTRILTIPQSLDSWWTSLNFLGGTTVCLGQNSQSPTSN
HSPTSCPPTCPGYRWMCLRRFIIFLFILLLCLIFLLVLLDYQGMLPVCPLIPGSSITSTGPCRTCMT
TGSGSCTKPTDGNCGSGSCTKPTDGNCGSGSCTKPTDGNCGSGSTGQGTSMYPSCCCTKPSDGNCTC
IPIPSSWAFGKFLWEWASARFSWLSLLVPFVQWFVGLSPTVWLSVIWMMWYWGPSLYSILSPFLPLL
PIFFCLWVYI*

Gene sequence: Construct 4 (BNP 4) (SEQ ID NO: 4)
Parent (vector sequence): HBsAg small, genotype D, serotype ayw
Insert via AgeI restriction site
Insertion: Loop 1 121-CKTCTTPAQGNSMFPS-136 (SEQ ID NO: 35) (dimer), adw (in bold)
Start ATG and stop codon: enlarged font
linker: GSGS (SEQ ID NO: 53) (underlined and italics)
FLAG-tag (underlined)
MDYKDDDDKENITSGFLGPLLVLQAGFFLLTRILTIPQSLDSWWTSLNFLGGTTVCLGQNSQSPTSN
HSPTSCPPTCPGYRWMCLRRFIIFLFILLLCLIFLLVLLDYQGMLPVCPLIPGSSITSTGPCRTCMT
TGSGSCKTCTTPAQGNSMFPSGSGSCKTCTTPAQGNSMFPSGSGSTGQGTSMYPSCCCTKPSDGNCT
CIPIPSSWAFGKFLWEWASARFSWLSLLVPFVQWFVGLSPTVWLSVIWMMWYWGPSLYSILSPFLPL
LPIFFCLWVYI*
```

TABLE 3-continued

CP-BNP Construct Amino Acid Sequences

Gene sequence: Construct 5 (BNP 5) [Loop 2 sequences in natural context] (SEQ ID NO: 5)
Parent (vector sequence): HBsAg small, genotype D, serotype ayw
Design: Three repeats in loop 2 region-Original sequence (in bold) and two additional inserts
(in bold and highlighted)
Loop 2 original sequence encoding 139-CTKPSDGNC-147 (SEQ ID NO: 54) (ayw), unchanged (in
bold), then two additional loop 2 sequences (adw) 139-CTKPTDGNC-147 (SEQ ID NO: 34) (dimer)
(in bold and highlighted)
Linker: GSGS (SEQ ID NO: 53) (underlined and italic)
FLAG-tag (underlined)
MDYKDDDDKENITSGFLGPLLVLQAGFFLLTRILTIPQSLDSWWTSLNFLGGTTVCLGQNSQSPTSN
HSPTSCPPTCPGYRWMCLRRFIIFLFILLLCLIFLLVLLDYQGMLPVCPLIPGSSITSTGPCRTCMT
TGQGTSMYPSCCCTKPSDGNC*GSGS*CTKPTDGNC*GSGS*CTKPTDGNCTCIPIPSSWAFGKFLWEWAS
ARFSWLSLLVPFVQWFVGLSPTVWLSVIWMMWYWGPSLYSILSPFLPLLPIFFCLWVYI*

Gene sequence: Construct 6 (BNP 6) +Loop 1 and 2 dimers+ (SEQ ID NO: 6)
Parent (vector sequence): HBsAg small, genotype D, serotype ayw
Design:
Loop 1 and loop 2 repeats (in total trimer); in addition to the original ayw loop 1
and ayw loop2
sequences, two adw loop 1 (dimer) and loop 2 (dimer) sequences added.
Loop 1 region (original ayw sequence in bold, and two additional adw loop 1 sequences,
in bold and highlighted). Miniloop 1 120-PCKTCTTP-127 (SEQ ID NO: 28) (dimer, serotype adw)
followed by original 120-PCRTCMTT-127 (SEQ ID NO: 55) (serotype ayw)
Loop 2 region (enlarged font):
Loop 2 original sequence 139-CTKPSDGNC-147 (SEQ ID NO: 54) (ayw) (in bold) followed by adw
dimer 139-CTKPTDGNC-147 (SEQ ID NO: 34) (in bold and highlighted)
Linker: GSGS (SEQ ID NO: 53) (underlined and italic)
FLAG-tag (underlined)
MDYKDDDDKENITSGFLGPLLVLQAGFFLLTRILTIPQSLDSWWTSLNFLGGITVCLGQNSQSPTSN
HSPTSCPPTCPGYRWMCLRRFIIFLFILLLCLIFLLVLLDYQGMLPVCPLIPGSSITSTGPCKTCTT
P*GSGS*PCKTCTTP*GSGS*PCRTCMTTAQGTSMYPSCCCTKPSDGNC*GSGS*CTKPTDGNC*GSGS*CT
KPIDGNCTCIPIPSSWAFGKFLWEWASARFSWLSLLVPFVQWFVGLSPTVWLSVIWMMWYWGPSLY
SILSPFLPLLPIFFCLWVYI*

Gene sequence: Construct 7 (BNP 7) (SEQ ID NO: 7)
Parent (vector sequence): HBsAg small, genotype D, serotype ayw
Design:
Loop 1, adw, dimer. 121-CKTCTTPAQGNSMFPS-136 (SEQ ID NO: 35) (in bold and highlighted)
Loop 1 ayw, monomer. 121-PCRTCMTTAQGTSMYPS-136 (SEQ ID NO: 48) (in bold)
Start ATG and stop codon: enlarged font
Linker: GSGS (SEQ ID NO: 53) (underlined and italics)
FLAG-tag (underlined)
MDYKDDDDKENITSGFLGPLLVLQAGFFLLTRILTIPQSLDSWWTSLNFLGGITVCLGQNSQSPTSN
HSPTSCPPTCPGYRWMCLRRFIIFLFILLLCLIFLLVLLDYQGMLPVCPLIPGSSITSTGPCKTCTT
PAQGNSMFPSC*GSGS*CKTCTTPAQGNSMFPSC*GSGS*PCRTCMTTAQGTSMYPSCCCTKPSDGNCTCI
PIPSSWAFGKFLWEWASARFSWLSLLVPFVQWFVGLSPTVWLSVIWMMWYWGPSLYSILSPFLPLLP
IFFCLWVYI*

Gene sequence: Construct 8 (BNP 8) (Complete loop regions 120-147 ayw and adw present)
(SEQ ID NO: 8)
Parent (vector sequence): HBsAg small, genotype D, serotype ayw
Design:
Original ayw loop in bold
Added adw derived loop sequence, in bold and highlighted
Linker: GSGS (SEQ ID NO: 53) (underlined and italic)
FLAG-tag (underlined)
MDYKDDDDKENITSGFLGPLLVLQAGFFLLTRILTIPQSLDSWWTSLNFLGGITVCLGQNSQSPTSN
HSPTSCPPTCPGYRWMCLRRFIIFLFILLLCLIFLLVLLDYQGMLPVCPLIPGSSITSTGPCRTCMT
TAQGTSMYPSCCCTKPSDGNC*GSGS*PCKTCTTPAQGNSMFPSCCCTKPIDGNCTCIPIPSSWAFGKF
LWEWASARFSWLSLLVPFVQWFVGLSPTVWLSVIWMMWYWGPSLYSILSPFLPLLPIFFCLWVYI*

Exemplary nucleotide sequences encoding the 8 CP-BNP amino acid constructs are provided in Table 4.

TABLE 4

CP-BNP Construct Exemplary Nucleotide Sequences

Gene name: Construct 1 (BNP 1) (SEQ ID NO: 9)
Parent (vector sequence): HBsAg small, genotype D, serotype ayw
Insert via AgeI restriction site (ACCGGT)
Insertion: Miniloop 1 120-PCKTCTTP-127 (SEQ ID NO: 28) (trimer): genotype A-specific insert,
adw (in bold)
Start ATG and stop codon: enlarged font TABLE 4-continued

| CP-BNP Construct Exemplary Nucleotide Sequences |
|---| linker: GSGS (SEQ ID NO: 53) (underlined and italic)
FLAG-tag (underlined)
GAGCTCGCCACCATGGACTATAAAGACGACGATGACAAAGAGAACATCACATCAGGATTCCTAGGAC
CCCTTCT
CGTGTTACAGGCGGGGTTTTTCTTGTTGACAAGAATCCTCACAATACCGCAGAGTCTAGACTCGTGGT
GGACTTC
TCTCAATTTTCTAGGGGGAACTACCGTGTGTCTTGGCCAAAATTCGCAGTCCCCAACCTCCAATCACT
CACCAAC
CTCTTGTCCTCCAACTTGTCCTGGTTATCGCTGGATGTGTCTGCGGCGTTTTATCATCTTCCTCTTCA
TCCTGCT
GCTATGCCTCATCTTCTTGTTGGTTCTTCTGGACTATCAAGGTATGTTGCCCGTTTGTCCTCTAATTC
CAGGATC
CTCAACAACCAGCACGGGACCATGCCGGACCTGCATGACTACC*GGTTCCGGTTCA*CCCTGCAAAACCT
GTACTAC
CCCA*GGTTCCGGATCA*CCCTGCAAAACCTGTACTACCCCA*GGTTCCGGATCA*CCCTGCAAAACCTGTA
CTACCCC
A*GGTTCCGGATCA*ACCGGTCAAGGAACCTCTATGTATCCCTCCTGTTGCTGTACCAAACCTTCGGACG
GAAATTG
CACCTGTATTCCCATCCCATCATCCTGGGCTTTCGGAAAATTCCTATGGGAGTGGGCCTCAGCCCGTT
TCTCCTG
GCTCAGTTTACTAGTGCCATTTGTTCAGTGGTTCGTAGGGCTTTCCCCCACTGTTTGGCTTTCAGTTA
TATGGAT
GATGTGGTATTGGGGGCCAAGTCTGTACAGCATCTTGAGTCCCTTTTTACCGCTGTTACCAATTTTCT
TTTGTCT
TTGGGTATACATTTAACTCGAG Gene name: Construct 2 (BNP 2) (SEQ ID NO: 10)
Parent (vector sequence): HBsAg small, genotype D, serotype ayw
Insert via AgeI restriction site (ACCGGT)
Insertion: Miniloop 1 PCRTCTTP (SEQ ID NO: 33) (trimer): genotypes B/C-specific insert, ayw (in bold)
Start ATG and stop codon: enlarged font
linker: GSGS (SEQ ID NO: 53) (underlined and italic)
FLAG-tag (underlined)
GAGCTCGCCACCATGGACTATAAAGACGACGATGACAAAGAGAACATCACATCAGGATTCCTAGGACCCCT
TCT
CGTGTTACAGGCGGGGTTTTTCTTGTTGACAAGAATCCTCACAATACCGCAGAGTCTAGACTCGTGGTGGAC
TTC
TCTCAATTTTCTAGGGGGAACTACCGTGTGTCTTGGCCAAAATTCGCAGTCCCCAACCTCCAATCACTCACC
AAC
CTCTTGTCCTCCAACTTGTCCTGGTTATCGCTGGATGTGTCTGCGGCGTTTTATCATCTTCCTCTTCATCCT
GCT
GCTATGCCTCATCTTCTTGTTGGTTCTTCTGGACTATCAAGGTATGTTGCCCGTTTGTCCTCTAATTCCAGG
ATC
CTCAACAACCAGCACGGGACCATGCCGGACCTGCATGACTACC*GGTTCCGGTTCA*CCCTGCCGGACCTGTAC
TAC
CCCA*GGTTCCGGATCA*CCCTGCCGGACCTGTACTACCCCA*GGTTCCGGATCA*CCCTGCCGGACCTGTACTAC
CCC
A*GGTTCCGGATCA*ACCGGTCAAGGAACCTCTATGTATCCCTCCTGTTGCTGTACCAAACCTTCGGACGGAAA
TTG
CACCTGTATTCCCATCCCATCATCCTGGGCTTTCGGAAAATTCCTATGGGAGTGGGCCTCAGCCCGTTTCTC
CTG
GCTCAGTTTACTAGTGCCATTTGTTCAGTGGTTCGTAGGGCTTTCCCCCACTGTTTGGCTTTCAGTTATATG
GAT
GATGTGGTATTGGGGGCCAAGTCTGTACAGCATCTTGAGTCCCTTTTTACCGCTGTTACCAATTTTCTTTTG
TCT
TTGGGTATACATTTAAcTCGAG Gene name: Construct 3 (BNP 3) (SEQ ID NO: 11)
Parent (vector sequence): HBsAg small, genotype D, serotype ayw
Insert via AgeI restriction site (ACCGGT)
Insertion: Loop 2 139-CTKPTDGNC-147 (SEQ ID NO: 34) (trimer)
Start ATG and stop codon: enlarged font
linker: GSGS (SEQ ID NO: 53) (underlined and italic)
FLAG-tag (underlined)
GAGCTCGCCACCATGGACTATAAAGACGACGATGACAAAGAGAACATCACATCAGGATTCCTAGGACCCCT
TCT
CGTGTTACAGGCGGGGTTTTTCTTGTTGACAAGAATCCTCACAATACCGCAGAGTCTAGACTCGTGGTGGAC
TTC
TCTCAATTTTCTAGGGGGAACTACCGTGTGTCTTGGCCAAAATTCGCAGTCCCCAACCTCCAATCACTCACC
AAC
CTCTTGTCCTCCAACTTGTCCTGGTTATCGCTGGATGTGTCTGCGGCGTTTTATCATCTTCCTCTTCATCCT
GCT
GCTATGCCTCATCTTCTTGTTGGTTCTTCTGGACTATCAAGGTATGTTGCCCGTTTGTCCTCTAATTCCAGG
ATC
CTCAACAACCAGCACGGGACCATGCCGGACCTGCATGACTACC*GGTTCCGGTTCA*TGTACTAAACCAACCGA
CGG TABLE 4-continued CP-BNP Construct Exemplary Nucleotide Sequences AAATTGC*GGTTCCGGTTC*ATGTACTAAACCAACCGACGGAAATTGC*GGTTCCGGTTC*ATGTACTAAACCAAC
CGA
CGGAAATTGC*GGTTCCGGTTC*AACCGGTCAAGGAACCTCTATGTATCCCTCCTGTTGCTGTACCAAACCTTC
GGA
CGGAAATTGCACCTGTATTCCCATCCCATCATCCTGGGCTTTCGGAAAATTCCTATGGGAGTGGGCCTCAGC
CCG
TTTCTCCTGGCTCAGTTTACTAGTGCCATTTGTTCAGTGGTTCGTAGGGCTTTCCCCCACTGTTTGGCTTTC
AGT
TATATGGATGATGTGGTATTG TABLE 4-continued CP-BNP Construct Exemplary Nucleotide Sequences Gene sequence: Construct 6 (BNP 6) (SEQ ID NO: 14)
Parent (vector sequence): HBsAg small, genotype D, serotype ayw
Design:
Loop 1 and loop 2 repeats (in total trimer); in addition to the original ayw loop 1 and ayw
loop2 sequences, two adw loop 1 (dimer) and loop 2 (dimer) sequences added.
Loop 1 region (original ayw sequence in bold, and two additional adw loop 1 sequences, in
bold and highlighted). Miniloop 1 120-PCKTCTTP-127 (SEQ ID NO: 28) (dimer, serotype
adw) followed by original 120-PCRTCMTT-127 (SEQ ID NO: 55) (serotype ayw)
Loop 2 region (enlarged font):
Loop 2 original sequence 139-CTKPSDGNC-147 (SEQ ID NO: 54) (ayw) (in bold) followed by adw dimer 139-CTKPTDGNC-147 (SEQ ID NO: 34) (in bold and highlighted)
Start ATG and stop codon: enlarged font
Linker: GSGS (SEQ ID NO: 53) (underlined and italic)
FLAG-tag (underlined)
GAGCTCGCCACcATGGACTATAAAGACGACGATGACAAAGAGAACATCACATCAGGATTCCTAGGACCCCT
TCT
CGTGTTACAGGCGGGGTTTTTCTTGTTGACAAGAATCCTCACAATACCGCAGAGTCTAGACTCGTGGTGGAC
TTC
TCTCAATTTTCTAGGGGGAACTACCGTGTGTCTTGGCCAAAATTCGCAGTCCCCAACCTCCAATCACTCACC
AAC
CTCTTGTCCTCCAACTTGTCCTGGTTATCGCTGGATGTGTCTGCGGCGTTTTATCATCTTCCTCTTCATCCT
GCT
GCTATGCCTCATCTTCTTGTTGGTTCTTCTGGACTATCAAGGTATGTTGCCCGTTTGTCCTCTAATTCCAGG
ATC
CTCAACAACCAGCACGGGACCATGCAAAACCTGTACTACCCCA*GGTTCCGGATCA*CCATGCAAAACCTGTAC
TAC
CCCA*GGTTCCGGATCA*CCATGCCGGACCTGCATGACTACTGCTCAAGGAACCTCTATGTATCCCTCCTGTTG
CT
GTACCAAACCTTCGGACGGAAATTGC*GGTTCCGGTTCA*TGTACTAAACCAACCGACGGAAATTGC
*GGT*
*TCCGGTTCA*TGTACTAAACCAACCGACGGAAATTGCACCTGTATTCCCATCCCATCATCCTGGGCTTT
CGG
AAAATTCCTATGGGAGTGGGCCTCAGCCCGTTTCTCCTGGCTCAGTTTACTAGTGCCATTTGTTCAGTGGTT
CGT
AGGGCTTTCCCCCACTGTTTGGCTTTCAGTTATATGGATGATGTGGTATTGGGGGCCAAGTCTGTACAGCAT
CTT
GAGTCCCTTTTTACCGCTGTTACCAATTTTCTTTTGTCTTTGGGTATACATTTAACTCGAG Gene sequence: Construct 7 (BNP 7) (SEQ ID NO: 15)
Parent (vector sequence): HBsAg small, genotype D, serotype ayw
Design:
Loop 1, adw, dimer. 121-CKTCTTPAQGNSMFPS-136 (SEQ ID NO: 35) (in bold and highlighted)
Loop 1 original ayw, monomer. 121-PCRTCMTTAQGTSMYPS-136 (SEQ ID NO: 48) (in bold)
Start ATG and stop codon: enlarged font
Linker: GSGS (SEQ ID NO: 53) (underlined and italic)
FLAG-tag (underlined)
GAGCTCGCCACCATGGACTATAAAGACGACGATGACAAAGAGAACATCACATCAGGATTCCTAGGACCCCT
TCT
CGTGTTACAGGCGGGGTTTTTCTTGTTGACAAGAATCCTCACAATACCGCAGAGTCTAGACTCGTGGTGGAC
TTC
TCTCAATTTTCTAGGGGGAACTACCGTGTGTCTTGGCCAAAATTCGCAGTCCCCAACCTCCAATCACTCACC
AAC
CTCTTGTCCTCCAACTTGTCCTGGTTATCGCTGGATGTGTCTGCGGCGTTTTATCATCTTCCTCTTCATCCT
GCT
GCTATGCCTCATCTTCTTGTTGGTTCTTCTGGACTATCAAGGTATGTTGCCCGTTTGTCCTCTAATTCCAGG
ATC
CTCAACAACCAGCACGGGACCATGCAAAACCTGCACCACTCCAGCGCAAGGAAATTCTATGTTTCCCTCCTG
T*GG*
*TTCCGGTTCA*TGCAAAACCTGCACCACTCCAGCGCAAGGAAATTCTATGTTTCCCTCCTGT*GGTTCCGGTTC*
*A*CC
ATGCCGGACCTGCATGACTACTGCTCAAGGAACCTCTATGTATCCCTCCTGTTGCTGTACCAAACCTTCGGA
CGG
AAATTGCACCTGTATTCCCATCCCATCATCCTGGGCTTTCGGAAAATTCCTATGGGAGTGGGCCTCAGCCCG
TTT
CTCCTGGCTCAGTTTACTAGTGCCATTTGTTCAGTGGTTCGTAGGGCTTTCCCCCACTGTTTGGCTTTCAGT
TAT
ATGGATGATGTGGTATTGGGGGCCAAGTCTGTACAGCATCTTGAGTCCCTTTTTACCGCTGTTACCAATTTT
CTT
TTGTCTTTGGGTATACATTTAACTCGAG TABLE 4-continued

| CP-BNP Construct Exemplary Nucleotide Sequences |
|---|
| Gene sequence: Construct 8 (BNP 8) (Complete loop regions 120-147 ayw and adw present) (SEQ ID NO: 16)<br>Parent (vector sequence): HBsAg small, genotype D, serotype ayw<br>Design:<br>Original ayw loop in bold<br>Added adw derived loop sequence, in bold and highlighted<br>Linker: GSGS (SEQ ID NO: 53) (underlined and italic)<br>FLAG-tag (underlined)<br>GAGCTCGCCACCATGGACTATAAAGACGACGATGACAAAGAGAACATCACATCAGGATTCCTAGGACCCCT<br>TCT<br>CGTGTTACAGGCGGGGTTTTTCTTGTTGACAAGAATCCTCACAATACCGCAGAGTCTAGACTCGTGGTGGAC<br>TTC<br>TCTCAATTTTCTAGGGGGAACTACCGTGTGTCTTGGCCAAAATTCGCAGTCCCCAACCTCCAATCACTCACC<br>AAC<br>CTCTTGTCCTCCAACTTGTCCTGGTTATCGCTGGATGTGTCTGCGGCGTTTTATCATCTTCCTCTTCATCCT<br>GCT<br>GCTATGCCTCATCTTCTTGTTGGTTCTTCTGGACTATCAAGGTATGTTGCCCGTTTGTCCTCTAATTCCAGG<br>ATC<br>CTCAACAACCAGCACGGGACCATGCCGGACCTGCATGACTACTGCTCAAGGAACCTCTATGTATCCCTCCTG<br>TTG<br>CTGTACCAAACCTTCGGACGGAAATTGC*GGTTCCGGTTCA*CCATGCAAAACCTGTACTACCCCAGCGCAAGG<br>AAA<br>TTCTATGTTTCCCTCCTGCTGTTGCACTAAACCAACCGACGGAAATTGCACCTGTATTCCCATCCCATCATC<br>CTG<br>GGCTTTCGGAAAATTCCTATGGGAGTGGGCCTCAGCCCGTTTCTCCTGGCTCAGTTTACTAGTGCCATTTGT<br>TCA<br>GTGGTTCGTAGGGCTTTCCCCCACTGTTTGGCTTTCAGTTATATGGATGATGTGGTATTGGGGGCCAAGTCT<br>GTA<br>CAGCATCTTGAGTCCCTTTTTACCGCTGTTACCAATTTTCTTTTGTCTTTGGGTATACATTTAACTCGAG |

IX. CP-Peptide Therapeutic Vaccine

Based on the HBsAg CP epitopes described in Table 1, which were incorporated into CP-BNP therapeutic vaccines, alternative delivery of these epitope vaccines as pan-genotypic/serotypic cyclic peptide vaccines was also developed. The CP epitope cyclic peptides of the present technology are listed in Table 5.

TABLE 5

CP Epitope Specific Cyclised Peptides/Formulations

| | CP epitope cyclic peptide | Loop | Sequence |
|---|---|---|---|
| Cyclised Peptides (loop 1) | 1 | 1 | TCTTPAQGNSMFPSC (SEQ ID NO: 17) |
| | 2 | 1 | TCTIPAQGTSMFPSC (SEQ ID NO: 18) |
| | 3 | 1 | TCTTPAQGTSMFPSC (SEQ ID NO: 19) |
| Cyclised Peptides (loop 2) | 4 | 2 | CTKPTDGNCT (SEQ ID NO: 20) |
| | 5 | 2 | CTKPSDGNCT (SEQ ID NO: 21) |

Immunogenicity studies have shown that the lead cyclic peptide vaccine is an equimolar formulation of cyclic peptides CTKPTDGNCT (SEQ ID NO: 20) and CTKPSDGNCT (SEQ ID NO: 21), conjugated to keyhole limpet hemocyanin (KLH). Administration of this vaccine to mice was antigenic, raising an anti-HBs Ab response consistent with a CP, indicative of "clearing" anti-HBs Ab. Analysis involved ELISA (to immunizing peptides, control peptides, VLP antigen), Induced CP analysis, Immunoprecipitation, and Western blot.

X. mRNA Vaccines

In some embodiments, the present disclosure relates to the use of mRNA constructs to elicit an immune response in existing and/or persistent hepatitis B, including chronic hepatitis B (CHB). In some embodiments, the mRNA encodes for an antigenic epitope repeat region from antigenic epitopes expressed in the loop 1 and loop 2 regions of the HBsAg-S domain. In some embodiments, the mRNA encodes for BNP 1, 2, 3, 4, 5, 6, 7, or 8. In some embodiments, the mRNA encodes for a CP epitope cyclic peptide, such as those provided in Table 5.

XI. Modes of Administration and Effective Dosages

An immunogenic composition (e.g., vaccine) as disclosed herein may be administered by any of the routes conventionally used or recommended for vaccines (e.g., parenteral route), and may be in various forms (e.g., injectable liquid). Vaccines may be administered by means of a syringe or by means of a needle-free injector for intramuscular, subcutaneous, or intradermal injection.

According to the present technology, an "effective amount" of an immunogenic composition is one that is sufficient to achieve a desired biological effect. It is understood that, in some embodiments, the effective dosage will be dependent upon the age, sex, health, and weight of the recipient, kind of concurrent treatment, if any, frequency of treatment, and the nature of the effect wanted. The ranges of effective doses provided below are not intended to be limiting and represent exemplary dose ranges. Thus, in some embodiments, the dosage will be tailored to the individual subject, as is understood and determinable by one of skill in the art. The dosage of a CP-BNP, CP epitope cyclic peptide, or mRNA vaccine for a mammalian (e.g., human) adult can be from 0.01 μg to 10,000 μg, or any range or value therein. In some embodiments, the dosage can be from 0.10 μg to 10,000 μg, or any range or value therein. In some embodiments, the dosage can be from 1 μg to 10,000 μg, or any range or value therein. In some embodiments, the dosage can be from 2 μg to 10,000 μg, or any range or value therein. In some embodiments, the dosage can be from 3 μg to 10,000 μg, or any range or value therein. In some embodiments, the dosage can be from 4 μg to 10,000 μg, or any range or value therein. In some embodiments, the dosage can be from 5 μg to 10,000 μg, or any range or value therein. In some embodiments, the dosage can be from 10 μg to 10,000 μg, or any range or value therein. In some embodiments, the dosage can be from 15 μg to 10,000 μg, or any range or value therein. In some embodiments, the dosage can be from 20 μg to 10,000 μg, or any range or value therein. In some embodiments, the dosage can be from 25 μg to 10,000 μg, or any range or value therein. In some embodiments, the dosage can be from 50 μg to 10,000 μg, or any range or value therein. In some embodiments, the dosage can be from 100 μg to 10,000 μg, or any range or value therein. In some embodiments, the dosage can be from 500 μg to 10,000 μg, or any range or value therein. In some embodiments, the dosage can be from 1,000 μg to 10,000 μg, or any range or value therein. In some embodiments, the dosage can be from 5,000 μg to 10,000 μg, or any range or value therein.

XII. Therapeutic Methods

The following discussion is presented by way of example only, and is not intended to be limiting.

One aspect of the present technology includes methods of treating existing and/or persistent hepatitis B, including chronic hepatitis B (CHB) in a subject diagnosed as having or suspected as having a hepatitis B infection. In therapeutic applications, compositions or medicaments comprising the CP-BNPs, CP epitope cyclic peptides, and/or mRNA constructs of the present technology are administered to a subject suspected of, or already suffering from, a hepatitis B infection in an amount sufficient to cure, or at least partially arrest, the symptoms of the disease.

XIII. Determination of the Biological Effect of the CP-BNPs, CP Epitope Cyclic Peptides, or mRNAs of the Present Technology Where a functional cure has been achieved or will be achieved based on the results of the HBsAg immunoassay described herein, a clinician is then able to decide to cease treatment. Hence, the HBsAg immunoassay described herein can monitor treatment to determine if an individual will achieve a functional cure, determine if an individual has achieved a functional cure, and determine if an individual has achieved a cure through natural defence mechanisms.

The protocol may be varied without departing from the essence of the present technology. The critical endpoint is the determination of the fingerprint of epitopes on HBsAg which have been occupied by an individual's antibody response. Where the fingerprint of epitopes at Loop 1 and Loop 2 has been occupied, then a functional cure can be expected. Where the antibodies which have the capacity to bind to this fingerprint are present or are indicative upon exposure to HBV but HBsAg is not detectable, then a functional cure has been achieved. At that point, treatment can cease.

EXAMPLES

The following examples are provided by way of illustration only and not by way of limitation. Those of skill in the art will readily recognize a variety of non-critical parameters that could be changed or modified to yield essentially the same or similar results. The examples should in no way be construed as limiting the scope of the present technology, as defined by the appended claims.

Example 1: Development of Clearance Profile Assay

A multiplex ("Bioplex") bead-based flow cytometric platform is used to develop an HBsAg epitope assay and establish and map the HBsAg profile of epitopes which constitute the clearance profile of HBsAg epitopes (see FIG. 2). The "clearance profile of epitopes" is a profile of epitopes targeted by an individual's antibodies. When all epitopes are bound by the antibodies generated by the individual, clearance of HBsAg can be expected. The assay is derived from an assay by Lim et al. (2014) *Hepatology* 60 (1) *supplement:* 1623, 980A. Briefly, the HBsAg multiplex immunoassay comprises panels of fluorescently identified beads each conjugated to a different anti-HBs antibody which binds to HBsAg, followed by a polyclonal phycoerythrin (PE)-conjugated detection antibody. The HBsAg multiplex panels comprise monoclonal antibodies (mAbs) directed against HBsAg external loop region including the 'a' determinant, and C-terminal domain epitopes spanning residues 99-226 of HBsAg. The HBsAg epitopes are categorized into the following domains (with the monoclonal antibodies that bind to those domains): N-terminal (mAb 1); Loop 1 (mAbs 5,6, 10); Loop 2 (mAbs 7,8, 11, 12, 16, 17, 19); Loop 1/2 combinational (mAbs 13,14,15); C-terminal (mAbs 2,3,4); and conformational (mAbs 9,18). The intensity of PE associated with each bead provides a sensitive measure of antibody recognition of the specific HBsAg epitope within the sample. The epitope profile on HBsAg in comparison to the matched HBV strain backbone has been expressed as fold change in antibody binding or epitope recognition following bioinformatics data analysis. The 95% CI for the normal range of variation of epitope recognition from the reference backbone has been established as +/−0.5 fold change. A gain-of-epitope recognition corresponds to positive fold change (>0.5 fold), and negative fold changes (>−0.5 fold) correspond to a loss or reduction of epitope binding. A depiction of the assay is shown in FIG. 1.

Example 2: Selection of mAbs

The anti-HBs mAbs utilized in the HBsAg multiplex assay (FIG. 2 top panel) were selected and sourced to provide broad coverage of epitopes with reactivity against the HBsAg antigenic and C-terminal domains (residues 99-226), covering both continuous and discontinuous epitopes, and epitope regions subject to both high variability and also conserved recognition. The high level of epitope coverage provided by the mAbs enabled analysis of the HBsAg profile according to the mapped epitope availability, and reported according to epitope region: N-terminal (mAb 1); Loop 1 (mAbs 5,6,10); Loop 2 (mAbs 7,8,11,12,16,17, 19); Loop 1/2 combinational (mAbs 13,14,15); C-terminal (mAbs 2,3,4); and conformational (mAbs 9,18). Interrogation of HBV strains (genotypes A-G) identified anti-HBs mAbs which displayed conserved epitope recognition patterns (i.e., indicative of conserved HBsAg fingerprints across genotypes and serotypes), which were mAbs 3 and 4 (C-terminal), mAb 15 (Loop 1/2 combinational), and mAb 18 (conformational). The remaining anti-HBs mAbs were sensitive to variations in the HBsAg profile which are identified by altered patterns of epitope recognition between HBV strains, in comparison to the genotype A2, serotype adw2 vaccine strain.

Example 3: Optimization of Assay/Dynamics

The HBsAg profile assay was developed and optimized using HBV A2 adw2 strain HBsAg, which forms common basis of the majority of generic HBV vaccines and thus represents a relevant baseline or backbone for comparison of HBsAg epitope recognition. The HBsAg source was primarily HBsAg patient sera, confirmed by HBV sequencing as wild-type A2 adw2 (compared to consensus sequences), with confirmation using recombinant wild-type A2 adw2 HBsAg from cell culture supernatant. Initial assay development was based on two of the anti-HBs mAbs well characterized in the laboratory (including by Western blotting, Elisa, and fluorescence) for reactivity to HBsAg, which were mAbs 10 (Loop 1) and 18 (conformational). Prepared bead sets that were labeled with a concentration series of the mAbs are incubated against a series of concentrations of HBsAg. These concentrations represent standardization of HBsAg. Conditions were identified which corresponded to comfortable fluorescent readout (within the range of 10000-20000 RFU), without causing overloading and aggregation of the bead/mAb-HBsAg complexes. An assay concentration of HBsAg was determined to be approximately 16 IU/well (the standardized level), with detection of HBsAg as low as 1IU/well and up to 100 IU/well. A sample dilution series for HBsAg was incorporated in the assay of 8, 16, and 32 IU/well, to account for any slight inaccuracy in the diagnostic determination of HBsAg concentration. The optimal concentration of anti-HBs mAbs labeled to beads was optimized as the mAb concentration resulting in fluorescence reactivity with the dynamic range of the instrument (15000-18000 RFU), and this was specifically/empirically determined for each mAb. The multiplexing of the assay was built by the sequential addition of individual anti-HBs mAbs conjugated to beads, which allowed the identification of epitope competition due to partial shared epitopes by mAbs. To avoid measuring epitope competition between mAbs (i.e., record the HBsAg epitope profile correctly), three sets of multiplex anti-HBs bead/mAbs were established, as a 4plex, 5plex, and 10plex. HBsAg samples were analyzed in parallel (on the same plate) with these plexes and resulting data combined to achieve a multiplex readout of the HBsAg profile (FIG. 2 top panel).

Example 4: Assay Validation/HBsAg Profiles Across HBV Strains

The assay was developed against HBsAg A2 adw2, which corresponds to the common vaccine strain of HBV, and thus reflects the HBsAg profile of epitope recognition for the multiplexed anti-HBs mAbs in the assay. The assay was validated for both HBsAg A2 adw2 from wild-type ex vivo sera HBsAg and recombinant HBsAg from in vitro cell culture to confirm the HBsAg profile for A2 adw2, which formed a vaccine strain background for the comparison of other HBV strains (genotypes and serotypes), which may be vaccine mismatched, and for reported HBsAg variants with potential for vaccine escape (e.g., sG145R/A, sP120T/L, sD144E/A). The assay was further validated against HBsAg of different genotypes (A-G) and serotypes, sourced from both patient sera and recombinant supernatants, which established the HBsAg profile of each strain in comparison to the vaccine strain (A2 adw2) background. A reference panel of sera representative of each HBV strain was established for ongoing inclusion in the assay as control data points in study cohorts. Genotype specific variations in the HBsAg profile between the common genotypes (A, B, C, D) are apparent at Loop 1 (mAb6) and Loop 2 (mAb8) epitopes, whilst serotype at the Loop 2 (mAb7) epitope. The HBV strains which are more divergent from the vaccine strain (C4, E and F) show more exaggerated variation from the vaccine strain in their HBsAg profile of epitope recognition.

Example 5: Characterizing Clearance Profile Associated a 'Clearing' Anti-HBs Response FIG. 1 shows the application of the assay described in Example 1 to characterizing a clearance profile (CP)-associated with antibodies which result in a functional cure. The assay determines HBsAg epitope occupancy using a mAb panel wherein mAbs 5 and 6 target the consensus sequence in Loop 1 of:

$$CX_1TCX_2X_3X_4X_5QGX_6SMX_7PC \quad (SEQ\ ID\ NO: 24)$$

wherein:
$X_1$ is K or R;
$X_2$ is T or M;
$X_3$ is T, or I;
$X_4$ is P, T or L;
$X_5$ is A or V;
$X_6$ is N or T; and
$X_7$ is F or Y.

mAb 10 binds to another epitope Loop 1 within amino acids 120 to 127 of the consensus sequence:

$$PCX_8TCX_9X_{10}X_{11} \quad (SEQ\ ID\ NO: 25)$$

wherein:
$X_8$ is K or R;
$X_9$ is T or M
$X_{10}$ is T, I or S; and
$X_{11}$ is P, T or L.

mAbs 7, 8, 11, 12, 16 and 17 bind to an epitope within amino acids 137 to 147 of consensus sequence SEQ ID NO: 26 in Loop 2 wherein the consensus sequence is:

$$CCCTKPX_{12}DGNCX_{13} \quad (SEQ\ ID\ NO: 26)$$

wherein:
$X_{12}$ is T or S; and
$X_{13}$ is T or S.

It is proposed that a population of antibodies which occupy both SEQ ID NO: 24 and/or SEQ ID NO: 25 and also occupy SEQ ID NO: 26 represent a clearance profile of antibodies which indicate a functional cure.

Example 6: Predictive Biomarkers of Functional CHB Cure

FIG. 2 describes an assay which detects HBsAg with occupied epitopes (top panel) and an assay which detects HBsAg complexed to anti-HBs antibodies (lower panel). The assays employ a multiplex immunoassay which detects occupancy of epitopes at Loop 1 (consensus sequence SEQ ID NOs: 24 and 25) and at Loop 2 (consensus sequence SEQ ID NO: 26).

Example 7: HBsAg Clearance Profile in CHB Cure

Figure 3:
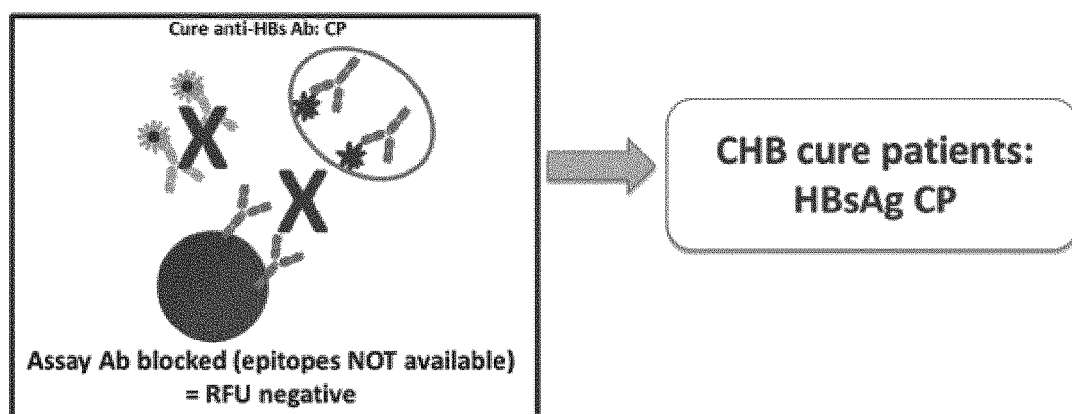
FIG. 3 is a diagrammatic representation showing CHB cure patients exhibiting an HBsAg clearance profile (CP). CHB: Chronic hepatitis B.
Figure 4:
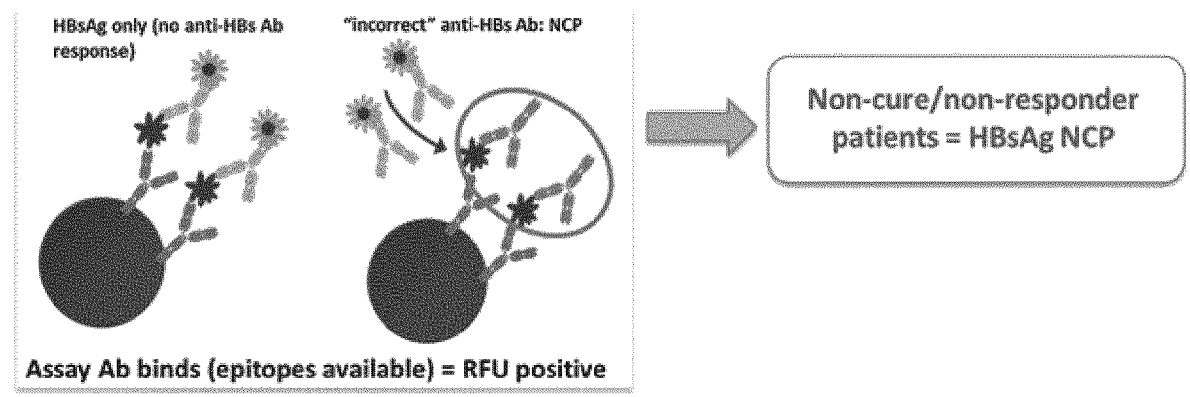
FIG. 4 is a diagrammatic representation showing non-cure/non-responder patients exhibiting an HBsAg non-clearance profile (NCP). RFU: Relative fluorescence unit.
Figure 6:
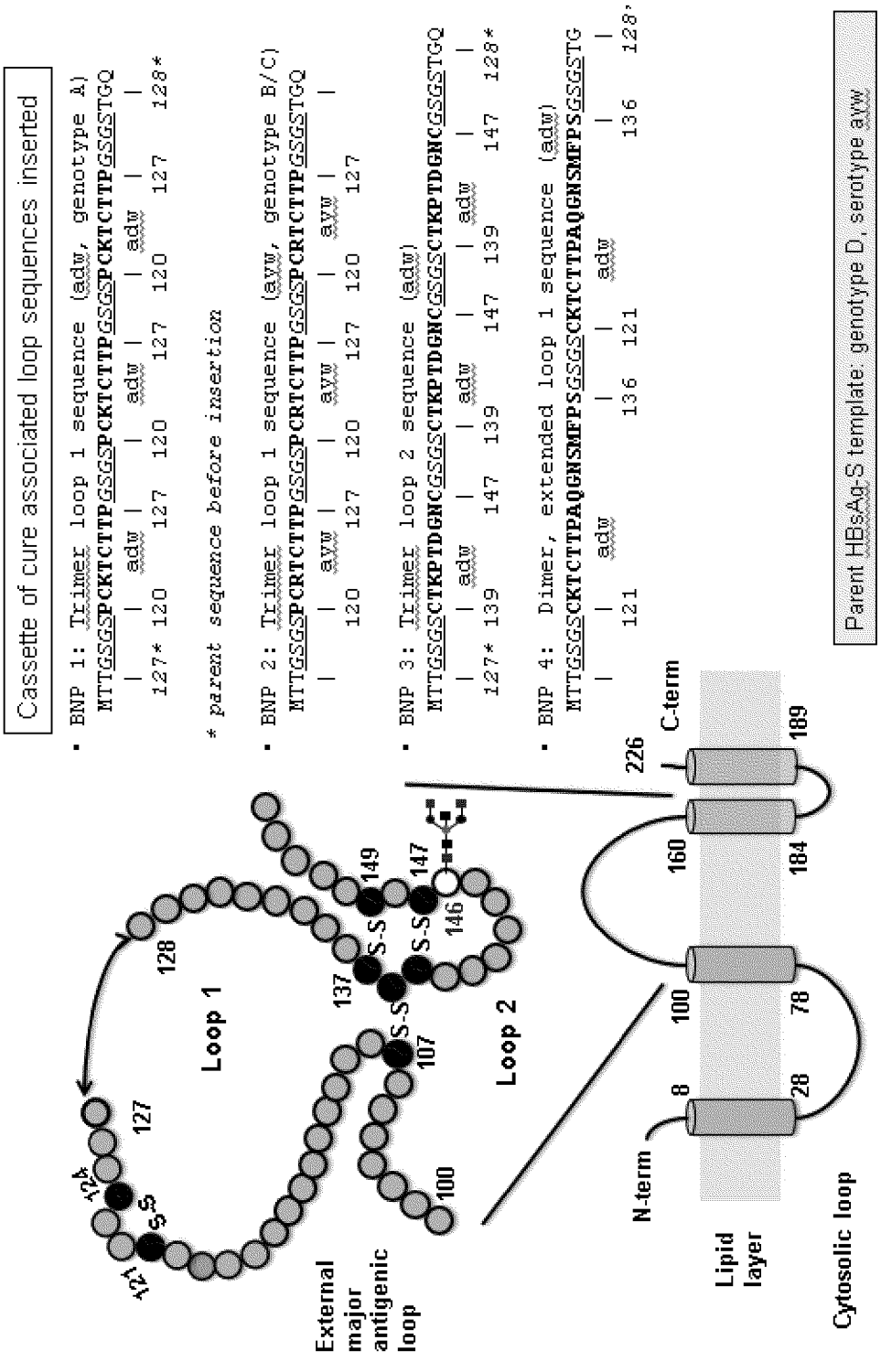
FIG. 6 is a schematic showing proposed folding of the HBsAg-S protein, 226 amino acids in length, for BNPs 1, 2, 3, and 4. The external antigenic loop region between amino acids 100 and 160 of HBsAg-S is enlarged: each amino acid is represented by a grey circle, the cysteine residues are shown as black circles, the potential —S—S— disulfide bonds highlighted. The glycosylation site (asparagine) at position 146 is shown in white, and the glycan structure indicated. The position used to insert foreign sequence is located at amino acids 127 and 128, the HBsAg-S sequence sub-type ayw is used as the parent template. Additional HBsAg-S derived antigenic sequences are inserted at position 127 and 128 into the parent template. Right panel shows the cure associated loop sequences for BNP 1, 2, 3 and 4 (SEQ ID NOs: 41-44, in order of appearance), the HBsAg-S-specific antigenic sequence is in bold, the "GSGS" linker (SEQ ID NO: 53) in italic, and underlined. BNP-1 is an 'ayw' parent template with a trimer PCKTCTTP (SEQ ID NO: 28) insert (loop1, genotype A specific, serotype adw); BNP-2 is an 'ayw' parent template with a trimer PCRTCTTP (SEQ ID NO: 33) insert (loop 1, genotype B/C, serotype ayw); BNP-3 is an 'ayw' parent template with a trimer insert of the loop 2 sequence CTKPTDGNC (SEQ ID NO: 34) (derived from serotype 'adw'); BNP-4 is an 'ayw' parent template with an insert (dimer) of the extended loop 1 sequence CKTCTTPAQGNSMFPS (SEQ ID NO: 35) (serotype 'adw').
Figure 7:
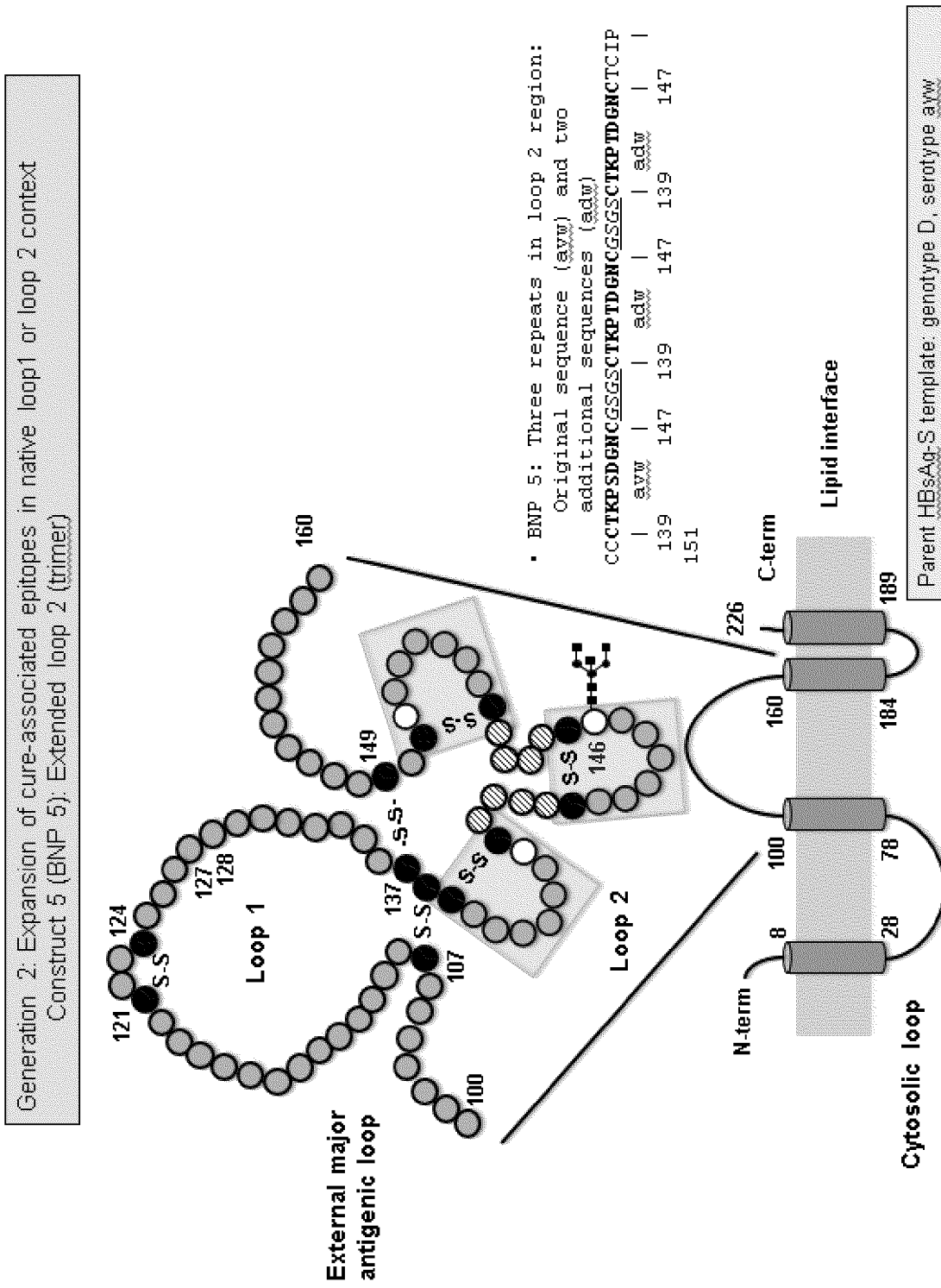
FIG. 7 is a schematic showing proposed folding of the HBsAg-S protein, 226 amino acids in length, for BNP 5. The external antigenic loop region between amino acids 100 and 160 of HBsAg-S is enlarged: each amino acid is represented by a grey circle, the cysteine residues are shown as black circles, the potential —S—S— disulfide bonds highlighted, the "GSGS" linker (SEQ ID NO: 53) by striped circles. The glycosylation site (asparagine) at position 146 is shown in white, and the glycan structure indicated. Two additional loop 2 sequences are added to the wild type loop to generate a repetitive structure. The loop 2 CTKP(T/S)TDGNC (SEQ ID NO: 36) sequence repeats are boxed. Right panel shows the sequence (SEQ ID NO: 45), the HBsAg-S-specific antigenic sequence is in bold, the "GSGS" linker (SEQ ID NO: 53) in italic, and underlined. BNP-5 is an parent 'ayw' parent template with a trimer loop 2 region. The 'ayw' loop 2 sequence is extended by two additional 'adw' loop 2 sequences.
Figure 8:
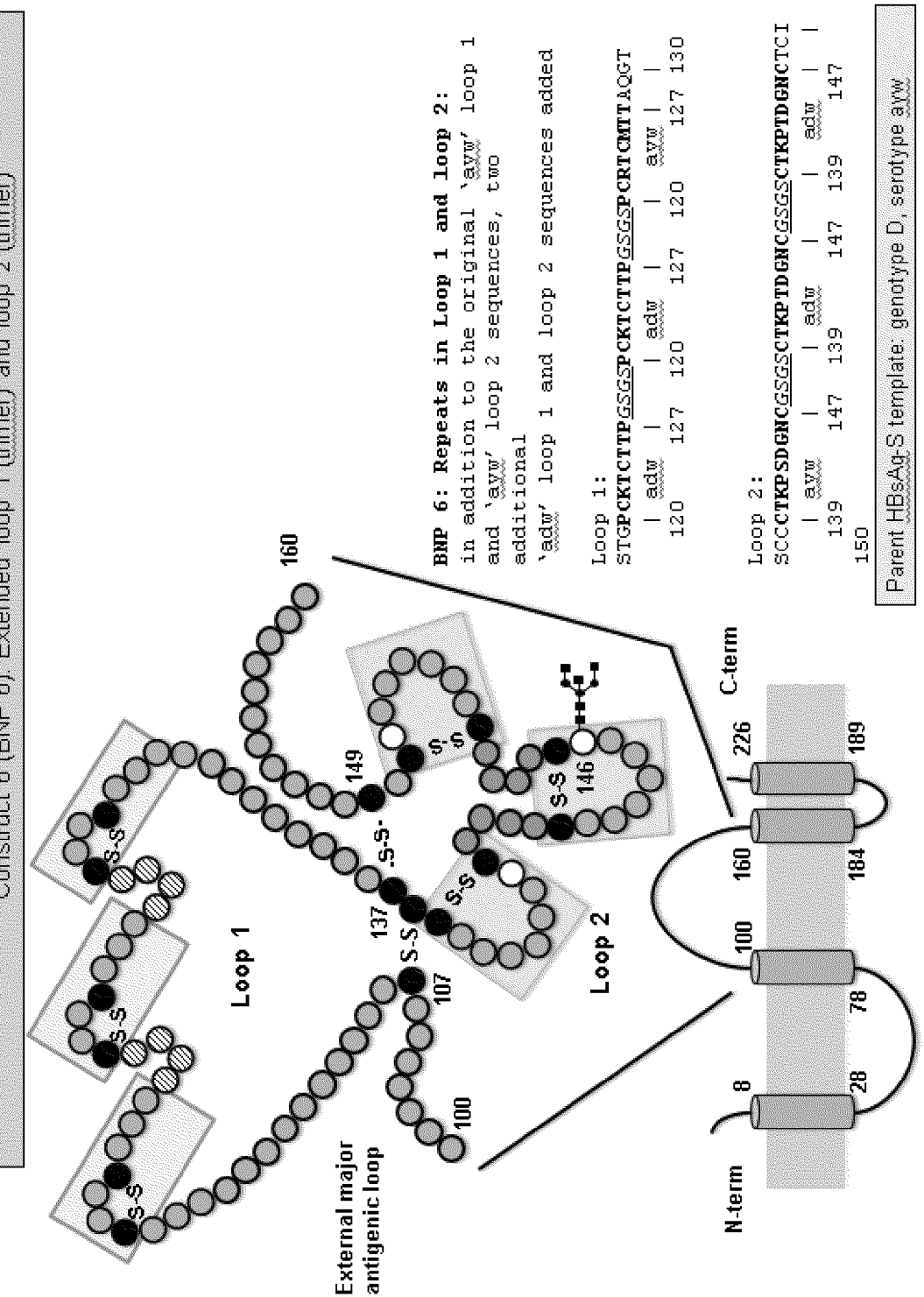
FIG. 8 is a schematic showing proposed folding of the HBsAg-S protein, 226 amino acids in length, for BNP 6. The external antigenic loop region between amino acids 100 and 160 of HBsAg-S is enlarged: each amino acid is represented by a grey circle, the cysteine residues are shown as black circles, the potential —S—S— disulfide bonds highlighted, the "GSGS" linker (SEQ ID NO: 53) by striped circles. The glycosylation site (asparagine) at position 146 is shown in white, and the glycan structure indicated. Two additional loop 1 PC(K/R)TC(T/M)TP (SEQ ID NO: 37) and loop 2 CTKP(T/S)TDGNC (SEQ ID NO: 36) sequences are added within the corresponding loop sequence. The loop 1 and loop 2 sequence repeats are boxed. Right panel shows the extended sequences (SEQ ID NOs: 46 and 47, in order of appearance), the HBsAg-S-specific antigenic sequences are in bold, the "GSGS" linker (SEQ ID NO: 53) in italic and underlined. Two additional loop 1 sequences (serotype adw) are inserted followed by the original loop 1 sequence of the parent template (serotype ayw). The original loop 2 sequence (parent serotype ayw) is followed by two inserted loop 2 sequences, serotype adw.
Figure 9:
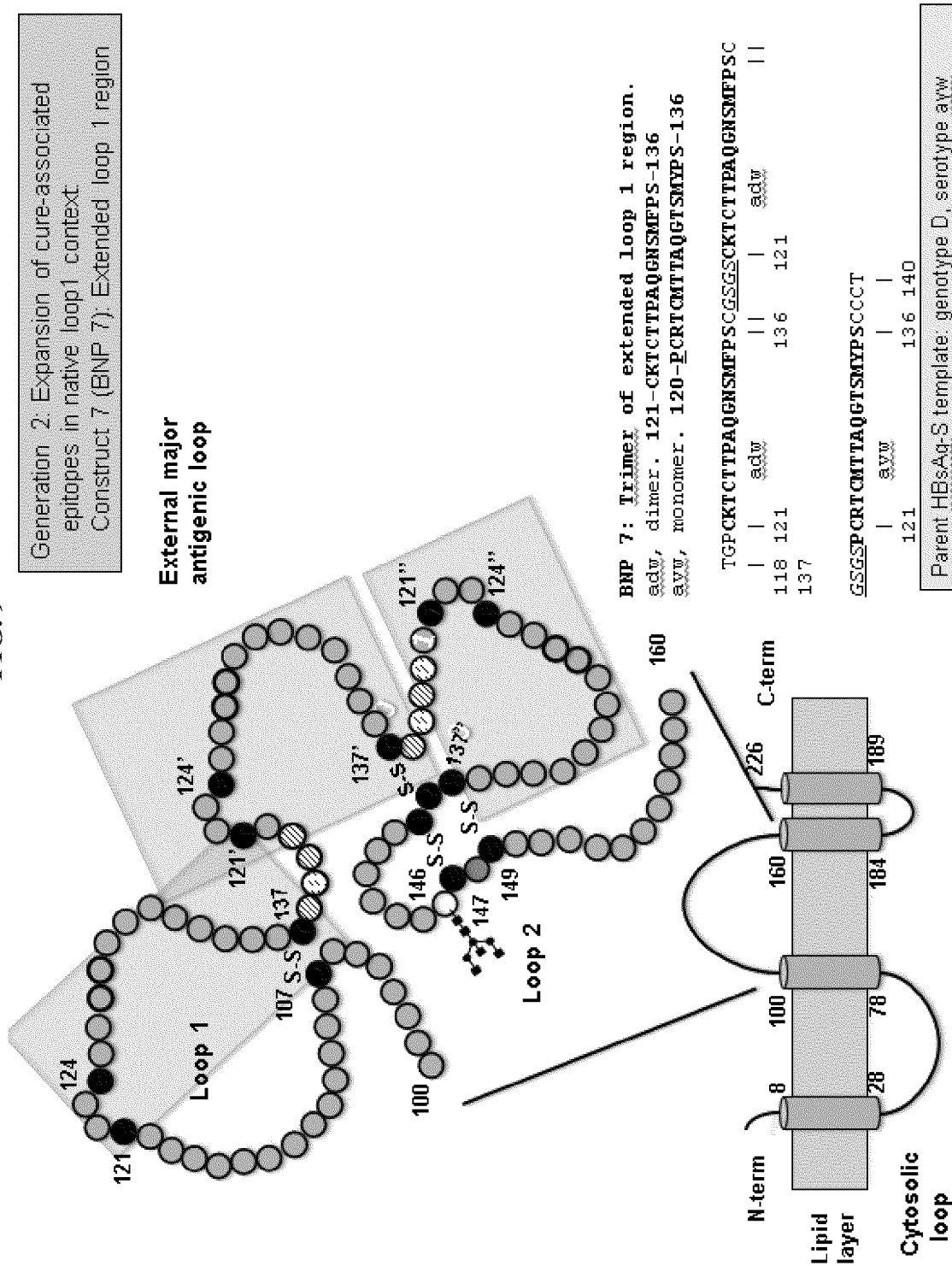
FIG. 9 is a schematic showing proposed folding of the HBsAg-S protein, 226 amino acids in length, for BNP 7. The external antigenic loop region between amino acids 100 and 160 of HBsAg-S is enlarged: each amino acid is represented by a grey circle, the cysteine residues are shown as black circles, the potential —S—S— disulfide bonds highlighted, the "GSGS" linker (SEQ ID NO: 53) by striped circles. The glycosylation site (asparagine) at position 146 is shown in white, and the glycan structure indicated. Two additional loop 1 C(K/R)TC(T/M)T(P/T)AQG(N/T)SM(F/Y)PS (SEQ ID NO: 38) sequences are added within the loop 1 sequence. The loop 1 repeats are boxed. The original amino acid positions for the wild type HBsAg-S sequence are unchanged, and the additional amino acids are marked with ' and ". Right panel shows the extended sequences (SEQ ID NOs: 52, 48, and 49, in order of appearance), the HBsAg-S-specific antigenic sequences are in bold, the "GSGS" linker (SEQ ID NO: 53) in italic and underlined. Two extended loop 1 sequences (serotype adw), amino acid sequence 121 to 136 were inserted followed by the original loop 1 sequence (serotype ayw).

FIG. 3 and FIG. 4 are diagrammatic representations showing HBsAg clearance profile (CP) in CHB cure. In FIG. 3, functional cure patients develop an antibody response that clears infection. In FIG. 4, non-cure/non-responder patients do not carry the occupied HBsAg epitopes. The term HBsAgCP means the clearance profile of HBsAg epitopes. A HBsAg-non-clearance profile is referred to as HBsAg-NCP.

Example 8: HBsAg Clearance Profile in CHB Cure

Recognition by each assay mAb for HBsAg epitopes is recorded as a fold change of recognition; positive fold change relating to enhanced or improved recognition of the HBsAg epitope, unchanged or normal range epitope recognition (within +/−0.5 fold), and reduced HBsAg epitope recognition indicated by negative fold change. An HBsAg CP is indicated by reduced HBsAg epitope recognition (e.g., due epitope occupancy) at both loop 1 and loop 2 HBsAg epitopes.

Example 9: Identification of a Predictive Clearance Profile Biomarker

HBsAg profile assay. The multiplex anti-HBs panel assay (FIG. 2, top panel) on the bioplex was originally developed with the concept of diagnostic monitoring of CHB patients for HBsAg changes. For example, the assay may be used in patients on nucleotide analog (NA) therapy where HBV DNA is undetectable but HBsAg remains positive, and in looking for the development of treatment resistance mutations, or vaccine escape variants. Additionally, the assay is useful for trying to understand the HBsAg profile and changes occurring during CHB disease phases, i.e., predictive biomarkers for CHB disease. A cohort of patients whom achieved CHB functional cure (from the Natural History cohort) are relevant to the CP biomarker identification and are further detailed below.

Results from the HBsAg profile assay led to the development of the CP biomarker (i.e., recognition of HBsAg by subsets of anti-HBs Abs in the assay). The results from these assays provided an understanding that: (a) functional cure is related to an anti-HBs response; (b) the "clearing" anti-HBs response is specifically targeting epitopes of/within loop 1 and loop 2 specific anti-HBs Abs in the assay; (c) patients have many different anti-HBs Abs, but only those targeting these both the loop 1 and loop 2 epitopes (CP epitopes) are associated with achieving functional cure; and (d) enhanced and targeted display of these CP associated epitopes drives production of CP-associated "clearing" anti-HBs Abs.

Natural History Functional Cure Cohort: Anti-HBs analysis performed. This study involved six patients with CHB identified in the St Vincent's study (Natural History Cohort) whom fulfilled the case definition of functional cure (FC). All six patients were off antiviral therapy and had become HBsAg undetectable and had successfully seroconverted with anti-HBS. All six Natural History Cohort patients were anti-HBs positive in their serum samples (following seroconversion), which were then analysed for the capability of that anti-HBs status to "induce" a FC-P (functional cure clearance profile; based on functional cure patients anti-HBs analysis and 4plex assay panel) when incubated with reference HBsAg (see FIG. 1). The FC-P was defined as a loss of epitope binding at both loop 1 and loop 2 in the external loop region including the "a" determinant of HBsAg, using four mAbs: mAb 5, mAb 6, mAb 7, and mAb 8: (mAb 5 and mAb 6 recognize epitopes in loop 1; mAb 7 and mAb 8 recognize epitopes in loop 2) (see FIG. 2, top panel). One of the six natural history patients had serum samples previously available which were still HBsAg-positive. Using 4plex anti-HBs Abs on the Bioplex platform, the HBsAg-positive sample was epitope mapped and fulfilled the case definition of the FC-profile (FC-P).

The derived HBsAg epitopes recognized by the 4plex loop 1 or loop 2 anti-HBs Abs (detailed in Table 1) have been inserted as multiple repeats into a HBsAg VLP vaccine delivery platform to generate BNP/FC-P (CP-BNP). These BNP/FC-P vaccines were prepared as either a single epitope delivery format or as multiple epitope mixtures which were administered as immunizations to mice. The resulting anti-HBS responses were analyzed for their ability to induce a FC-P when incubated with reference HBsAg, and FC-P were identified for BNP immunization mixtures covering both loop 1 and loop 2 epitopes. These BNP/FC-P immunization formulations comprised constructs detailed in Table 2. These vaccines tested to date comprised both loop 1 and loop 2 epitopes and resulted in the generation of FC-P associated antibody.

Example 10: VLP/BNP Production

The methods for protein production in mammalian cell lines and and purification via ultracentrifugation, affinity and gel filtration purification are standard protocols and described below, and in Hyakumura, et al., *Journal of Virology* 2015, 89 (22): 11312-11322 (2015).

Briefly, for the production of VLPs or BNPs, HEK293-T cells grown in Dulbecco's modified Eagle's medium, DMEM (Gibco-BRL, Grand Island, NY) supplemented with GlutaMax-1 (Gibco-BRL), 10% fetal calf serum (FCS), penicillin and streptomycin (Gibco-BRL) were transfected with expression constructs using polyethylenimine (PEI) (Polysciences, Warrington, USA) or FectoPRO (PolyPlus Transfection USA). The VLPs/BNPs were harvested from the cell culture supernatant 5-8 days post transfection. VLPs/BNPs which include an N-terminal Flag tag, were affinity purified from the collected tissue culture supernatant was affinity purified over anti-Flag affinity resin columns (CSIRO, Australia). Fusion proteins were either competitively eluted from the anti-Flag affinity column with recombinant Flag peptide (0.4mgml; CSIRO, Australia) in PBS. Affinity purified VLP/BNP preparations in PBS were then peak purified by size exclusion over Superdex 200 or Superose 6 gel filtration columns (GE Healthcare). Final VLP/BNP purified preparations were tested for Endotoxin (Endosafe Test, Charles River, USA) and spin concentrated to <1 ml using Amicon 50 kDa cut-off centrifugal concentrator devises. Alternatively, the VLPs/BNPs were purified from the collected tissue culture supernatant by spin clarification using a benchtop centrifuge, then the supernatant was transferred into an ultracentrifuge tube, underlaid with a 20% sucrose cushion, and the particles pelleted by ultracentrifugation. The supernatant was discarded, and the pelleted VLPs resuspended in STE buffer (100 mM NaCl, 10 mM Tris, pH8, 1 mM EDTA) for vaccination purposes. VLP/BNP preparation yield purity was assessed by: i) A260/280 spectra profile using a calculated VLP extinction coefficient of 37.26; ii) quantitative HBsAg serology (Elecsys HBSAG II kit; Roche); iii) SDS-PAGE followed by Coomassie staining and Western blotting (WB) with both anti-HBs and anti-Flag detection antibodies; iv) HBsAg epitope profile assay analysis on the Bioplex platform (in-house assay); and, v) standard ELISA techniques with detection by anti-HBs antibodies (in-house assay).

Example 11: CP-BNP Epitope Retention

Figure 11:
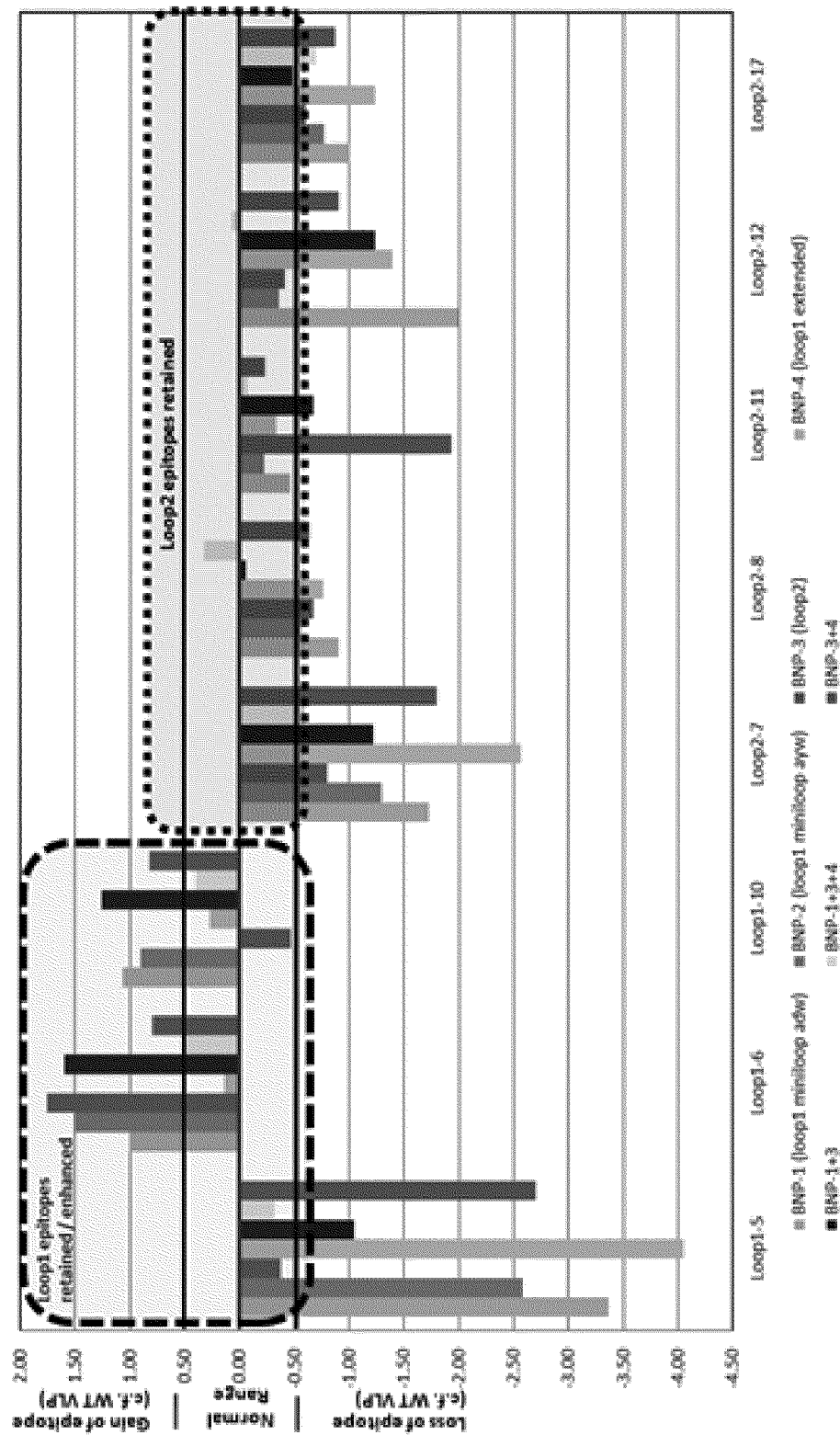
FIG. 11 is a chart showing the HBsAg epitope profile (bioplex platform) analysis of CP-BNP 1, 2, 3, and 4 preparations and CP-BNP 1+3, 1+3+4, and 3+4 formulations. The CP-BNPs incorporate displayed loop 1 (CP-BNP 1, 2, 4) or loop 2 (CP-BNP 3) specific "clearing" epitope inserts to induce targeted "clearing" anti-HBS antibody responses following immunization. HBsAg epitope profile analysis indicates that epitopes across both loop 1 and loop 2 are retained (within normal range of +/−0.5 fold) and/or enhanced (>0.5 fold) in all tested CP-BNP preparations and formulations, indicating antigenicity for the target "clearing" epitopes are displayed correctly and intact, with the strongest/broadest epitope retention achieved in the BNP formulations.

Following BNP production and purification, and quality assurance analysis for yield and purity of the BNP preparations, the CP-BNP were analysed for HBsAg epitope profile (Bioplex platform) as individual BNP preparations and also as BNP formulations to assess loop 1 and loop 2 epitope presentation retention (i.e., loop 1 and loop 2 epitopes are displayed or presented) as appropriate to antigenicity on delivery. As shown in FIG. 11, CP-BNP formulations retain the epitope inserts of the present technology.

Example 12: CP Epitope Cyclic Peptide Production

Cyclised CP Epitope Peptides. Cyclised peptides were designed to mimic the identified loop 1 and loop 2 target "clearing" epitopes within HBsAg, similar to the CP epitope inserts delivered in the CP-BNPs. Sequence variations within these epitopes exist dependant on naturally occurring HBV genotype and HBsAg serotype variations, and multiple cyclic peptides were designed based on this consideration, generating pan-genotypic/pan-serotypic equimolar formulations of loop 1 or loop 2 CP epitope cyclised peptides for delivery as immunizing antigens in immunogenicity studies for the development of CP-associated "clearing" anti-HBs antibodies. The designed peptides were ordered for production by Mimotopes (Australia) with N-terminal free amine, C-terminal free acid, cyclised by disulphide bonds at native sequence cysteine residues. Production was to a purity of >85% by HPLC and determined by mass spectrometry profile analysis. Cyclised peptide was coupled via a glutaraldehyde linker to either KLH (keyhole limpet hemocyanin) for immunization or to BSA (bovine serum albumin) for screening assays. Exemplary cyclic peptides of the present technology are listed in Table 5 above.

An immunogenicity study to generate CP-associated anti-HBs comprised immunization with loop 1 mix cyclic peptide or loop 2 mix cyclic peptide formulations administer to n=2 BALB/c and n=2 C57/B6 mice for each peptide formulation. Mice were immunized with 3×2 ug doses of peptide mix.

Harvested pre-fusion sera was screened by standard ELISA protocols for antibody responses specific to recombinant HBsAg (VLP) and to HBsAg loop 1 or loop 2 peptides cyclised peptides (individual peptides and pooled peptide formulations formulation). Sera was also analysed for the generation of anti-HBs antibody induced CP profile assay analysis on the Bioplex platform (in-house assay). This data was used to inform which mice should be selected for spleen harvest and fusion to develop monoclonal anti-HBs specific antibodies.

Post-fusion supernatant was screened initially by standard ELISA protocols for antibody responses specific to recombinant HBsAg (VLP) and to loop 1 and loop 2 cyclised peptides (individual peptides and pooled peptide formulations formulation). Clone supernatants were further analysed for detection of HBsAg following SDS-PAGE and Western Blot, to determine affinity for linear epitopes. The clone supernatants were analysed for the generation of anti-HBs antibody induced CP profile assay analysis on the Bioplex platform (in-house assay), with comparison to pre-incubation pan-genotypic/serotypic HBsAg. This data was used to determine which clones should be selected for further rounds of monoclonal antibody development, with analysis of clone supernatants at each round, and including analysis of final selected monoclonal anti-HBS antibodies (Table 6; FIG. 12).

TABLE 6

Post-fusion clone selection for monoclonal antibody line production

| | ELISA (peptide loop 1) | ELISA (peptide loop 2) | ELISA (VLP) | Western blot | Induced CP |
|---|---|---|---|---|---|
| Loop 1 peptide project | 1C1, 4G4, 9E4, 8H4[#] | 8H4[#] | 1C1[#, 4G4#], 9E4[#] | 1C1, 2E12 | 4F1, 6A7, 8E6 |
| Loop 2 peptide project | 2F4, 6F12, 5D4, 10D9 | 2F4, 6F12, 5D4, 4G2, 3D2, 10D9 | 2F4, 6F12, 5D4, 3D2, 10D9 | 5B6[#] | 4G2, 6H12, 7F4, 10D9, 2F4 |

Selected clones in bold and underlined
[#]denotes weak response/reactivity

Example 13: CP-BNP and CP Epitope Cyclic Peptide Immunogenicity Study

This example demonstrates the immunogenicity of the CP-BNPs and CP epitope cyclic peptides of the present technology. The immunogenicity of CP-BNPs and CP-BNP formulations displaying target loop 1, loop 2, or loop 1 & 2 "clearance" epitopes (see Table 2 above), were assessed by immunization of BALB/c strain mice. CP-BNPs 1-4 and formulations thereof (in comparison to WT-BNP background control) were assessed in a first round BNP immunogenicity study. These will be reassessed alongside assessment of CP-BNPs 5-8 and formulations thereof in a second immunogenicity study.

Immunogenicity study #1 incorporated CP-BNPs 1-4 and formulations as indicated in Table 2 (in comparison to WT-BNP and PBS placebo controls), whilst immunogenicity study IMM001 repeated assessment performed in the original study and additionally assessed performance of CP-BNPs 5-8 and formulations 1+3+4 and 5+7. Six week old BALB/c mice (up to 5 per arm) were immunised with 3×2μg doses of purified CP-BNP antigen at fortnightly intervals. Bleeds were taken prior to each antigen administration and then following immunisation at weekly intervals for 5 weeks. Mice were sacrificed at the final time point and terminal bleed collected. Sera harvested from each bleed time point was analysed to investigate the Anti-HBs antibody response to CP-BNP immunisation by: i) anti-HBs antibody titres (IU/L) using diagnostic serology tests (Elecsys Anti-HBs kit, Roche); ii) standard ELISA methodology for detection of WT-VLP or HBsAg loop1 or loop2 peptides; and, iii) Anti-HBs antibody induced CP profile assay analysis on the Bioplex platform (in-house assay). The loop1 and loop2 reactivity reported in this table is reporting analysis of the CP-BNPs or formulations by HBsAg profile assay, to determine retained display of the HBsAg CP epitope/s identified as associated with clearance (i.e. target epitopes of a "clearing" anti-HBs response).

Figure 13A:
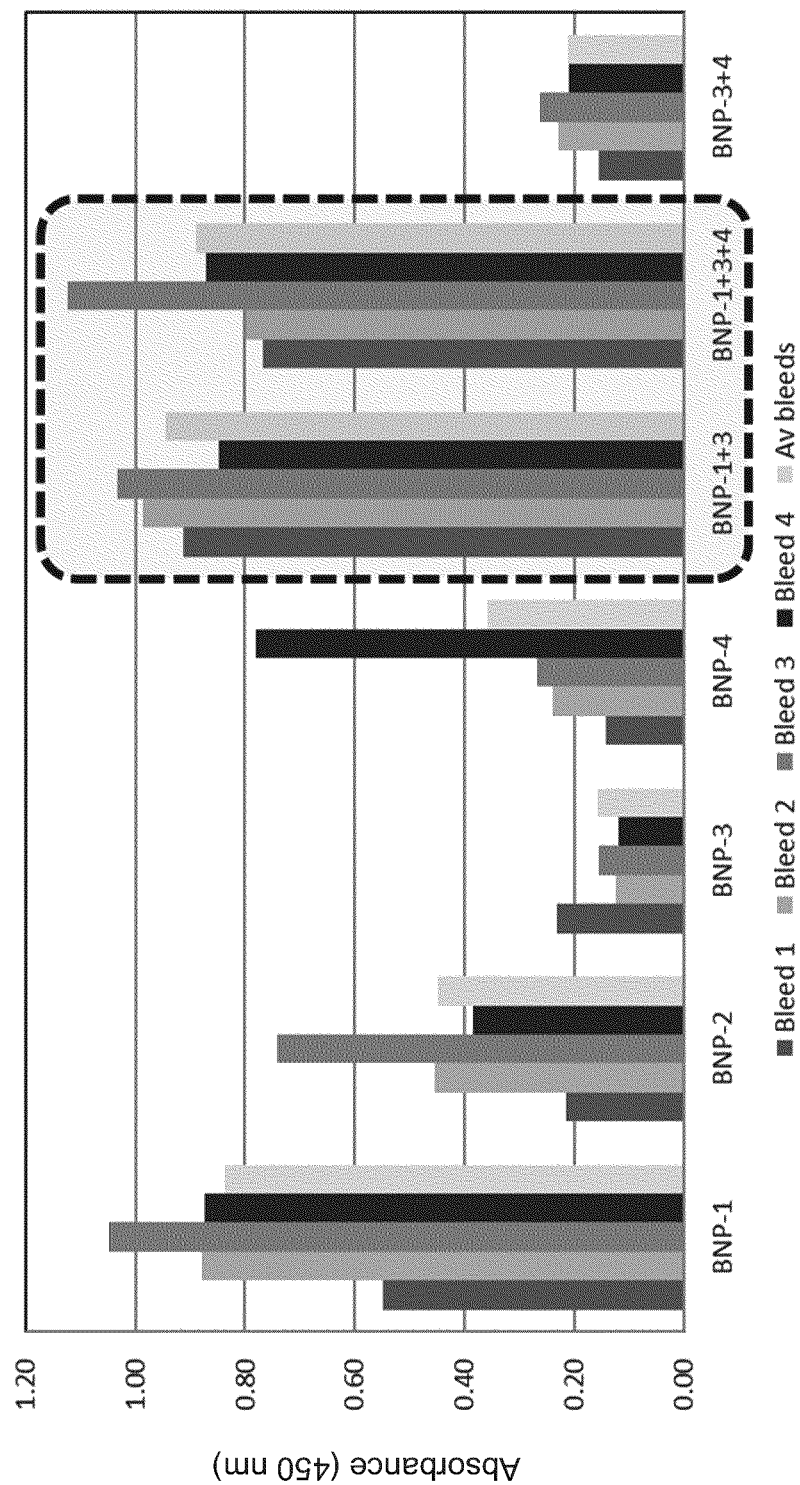
Figure 13C:
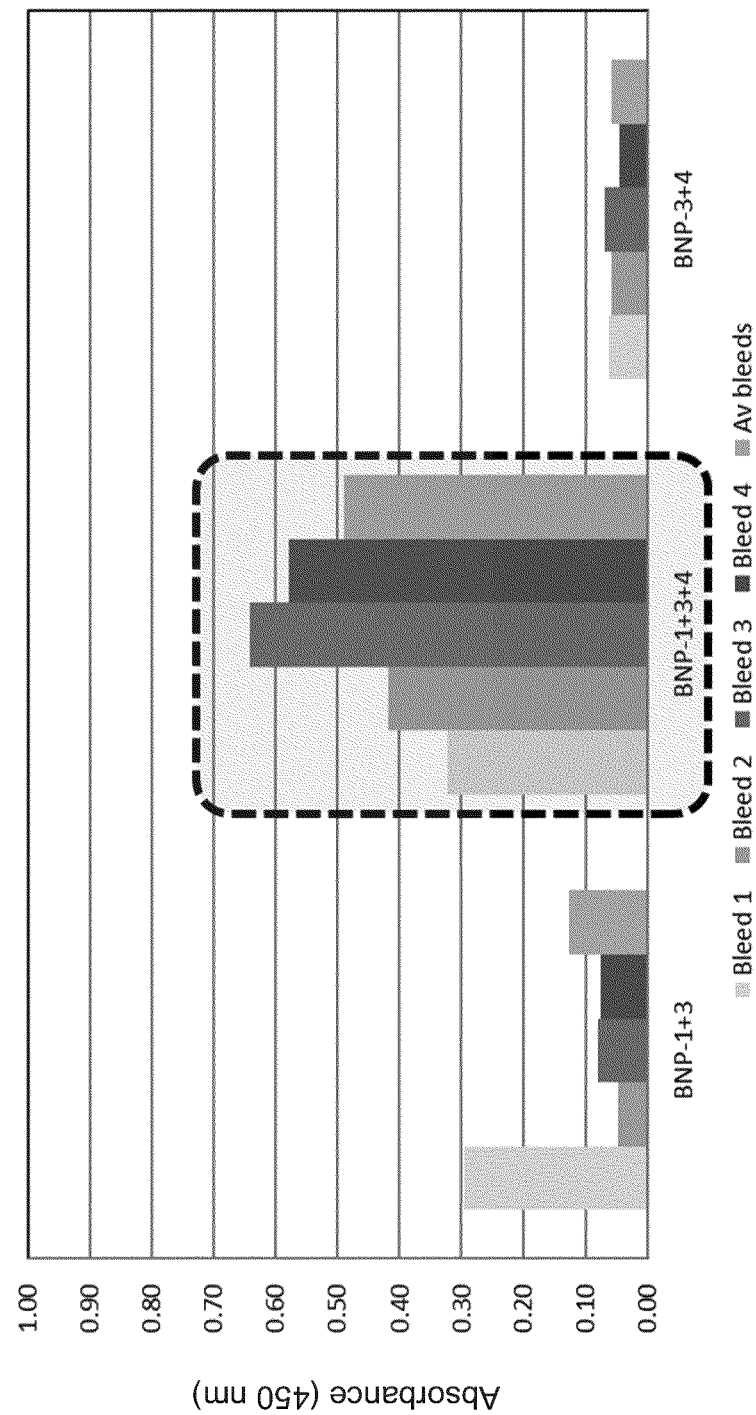
Figure 13D:
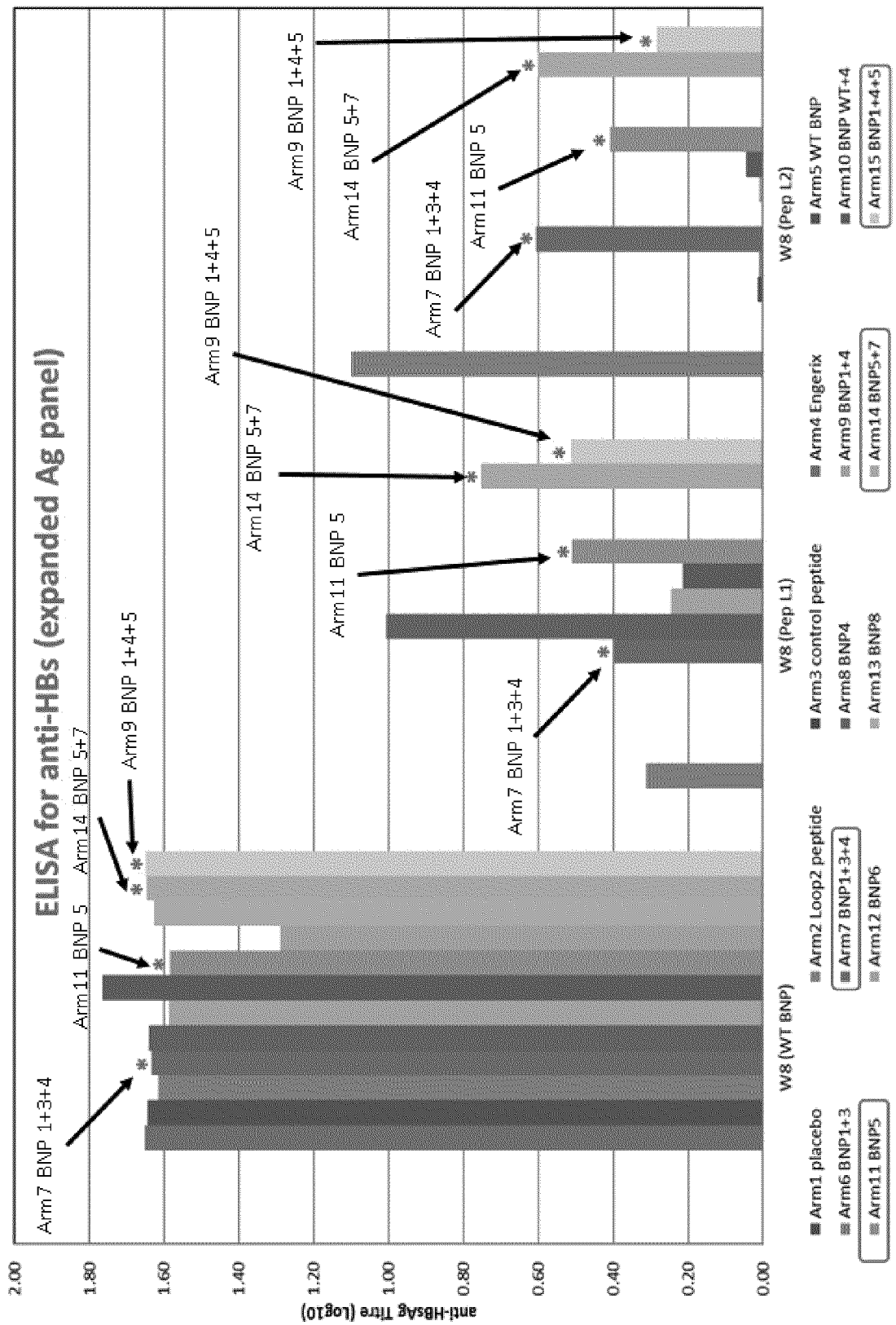

FIG. 13A shows the anti-HBs antibody immunogenicity response for CP-BNP preparations and formulations. FIG. 13B and FIG. 13C show the loop 1 and loop 2, respectively, anti-HBs antibody immunogenicity responses for the CP epitope cyclic peptides. FIG. 13D reports the anti-Hbs reactivity for WT-BNP, loop1 peptide and loop2 peptide antigens. Collectively, these results show that the CP-BNPs and CP epitope cyclic peptides of the present technology elicit HBV-specific immune responses, and are useful in methods of inducing the production of anti-HBS.

Example 14: CP-BNPs Induce a CHB Clearance Profile

This example demonstrates that the CP-BNPs of the present technology are capable of inducing a clearance profile in immunized subjects.

Figure 14:
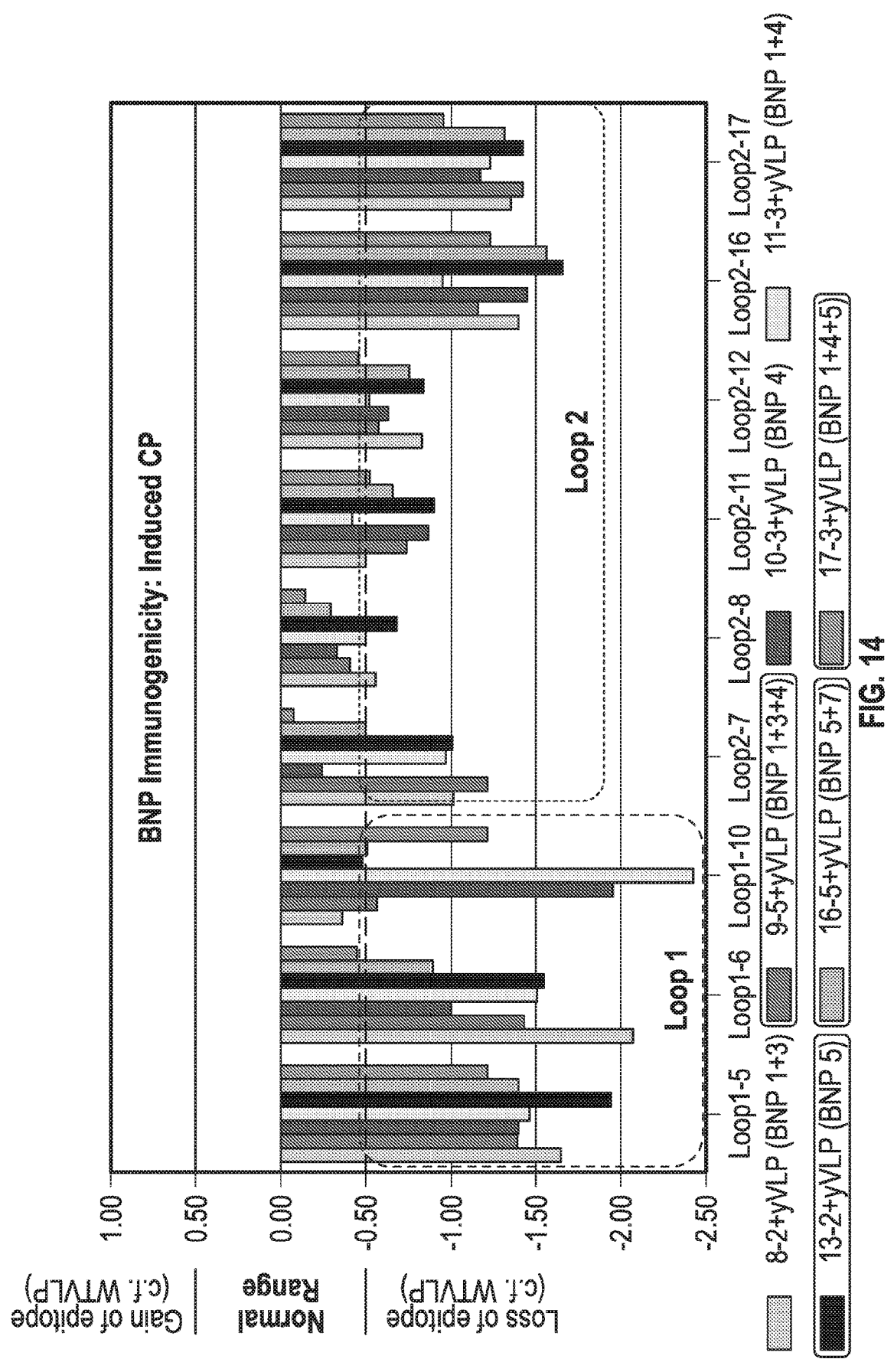

The terminal bleed sera following n=3 immunization schedule with the CP-BNP preparations (CP-BNP 1-8) and formulations (CP-BNP 1+3, 1+3+4, 1+4, WT+4, 5+7 or 1+4+5) were analysed for anti-HBs antibody profile. The results shown in FIG. 14 demonstrate that the CP-BNPs of the present technology induce a clearance profile (e.g., loss of epitope recognition at both loop 1 and loop 2 epitopes). Accordingly, these results demonstrate that compositions comprising the CP-BNPs of the present technology are useful in methods of treating chronic hepatitis B.

Example 15: mRNA Encoding CP-BNPs and CP Epitope Cyclic Peptides Induce a CHB Clearance Profile This example will demonstrate that the mRNAs encoding CP-BNPs and CP epitope cyclic peptides of the present technology are capable of inducing a clearance profile in immunized subjects.

Figure 15A:
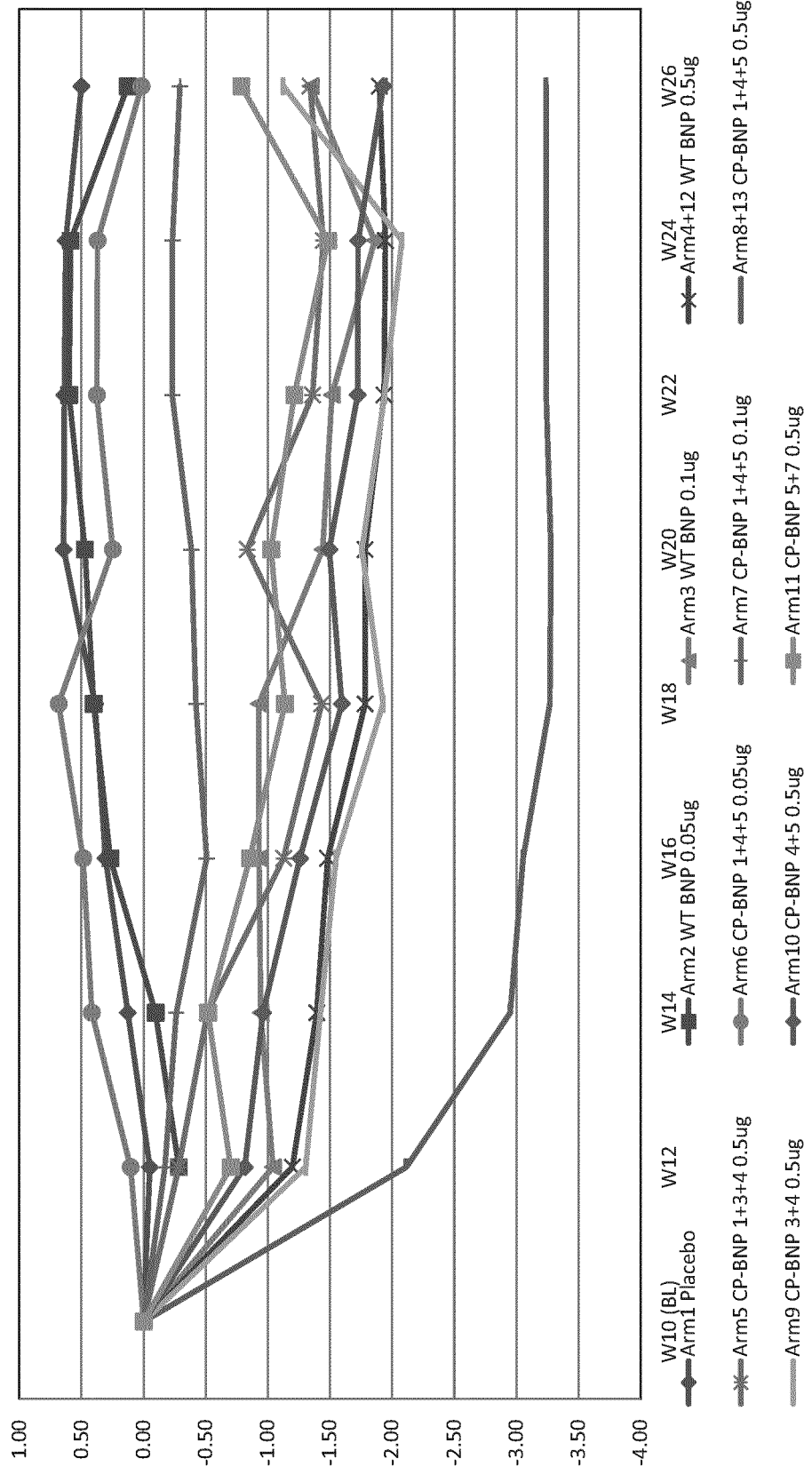
Figure 15B:
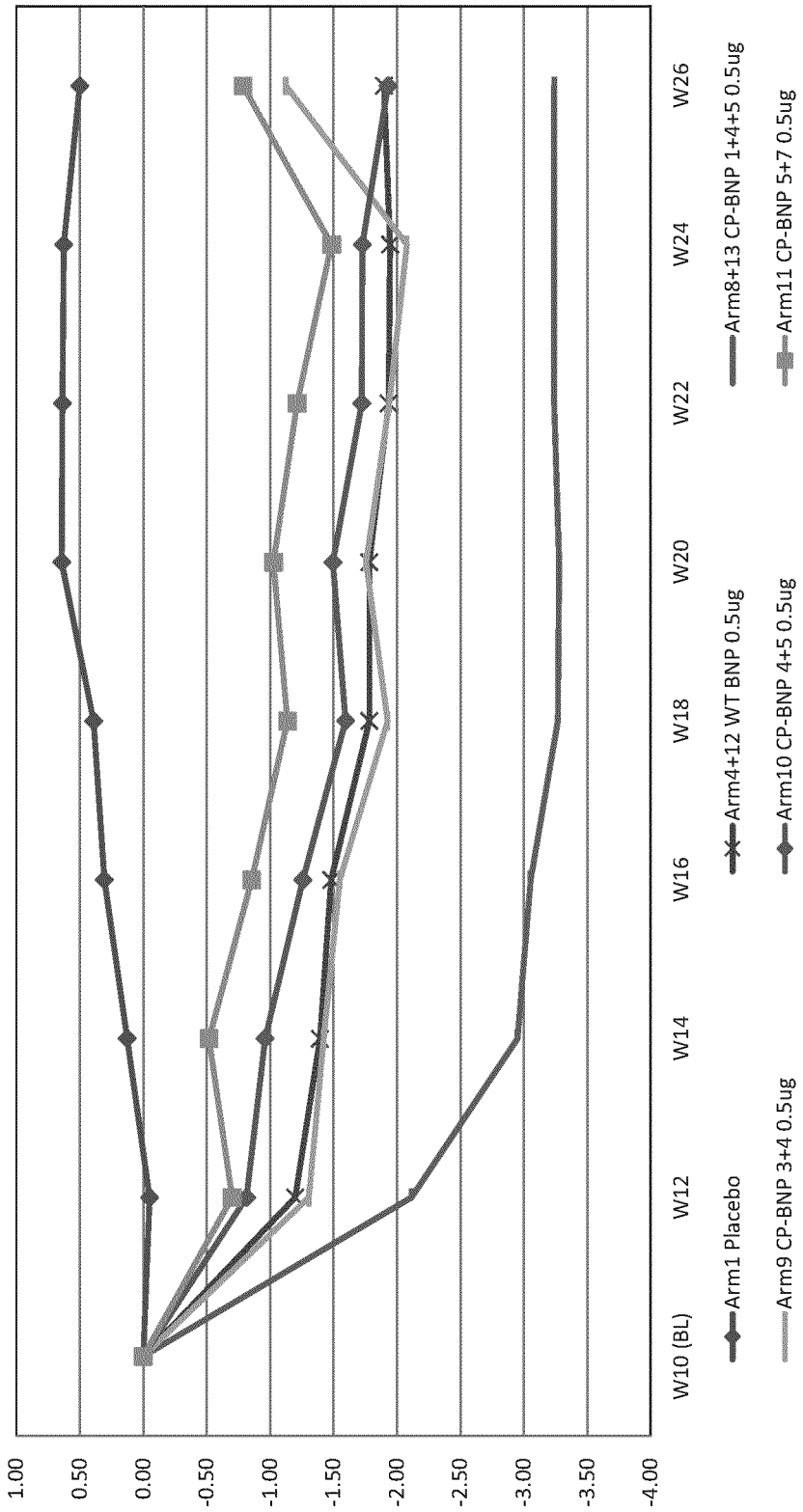

Six week old BALB/c mice (5 per arm) are immunized with 3×2µg doses of purified mRNA encoding CP-BNPs or CP epitope cyclic peptides at fortnightly intervals. Bleeds are taken prior to each antigen administration and then following immunization at weekly intervals for 5 weeks. Mice are sacrificed at the final time point and terminal bleed collected. Sera harvested from each bleed time point is analysed to investigate the anti-HBS antibody response to CP-BNP immunization by: i) anti-HBs antibody titres (IU/L) using diagnostic serology tests (Elecsys Anti-HBs kit, Roche); ii) standard ELISA methodology for detection of WT-VLP or HBsAg loop 1 or loop 2 peptides; and, iii) anti-HBs antibody induced CP profile assay analysis on the Bioplex platform (in-house assay).

The results will show that the mRNA constructs of the present technology induce a clearance profile (e.g., loss of epitope recognition at both loop 1 and loop 2 epitopes) in immunized mice. Accordingly, these results will demonstrate that compositions comprising the mRNA constructs of the present technology are useful in methods of treating chronic hepatitis B.

Example 16: CP-BNPs Reduce HBV DNA and HBsAg Levels in a Chronic Hepatitis B (CHB) Murine Model Materials and Methods for production of test vaccine candidates (CP-BNP 1, 3, 4, 5, 7) for testing in the murine (HB model. Plasmids containing HBsAgS-specific cDNA inserts (WT or various inserts as described in Table 3 and Table 4) were cloned into pCAGGS (with an N-terminal FLAG tag) and used to transfect HEK293T cells using polyethylenimine (PEI) as described previously (Longo, 2013). Functional HBsAgS proteins including chimeric HBsAgS proteins with inserted additional sequences assemble into secretion competent virus-like particles, bio-nanoparticles (BNPs). Five days post transfection, cell culture medium was harvested and centrifuged to remove cellular debris. The cell culture medium was centrifuged at high speed (ultra-centrifugation) over a 20% sucrose cushion to pellet and to partially purify the BNPs, then re-suspended in sodium chloride (NaCl)-Tris-EDTA (STE) buffer. Further purification of the BNPs was performed by ultracentrifugation using a gradient of sucrose (20-50%) in STE. Fractions containing VLPs were collected, pooled (as needed), buffer exchanged and concentrated in PBS (Hyakumura, 2015; Cheong, 2009; Patzer, 1986) and stored at −80° C. until use. HBsAg VLPs were confirmed by ELISA or western blot as previously described.

Murine CHB model. The CBA/caJ CHB mouse model was developed by hydrodynamic injection HDI) of an HBV replicon (pAAV/HBV1.2), which allows for the delivery of DNA into hepatocytes through an intravenous injection in to the tail vein (Kim, 2013; Yang, 2002; Huang, 2006). This mode of in vivo transfection was necessary because hepatitis B virus (HBV) does not naturally infect mice. A single HDI of a plasmid containing replication-competent HBV DNA induced stable HBV depending on the used mouse strain (for CBA mice persisted >6 months with liver specific HBV viral marker production (up to 32 weeks)). Long-term expression of HBV in the carrier mice does not cause liver damage, which is evidenced by normal levels of an indicator for liver damage (alanine aminotransferase, ALT). After the HDI, HBV DNA was measured in the mouse serum to confirm that HBV persistence was established. Mice with a persistent HBV were then used for immunization studies to test for the ability of chimeric BNPs with clearance profile-specific epitope repeats (CP-BNP) to induce a therapeutic immune response able to interfere and/or clear the HBV from the liver.

Following establishment of chronic hepatitis B (approximately week 10), groups of 6-8 CBA/caJ mice were treated with placebo (adjuvant control), control particles (Engerix B (marketed HBV vaccine manufactured in yeast cells), wild type BNP (WT-BNP])) or test vaccine candidates (CP-BNP 1-7, in various combinations at equimolar ratios with final concentrations as listed in FIGS. 15A-15C and 16A-16C). The treatment schedule included a mixture of different chimeric BNPs adjuvanted with aluminum hydroxide. Three doses of vaccine were given subcutaneously with 2 weeks between doses. Submandibular bleeds were performed every 2 weeks out to 26 weeks post-HDI, with testing to determine serum HBV DNA load (Sitnik, 2010) and HBsAg levels (per manufacturer's recommended protocol; qHBsAg Elecsys).

Murine CHB model results—HBV DNA levels. The HBV DNA level results described below are shown in FIGS. 15A-15C. Placebo (arm 1) did not significantly change HBV DNA levels throughout the duration of the study. WT-BNP was dosed at 0.05 (arm 2), 0.1 (arm 3) or 0.5 (arm 4 and 12) μg. The WT-BNP at 0.05 μg (arm 2) dose had no effect on HBV DNA levels, while the 0.1 (arm 3) or 0.5 (arm 4 and 12) μg doses displayed a dose dependent decrease in HBV DNA levels. The combination of CP-BNP 1+4+5 at 0.5 μg (arms 8 and 13) displayed the fastest and steepest decline in HBV DNA with sustained effects starting from W12 (two weeks after the first dose) through the end of the study (W26). The greatest decrease was observed with CP-BNP 1+4+5 at 0.5 μg, displaying a 3 log reduction in HBV DNA relative to baseline at W10 and also at least 2 log reduction in HBV DNA relative to WT-BNP at the same dose starting from W12 with maximum decreases observed starting at W14 (>3 log reduction). Using doses less than 0.5 μg, CP-BNP 1+4+5 also displayed a dose dependence decrease in HBV DNA, but the lower doses of 0.05 (arm 6) or 0.1 (arm 7) μg had higher HBV DNA relative to the same doses of WT-BNP. Other combinations of CP-BNPs were also tested in this model and found to be less efficacious than CP-BNP 1+4+5. For example, combination of CP-BNP 1+3+4 at 0.5 μg and reduced combinations (CP-BNP 3+4 (arm 9), CP-BNP 4+5 (arm 10), CP-BNP 5+7 (arm 11)) also declined in HBV DNA levels, but did so at a slower rate and less absolute decline with >1 log reduction achieved starting at W12 and maintained throughout the duration of the study. The data represented in FIGS. 15A-15C are also shown in tabular format as individual, means, and mean changes from baseline in Tables 7, 8, and 9, respectively.

TABLE 7

| | W10 (BL) | W12 | W14 | W16 | W18 | W20 | W22 | W24 | W26 |
|---|---|---|---|---|---|---|---|---|---|
| Arm1 Placebo | 5.62 | 5.12 | 5.44 | 5.62 | 5.65 | 5.85 | 5.73 | 5.69 | 5.66 |
| | 5.84 | 5.60 | 6.03 | 6.08 | 6.17 | 6.64 | 6.08 | 6.06 | 6.49 |
| | 6.29 | 5.90 | 5.68 | 6.09 | 6.30 | 6.71 | 6.57 | 6.57 | 6.28 |
| | 4.84 | 5.60 | 5.85 | 6.04 | 6.13 | 6.24 | 6.96 | 6.96 | 6.38 |
| | 5.81 | 5.62 | 5.85 | 6.14 | 6.28 | 6.51 | 6.42 | 6.43 | 6.32 |
| | 6.23 | 6.50 | 6.54 | 6.50 | 6.44 | 6.54 | 6.70 | 6.69 | 6.50 |
| Arm2 WT BNP 0.05 ug | 5.75 | 5.57 | 5.88 | 6.10 | 6.42 | 6.54 | 6.87 | 6.87 | 6.58 |
| | 5.73 | 5.50 | 5.48 | 5.96 | 6.13 | 6.16 | 6.00 | 5.98 | 5.82 |
| | 5.49 | 5.05 | 5.22 | 5.56 | 5.54 | 5.59 | 5.66 | 5.61 | 5.24 |
| | 6.35 | 5.93 | 6.26 | 6.60 | 6.81 | 6.91 | 6.84 | 6.84 | 6.51 |
| | 5.68 | 5.55 | 5.88 | 5.93 | 6.31 | 6.46 | 6.44 | 6.43 | 4.36 |
| | 6.36 | 6.05 | 6.05 | 6.81 | 6.56 | 6.53 | 7.14 | 7.14 | 7.61 |
| Arm3 WT BNP 0.1 ug | 6.03 | 5.82 | 6.14 | 6.37 | 6.29 | 6.53 | 6.73 | 6.73 | 6.21 |
| | 5.92 | 6.01 | 6.19 | 6.53 | 6.64 | | | | |
| | 5.09 | 5.00 | 5.00 | 4.62 | 4.47 | 4.35 | 3.84 | 2.48 | 5.06 |
| | 5.13 | 2.48 | 2.48 | 2.32 | 2.48 | 2.48 | 2.48 | 2.48 | 2.48 |
| | 4.82 | 2.48 | 2.48 | 2.52 | 2.48 | 2.48 | 2.48 | 2.48 | 2.48 |
| Arm4 WT BNP 0.5 ug | 5.95 | 4.10 | 3.00 | 3.02 | 2.48 | 2.48 | 2.48 | 2.48 | 2.48 |
| | 6.02 | 2.48 | 2.48 | 2.53 | 2.48 | 2.48 | 2.48 | 2.48 | 2.48 |
| | 5.28 | 2.48 | 2.48 | 2.53 | 2.48 | 3.65 | | | |
| | 6.05 | 5.83 | 5.77 | 6.69 | 6.64 | 6.83 | 6.72 | 6.71 | 6.56 |
| | 6.26 | 5.65 | 5.91 | 6.51 | 6.27 | 5.83 | 5.50 | 5.43 | 5.50 |
| | 5.39 | 5.25 | 5.50 | 5.91 | 5.95 | 6.38 | | | |
| Arm5 CP-BNP 1 + 3 + 4 0.5 ug | 5.99 | 5.42 | 5.12 | 4.07 | 3.21 | 2.48 | 2.90 | 2.48 | 3.73 |
| | 4.52 | 4.33 | 4.42 | 2.89 | 2.48 | 5.37 | | | |
| | 5.92 | 5.98 | 5.95 | 5.73 | 6.10 | 6.49 | 6.69 | 6.68 | 6.43 |
| | 5.98 | 5.90 | 5.80 | 3.57 | 2.16 | 2.48 | 2.48 | 2.48 | 2.48 |
| | 5.91 | 4.78 | 2.47 | 3.37 | 2.48 | 2.48 | 2.48 | 2.48 | 2.48 |
| | 5.92 | 5.66 | 6.27 | 6.28 | 6.77 | 6.62 | 7.22 | 7.22 | 6.75 |
| | 5.75 | 5.95 | 6.37 | 6.20 | 6.77 | 8.24 | | | |
| Arm6 CP-BNP 1 + 4 + 5 0.05 ug | 5.60 | 5.74 | 6.02 | 6.16 | 6.41 | 6.34 | 6.55 | 6.54 | 6.19 |
| | 5.99 | 5.87 | 6.22 | 6.19 | 6.69 | 6.66 | 6.95 | 6.95 | 6.37 |
| | 6.06 | 6.27 | 6.50 | 6.63 | 6.96 | 6.86 | 7.13 | 7.13 | 6.30 |
| | 4.70 | 5.13 | 5.18 | 5.47 | 4.94 | 2.48 | 2.48 | 2.48 | 2.48 |
| | 5.45 | 5.52 | 5.96 | 5.97 | 6.06 | 5.96 | 5.93 | 5.91 | 5.18 |
| | 6.05 | 6.06 | 6.38 | 6.34 | 6.81 | 6.74 | 6.71 | 6.71 | 6.51 |
| | 5.64 | 5.63 | 6.15 | 6.14 | 6.40 | 6.20 | 6.38 | 6.37 | 6.57 |
| Arm7 CP-BNP 1 + 4 + 5 0.1 ug | 5.64 | 5.61 | 5.87 | 6.18 | 6.09 | 6.24 | 6.37 | 6.36 | 6.56 |
| | 5.96 | 5.43 | 4.82 | 3.45 | 2.48 | 2.48 | 2.48 | 2.48 | 3.41 |
| | 4.37 | 4.30 | 2.48 | 2.40 | 2.48 | 2.48 | 2.48 | 2.48 | 2.48 |
| | 6.27 | 6.02 | 6.55 | 6.37 | 6.58 | 6.81 | 6.93 | 6.93 | 6.12 |
| | 6.06 | 6.16 | 6.61 | 6.34 | 6.73 | 6.78 | 7.33 | 7.33 | 6.55 |
| | 6.11 | 5.90 | 6.36 | 6.30 | 6.79 | 6.89 | 6.77 | 6.77 | 7.37 |
| | 6.43 | 6.21 | 6.30 | 6.24 | 6.74 | 6.46 | 6.87 | 6.86 | 6.31 |
| Arm8 CP-BNP 1 + 4 + 5 0.5 ug | 5.53 | 2.48 | 3.31 | 2.48 | 2.48 | 2.48 | 2.48 | 2.48 | 2.48 |
| | 5.99 | 5.82 | 2.48 | 2.48 | 2.48 | 2.48 | | | |
| | 5.98 | 2.47 | 3.01 | 2.97 | 2.48 | 2.48 | 2.48 | 2.48 | 2.48 |
| | 6.62 | 2.48 | 2.48 | 2.88 | 2.48 | 2.97 | 2.48 | 2.48 | 2.48 |
| | 6.69 | 2.48 | 2.48 | 2.57 | 2.48 | 2.48 | 2.48 | 2.48 | 2.48 |
| | 5.57 | 4.00 | 2.48 | 3.33 | 2.48 | 1.73 | 2.48 | 2.48 | 2.48 |
| | 6.17 | 2.26 | 2.48 | 2.48 | 2.48 | 2.48 | | | |
| Arm9 CP-BNP 3 + 4 0.5 ug | 5.86 | 4.12 | 3.61 | 2.55 | 2.48 | 2.48 | 2.48 | 2.48 | 2.48 |
| | 5.71 | 5.96 | 6.21 | 6.49 | 6.35 | 6.49 | 6.40 | 6.39 | 5.87 |
| | 5.84 | 3.99 | 3.71 | 3.53 | 2.51 | 3.24 | 2.23 | 2.48 | 4.96 |
| | 5.67 | 3.34 | 2.48 | 3.15 | 2.48 | 2.48 | 2.48 | 2.48 | 4.09 |
| | 6.01 | 5.56 | 6.09 | 6.16 | 6.28 | 6.32 | 6.81 | 6.81 | 6.43 |
| | 5.66 | 2.48 | 2.54 | 2.48 | 2.48 | 2.48 | 2.48 | 2.48 | 2.48 |
| | 5.38 | 5.55 | 5.53 | 4.93 | 4.08 | 4.35 | 3.68 | 2.48 | 5.95 |
| Arm10 CP-BNP 4 + 5 0.5 ug | 5.65 | 5.53 | 3.56 | 2.48 | 2.48 | 2.48 | 2.48 | 2.48 | 3.12 |
| | 5.96 | 5.99 | 6.00 | 6.05 | 5.84 | 6.42 | 5.06 | 4.83 | 2.48 |
| | 5.64 | 5.38 | 5.47 | 5.30 | 2.48 | 2.48 | 2.21 | 2.48 | 2.48 |
| | 4.96 | 2.48 | 3.02 | 2.48 | 2.48 | 2.48 | 2.48 | 2.48 | 2.48 |
| | 4.68 | 3.06 | 2.48 | 2.48 | 2.48 | 2.48 | 2.48 | 2.48 | 2.48 |
| | 5.90 | 5.40 | 5.58 | 5.37 | 5.82 | 5.79 | 5.64 | 5.59 | 6.15 |
| | 5.88 | 5.14 | 5.84 | 5.72 | 5.96 | 6.11 | 6.28 | 6.27 | 6.00 |

TABLE 7-continued

Individual HBV DNA data.

| | W10 (BL) | W12 | W14 | W16 | W18 | W20 | W22 | W24 | W26 |
|---|---|---|---|---|---|---|---|---|---|
| Arm11 CP-BNP 5 + 7 0.5 ug | 4.57 | 2.38 | 3.01 | 2.41 | 2.50 | 2.70 | 2.60 | 2.48 | 4.39 |
| | 5.33 | 5.23 | 5.77 | 5.59 | 5.57 | 5.39 | 5.18 | 5.02 | 5.07 |
| | 5.16 | 4.80 | 5.27 | 4.81 | 2.21 | 2.87 | 2.48 | 2.48 | 2.48 |
| | 5.95 | 5.55 | 3.74 | 2.48 | 2.48 | 2.48 | 2.48 | 2.48 | 2.48 |
| | 5.71 | 4.90 | 5.82 | 5.99 | 6.25 | 6.29 | 6.71 | 6.71 | 6.66 |
| | 5.93 | 5.70 | 5.64 | 5.42 | 5.55 | 5.44 | 5.18 | 5.02 | 5.10 |
| | 4.38 | 3.58 | 4.16 | 4.37 | 4.52 | 4.69 | 3.93 | 2.48 | 5.36 |
| Arm12 WT-BNP 0.5 ug | 6.20 | 5.86 | 5.96 | 2.48 | 2.48 | 2.48 | | | |
| | 6.25 | 5.95 | 4.62 | 4.41 | 4.59 | 4.60 | | | |
| | 6.13 | 5.65 | 6.45 | 6.31 | 3.77 | 2.48 | 2.48 | 2.48 | 2.48 |
| | 5.72 | 2.48 | 2.48 | 3.07 | 2.48 | 2.48 | 2.48 | 2.48 | 2.48 |
| | 4.90 | 4.27 | 2.38 | 2.48 | 2.48 | 2.48 | 2.48 | 2.48 | 3.53 |
| | 5.70 | 5.51 | 6.12 | 6.17 | 6.40 | 6.33 | 6.50 | 6.49 | 5.90 |
| Arm13 CP-BNP 1 + 4 + 5 0.5 ug | 5.72 | 5.18 | 2.48 | 2.43 | 2.48 | 2.48 | 2.48 | 2.48 | 2.48 |
| | 5.20 | 4.79 | 4.86 | 2.92 | 2.48 | 2.23 | | | |
| | 5.60 | 3.59 | 2.48 | 2.48 | 2.34 | 2.47 | 2.48 | 2.48 | 2.48 |
| | 5.35 | 3.49 | 2.48 | 2.48 | 2.23 | 2.48 | | | |
| | 4.46 | 3.03 | 2.48 | 2.59 | 2.48 | 2.48 | 2.48 | 2.48 | 2.48 |
| | 5.42 | 4.75 | 2.48 | 2.53 | 2.48 | 2.47 | 2.48 | 2.48 | 2.48 |

TABLE 8

Mean HBV DNA data.

| | Mean Values | | | | | | | | | | | | |
|---|---|---|---|---|---|---|---|---|---|---|---|---|---|
| Arms | W2 | W4 | W6 | W8 | W10 (BL) | W12 | W14 | W16 | W18 | W20 | W22 | W24 | W26 |
| Arm1 Placebo | 6.21 | 6.34 | 6.31 | 5.73 | 5.77 | 5.72 | 5.90 | 6.08 | 6.16 | 6.41 | 6.41 | 6.40 | 6.27 |
| Arm2 WT BNP 0.05 ug | 6.01 | 6.18 | 6.11 | 5.66 | 5.89 | 5.61 | 5.80 | 6.16 | 6.29 | 6.36 | 6.49 | 6.48 | 6.02 |
| Arm3 WT BNP 0.1 ug | 5.81 | 5.78 | 5.96 | 5.64 | 5.40 | 4.36 | 4.46 | 4.47 | 4.47 | 3.96 | 3.88 | 3.54 | 4.05 |
| Arm4 + 12WT BNP 0.5 ug | 6.07 | 6.07 | 6.14 | 5.71 | 5.82 | 4.62 | 4.43 | 4.34 | 4.04 | 4.04 | 3.89 | 3.88 | 3.92 |
| Arm5 CP-BNP 1 + 3 + 4 0.5 ug | 6.01 | 6.14 | 6.19 | 5.65 | 5.71 | 5.43 | 5.20 | 4.59 | 4.28 | 4.88 | 4.35 | 4.27 | 4.37 |
| Arm6 CP-BNP 1 + 4 + 5 0.05 ug | 6.23 | 6.35 | 6.35 | 5.83 | 5.64 | 5.75 | 6.06 | 6.13 | 6.32 | 5.89 | 6.02 | 6.01 | 5.66 |
| Arm7 CP-BNP 1 + 4 + 5 0.1 ug | 6.11 | 6.31 | 6.32 | 5.76 | 5.83 | 5.66 | 5.57 | 5.33 | 5.41 | 5.45 | 5.60 | 5.60 | 5.54 |
| Arm8 + 13 CP-BNP 1 + 4 + 5 0.5 ug | 6.04 | 6.23 | 6.26 | 5.82 | 5.71 | 3.60 | 2.76 | 2.66 | 2.45 | 2.44 | 2.48 | 2.48 | 2.48 |
| Arm9 CP-BNP 3 + 4 0.5 ug | 6.04 | 6.11 | 6.08 | 5.71 | 5.73 | 4.43 | 4.31 | 4.18 | 3.81 | 3.98 | 3.79 | 3.65 | 4.61 |
| Arm10 CP-BNP 4 + 5 0.5 ug | 5.90 | 5.92 | 5.85 | 5.55 | 5.53 | 4.71 | 4.56 | 4.27 | 3.93 | 4.03 | 3.80 | 3.80 | 3.60 |
| Arm11 CP-BNP 5 + 7 0.5 ug | 6.00 | 5.96 | 6.04 | 5.50 | 5.29 | 4.59 | 4.77 | 4.44 | 4.15 | 4.27 | 4.08 | 3.81 | 4.50 |

TABLE 9

Mean Changes from Baseline HBV DNA data.

| | Mean Changes from Baseline (W10) | | | | | | | | |
|---|---|---|---|---|---|---|---|---|---|
| Arms | W10 (BL) | W12 | W14 | W16 | W18 | W20 | W22 | W24 | W26 |
| Arm1 Placebo | 0.00 | −0.05 | 0.13 | 0.31 | 0.39 | 0.64 | 0.64 | 0.63 | 0.50 |
| Arm2 WT BNP 0.05 ug | 0.00 | −0.28 | −0.10 | 0.27 | 0.40 | 0.47 | 0.60 | 0.59 | 0.13 |
| Arm3 WT BNP 0.1 ug | 0.00 | −1.04 | −0.94 | −0.93 | −0.93 | −1.44 | −1.52 | −1.86 | −1.34 |
| Arm4 + 12 WT BNP 0.5 ug | 0.00 | −1.20 | −1.39 | −1.48 | −1.78 | −1.78 | −1.93 | −1.95 | −1.90 |
| Arm5 CP-BNP 1 + 3 + 4 0.5 ug | 0.00 | −0.28 | −0.51 | −1.13 | −1.43 | −0.83 | −1.36 | −1.45 | −1.34 |
| Arm6 CP-BNP 1 + 4 + 5 0.05 ug | 0.00 | 0.10 | 0.42 | 0.49 | 0.68 | 0.25 | 0.38 | 0.37 | 0.02 |
| Arm7 CP-BNP 1 + 4 + 5 0.1 ug | 0.00 | −0.17 | −0.26 | −0.51 | −0.42 | −0.38 | −0.23 | −0.23 | −0.29 |
| Arm8 + 13 CP-BNP 1 + 4 + 5 0.5 ug | 0.00 | −2.11 | −2.95 | −3.05 | −3.27 | −3.28 | −3.24 | −3.24 | −3.24 |
| Arm9 CP-BNP 3 + 4 0.5 ug | 0.00 | −1.30 | −1.42 | −1.55 | −1.93 | −1.76 | −1.94 | −2.08 | −1.12 |
| Arm10 CP-BNP 4 + 5 0.5 ug | 0.00 | −0.81 | −0.96 | −1.26 | −1.60 | −1.49 | −1.72 | −1.73 | −1.93 |
| Arm11 CP-BNP 5 + 7 0.5 ug | 0.00 | −0.70 | −0.52 | −0.85 | −1.14 | −1.03 | −1.21 | −1.48 | −0.79 |

Figure 16A:
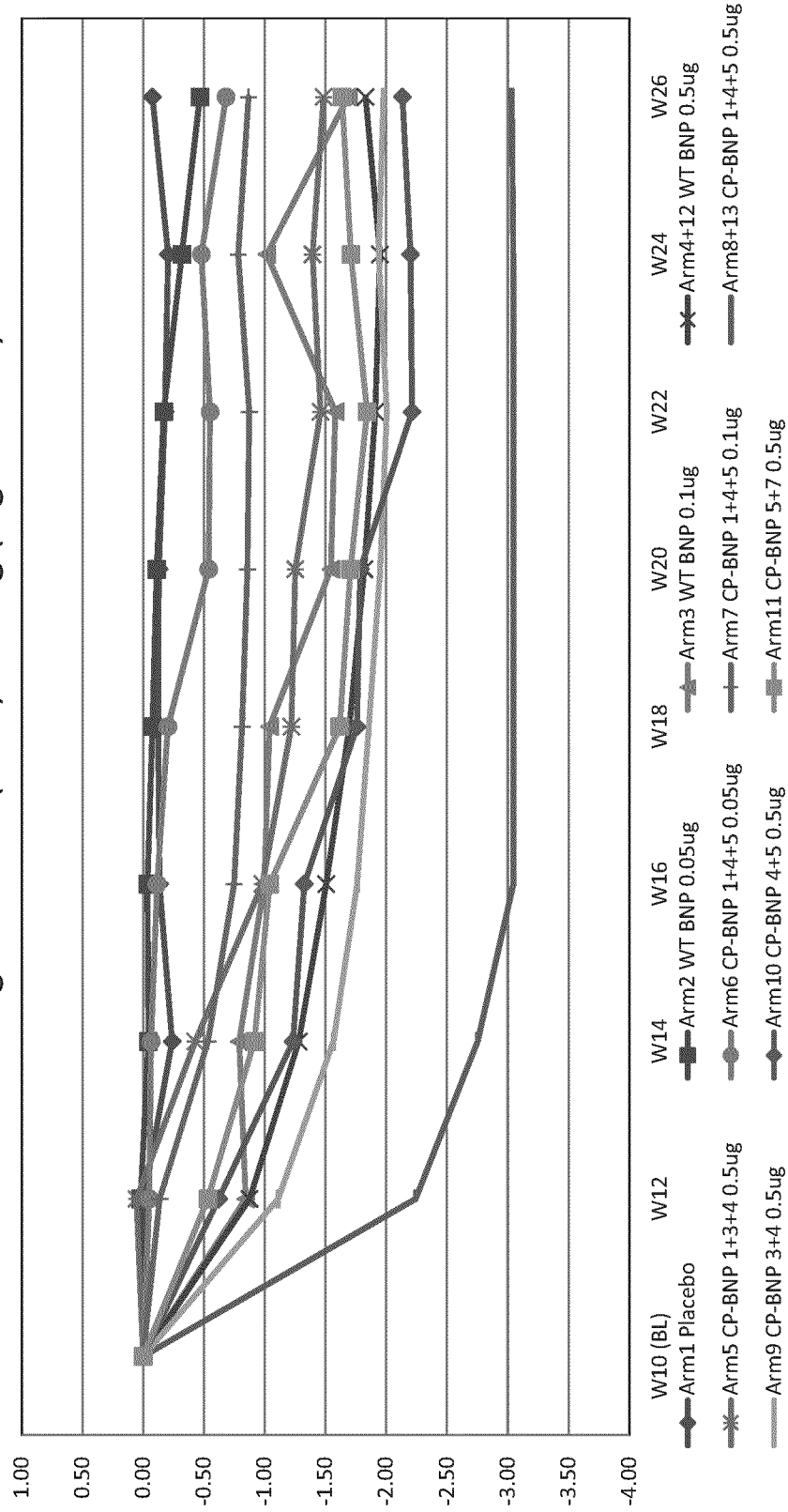
Figure 16C:
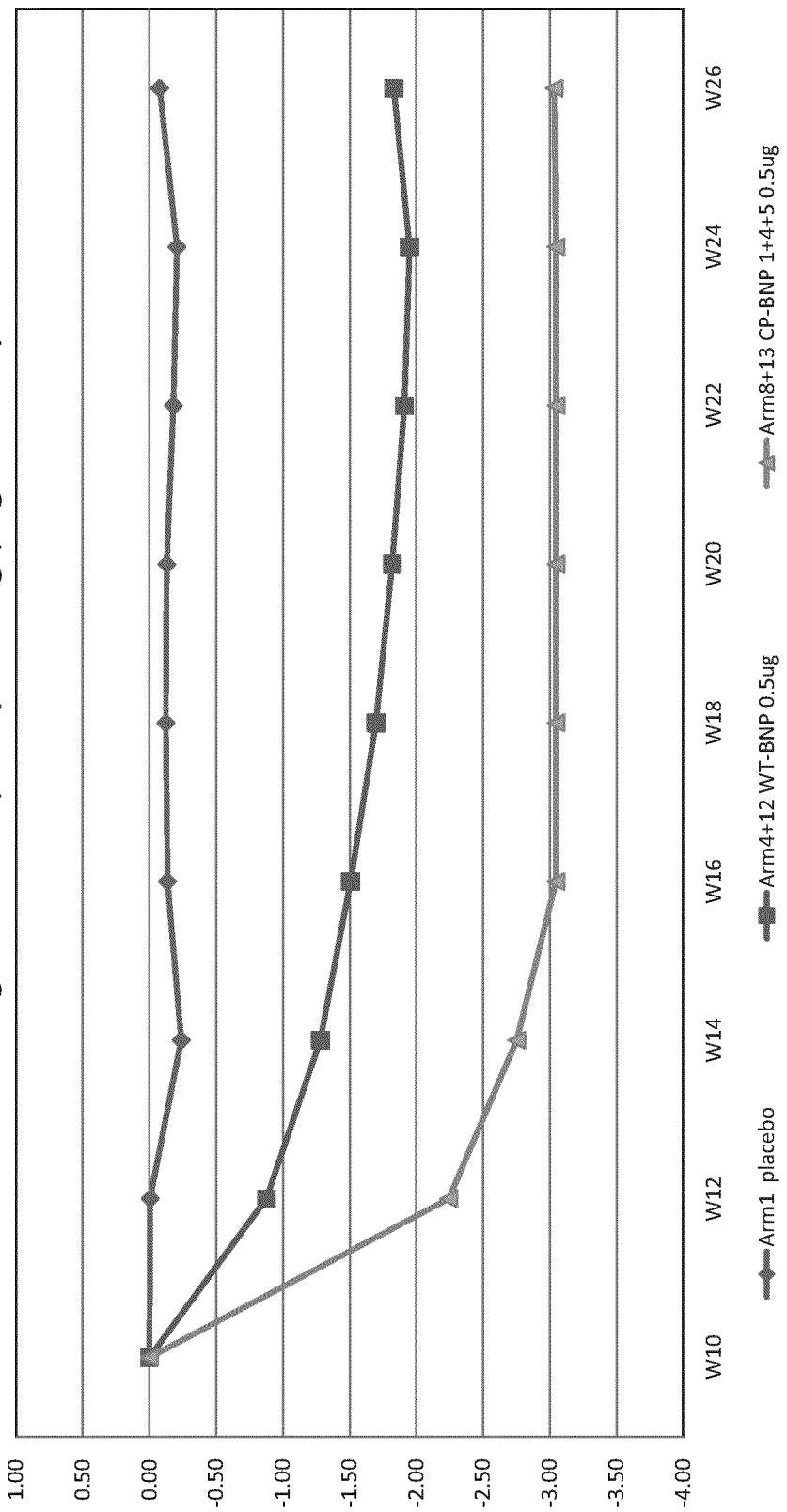

Murine CHB model results—HBsAg levels. The HBsAg level results described below are shown in FIGS. 16A-16C. Placebo (arm 1) did not significantly change HBsAg levels throughout the duration of the study. WT-BNP was dosed at 0.05 (arm 2), 0.1 (arm 3) or 0.5 (arm 4 and 12) μg. The WT-BNP 0.05 μg (arm 2) dose had no effect on HBsAg levels, while the 0.1 (arm 3) or 0.5 (arm 4 and 12) μg doses displayed a dose dependent decrease in HBsAg levels. The combination of CP-BNP 1+4+5 at 0.5 μg (arms 8 and 13) displayed the fastest and steepest decline in HBsAg with sustained effects starting from W12 (two weeks after the first dose) through the end of the study (W26). The greatest decrease was observed with CP-BNP 1+4+5 at 0.5 μg, displaying a 3 log reduction in HBsAg relative to baseline at W10 and also >1 log reduction in HBsAg relative to WT-BNP at the same dose starting from W12 with maximum decreases observed starting at W14. Using doses less than 0.5 μg, CP-BNP 1+4+5 also displayed a dose dependence decrease in HBsAg, but the lower dose of 0.05 μg (arm 6) was similar to WT-BNP at the same dose or 0.1 μg (arm 7) had higher HBsAg relative to the same dose of WT-BNP. Other combinations of CP-BNPs were also tested in this model and found to be less efficacious than CP-BNP 1+4+5. For example, combination of CP-BNP 1+3+4 at 0.5 μg and reduced combinations (CP-BNP 3+4 (arm 9), CP-BNP 4+5 (arm 10), CP-BNP 5+7 (arm 11)) also declined in HBsAg levels, but did so at a slower rate and less absolute decline with >0.5 log reduction achieved starting at W12 and maintained throughout the duration of the study.

The data represented in FIGS. 16A-16C are also shown in tabular format as individual, means, and mean changes from baseline in Tables 10, 11, and 12, respectively.

TABLE 10

Individual HBsAg data.

| | W10 (BL) | W12 | W14 | W16 | W18 | W20 | W22 | W24 | W26 |
|---|---|---|---|---|---|---|---|---|---|
| Arm1 Placebo | 3.04 | 2.96 | 2.18 | 2.50 | 2.53 | 2.57 | 2.56 | 2.35 | 2.60 |
| | 3.35 | 3.17 | 3.09 | 3.18 | 3.13 | 3.18 | 3.08 | 3.03 | 3.14 |
| | 3.23 | 3.26 | 2.95 | 2.95 | 3.09 | 3.12 | 3.11 | 3.17 | 3.20 |
| | 3.19 | 3.09 | 2.99 | 3.06 | 3.06 | 3.04 | 2.96 | 3.02 | 3.12 |
| | 2.72 | 2.94 | 2.78 | 2.92 | 2.99 | 2.87 | 2.95 | 2.93 | 3.08 |
| | 3.45 | 3.53 | 3.57 | 3.55 | 3.45 | 3.43 | 3.26 | 3.26 | 3.39 |
| Arm2 WT BNP 0.05 ug | 2.83 | 2.96 | 2.88 | 2.89 | 2.93 | 3.00 | 2.87 | 2.92 | 2.98 |
| | 2.66 | 2.76 | 2.82 | 2.68 | 2.40 | 2.41 | 2.27 | 2.13 | 2.29 |
| | 2.38 | 2.04 | 1.95 | 1.82 | 1.90 | 1.77 | 1.82 | 1.66 | 1.40 |
| | 3.42 | 3.46 | 3.39 | 3.36 | 3.41 | 3.35 | 3.28 | 3.13 | 3.30 |
| | 3.03 | 3.03 | 2.94 | 3.08 | 3.00 | 2.99 | 2.86 | 2.53 | 1.30 |
| | 3.18 | 3.38 | 3.25 | 3.46 | 3.41 | 3.30 | 3.38 | 3.21 | 3.44 |
| Arm3 WT BNP 0.1 ug | 2.99 | 3.11 | 3.05 | 2.88 | 2.97 | 2.99 | 2.86 | 2.73 | 2.71 |
| | 3.38 | 3.31 | 3.32 | 3.36 | 3.35 | | | | |
| | 1.53 | 2.07 | 2.00 | 1.49 | 1.19 | 1.00 | 0.98 | 2.77 | 0.71 |
| | 2.66 | 0.00 | 0.22 | 0.00 | 0.00 | 0.00 | 0.00 | 0.00 | 0.00 |
| | 2.15 | 0.00 | 0.16 | 0.00 | 0.00 | 0.00 | 0.00 | 0.59 | 0.00 |
| Arm4 WT BNP 0.5 ug | 3.24 | 2.00 | 0.11 | 0.00 | 0.00 | 0.00 | 0.00 | 0.00 | 0.00 |
| | 3.21 | 0.00 | 0.01 | 0.00 | 0.00 | 0.00 | 0.00 | 0.00 | 1.04 |
| | 1.84 | 0.00 | 0.08 | 0.00 | 0.00 | 0.00 | | | |
| | 3.03 | 3.14 | 3.07 | 3.20 | 3.15 | 3.18 | 2.99 | 3.03 | 3.12 |
| | 3.34 | 2.79 | 2.98 | 3.24 | 3.22 | 2.80 | 2.44 | 2.29 | 2.02 |
| | 2.34 | 2.67 | 2.31 | 2.64 | 2.78 | 2.72 | | | |
| Arm5 CP-BNP 1 + 3 + 4 0.5 ug | 3.26 | 2.80 | 2.57 | 1.34 | 0.63 | 0.35 | 0.28 | 0.13 | 0.15 |
| | 1.57 | 1.83 | 1.35 | 0.68 | 0.35 | 0.38 | | | |
| | 3.02 | 2.90 | 2.74 | 2.62 | 2.65 | 2.61 | 2.70 | 2.55 | 2.66 |
| | 2.75 | 2.91 | 2.63 | 0.71 | 0.00 | 0.00 | 0.70 | 0.00 | |
| | 2.66 | 2.52 | 0.00 | 0.00 | 0.00 | 0.00 | 0.00 | 0.00 | |
| | 2.29 | 2.92 | 3.07 | 3.11 | 3.09 | 2.96 | 3.03 | 2.98 | 3.09 |
| | 3.09 | 3.15 | 3.30 | 3.32 | 3.39 | 3.60 | | | |
| Arm6 CP-BNP 1 + 4 + 5 0.05 ug | 3.51 | 3.12 | 3.11 | 3.04 | 3.06 | 3.05 | 3.00 | 3.05 | 3.05 |
| | 3.47 | 3.56 | 3.55 | 3.46 | 3.53 | 3.45 | 3.43 | 3.34 | 3.40 |
| | 3.84 | 3.28 | 3.32 | 3.42 | 3.37 | 3.06 | 3.30 | 3.06 | 3.16 |
| | 2.08 | 2.57 | 2.40 | 2.35 | 1.69 | 0.00 | 0.00 | 1.51 | 0.00 |
| | 3.07 | 2.91 | 2.89 | 2.81 | 2.91 | 2.80 | 2.57 | 1.88 | 1.68 |
| | 3.21 | 3.18 | 3.21 | 3.15 | 3.05 | 3.04 | 3.02 | 2.98 | 2.97 |
| | 3.02 | 3.22 | 3.26 | 3.17 | 3.16 | 3.03 | 3.03 | 3.03 | 3.16 |
| Arm7 CP-BNP 1 + 4 + 5 0.1 ug | 2.32 | 2.57 | 2.64 | 2.69 | 2.71 | 2.60 | 2.62 | 2.61 | 2.59 |
| | 3.14 | 3.11 | 1.90 | 0.45 | 0.06 | 0.00 | 0.00 | 0.62 | 0.00 |
| | 2.30 | 1.69 | 0.10 | 0.00 | 0.00 | 0.00 | 0.00 | 0.00 | 0.00 |
| | 3.89 | 3.50 | 3.41 | 3.42 | 3.32 | 3.18 | 3.28 | 3.15 | 3.00 |
| | 3.28 | 3.34 | 3.37 | 3.31 | 3.31 | 3.34 | 3.33 | 3.39 | 3.47 |
| | 3.30 | 3.11 | 3.21 | 3.13 | 3.11 | 3.18 | 3.14 | 3.22 | 3.29 |
| | 3.42 | 3.39 | 3.29 | 3.41 | 3.46 | 3.34 | 3.18 | 3.17 | 3.23 |
| Arm8 CP-BNP 1 + 4 + 5 0.5 ug | 2.61 | 0.00 | 0.03 | 0.00 | 0.00 | 0.00 | 0.00 | 0.00 | 0.00 |
| | 3.50 | 3.15 | 0.05 | 0.00 | 0.00 | 0.00 | | | |
| | 3.69 | 0.00 | 0.04 | 0.00 | 0.00 | 0.00 | 0.00 | 0.00 | 0.00 |
| | 3.68 | 0.00 | 0.10 | 0.00 | 0.00 | 0.00 | 0.00 | 0.00 | 0.00 |
| | 3.72 | 0.00 | 0.04 | 0.00 | 0.00 | 0.00 | 0.00 | 0.00 | 0.00 |
| | 2.50 | 1.85 | 0.57 | 0.00 | 0.00 | 0.00 | 0.00 | 0.00 | 0.00 |
| | 2.87 | 0.00 | 0.07 | 0.00 | 0.00 | 0.00 | | | |

TABLE 10-continued

Individual HBsAg data.

| | W10 (BL) | W12 | W14 | W16 | W18 | W20 | W22 | W24 | W26 |
|---|---|---|---|---|---|---|---|---|---|
| Arm9 CP-BNP 3 + 4 0.5 ug | 2.27 | 1.67 | 0.22 | 0.00 | 0.00 | 0.00 | 0.00 | 0.00 | 0.00 |
| | 3.17 | 2.93 | 2.98 | 3.12 | 3.06 | 2.80 | 2.79 | 2.80 | 2.74 |
| | 3.61 | 1.78 | 0.75 | 0.47 | 0.22 | 0.17 | 0.06 | 0.38 | 0.07 |
| | 2.80 | 1.00 | 0.26 | 0.00 | 0.00 | 0.00 | 0.00 | 0.00 | 0.00 |
| | 3.04 | 2.63 | 2.78 | 2.67 | 2.77 | 2.71 | 2.54 | 2.68 | 2.79 |
| | 3.10 | 0.00 | 0.10 | 0.00 | 0.00 | 0.00 | 0.00 | 0.00 | 0.00 |
| | 2.51 | 2.71 | 2.45 | 1.91 | 1.45 | 1.16 | 1.08 | 1.06 | 1.05 |
| Arm10 CP-BNP 4 + 5 0.5 ug | 2.62 | 2.52 | 0.62 | 0.00 | 0.00 | 0.00 | 0.00 | 0.00 | 0.00 |
| | 2.78 | 3.06 | 2.87 | 3.10 | 2.92 | 2.90 | 0.00 | 0.00 | 0.00 |
| | 3.36 | 2.94 | 2.68 | 2.54 | −0.06 | 0.00 | 0.00 | 0.00 | 0.00 |
| | 2.34 | 0.00 | 0.08 | 0.00 | 0.00 | 0.00 | 0.00 | 0.00 | 0.00 |
| | 2.94 | 1.44 | −0.03 | 0.00 | 0.00 | 0.00 | 0.00 | 0.00 | 0.00 |
| | 3.17 | 3.23 | 2.96 | 2.90 | 2.83 | 2.72 | 2.50 | 2.73 | 2.82 |
| | 3.14 | 2.81 | 2.54 | 2.54 | 2.35 | 2.23 | 2.36 | 2.22 | 2.60 |
| Arm11 CP-BNP 5 + 7 0.5 ug | 2.82 | 1.21 | 0.44 | 0.08 | 0.00 | 0.00 | 0.00 | 0.00 | 0.00 |
| | 2.46 | 2.53 | 2.52 | 2.56 | 2.28 | 2.00 | 1.84 | 1.99 | 1.92 |
| | 2.93 | 2.55 | 2.36 | 1.75 | 0.00 | 0.00 | 0.00 | 0.00 | 0.00 |
| | 3.44 | 2.87 | 1.26 | 1.94 | 0.00 | 0.00 | 0.00 | 0.00 | 0.03 |
| | 3.30 | 2.75 | 2.84 | 2.95 | 3.00 | 2.89 | 2.78 | 2.93 | 3.29 |
| | 3.03 | 2.82 | 2.87 | 2.18 | 2.19 | 2.12 | 1.56 | 2.02 | 2.05 |
| | 2.18 | 1.71 | 1.48 | 1.42 | 1.37 | 1.21 | 1.09 | 1.26 | 1.41 |
| Arm12 WT-BNP 0.5 ug | 3.04 | 3.13 | 2.75 | 0.00 | 0.00 | 0.00 | | | |
| | 3.31 | 3.22 | 1.94 | 1.68 | 1.50 | 1.48 | | | |
| | 3.01 | 2.95 | 2.94 | 3.23 | 1.18 | 0.00 | 0.00 | 0.00 | 0.00 |
| | 2.98 | 0.00 | 0.16 | 0.00 | 0.00 | 0.00 | 0.00 | 0.00 | 0.00 |
| | 2.56 | 1.68 | 0.35 | 0.00 | 0.00 | 0.00 | 0.00 | 0.00 | 0.00 |
| | 2.99 | 2.80 | 2.81 | 2.82 | 2.71 | 2.87 | 2.55 | 2.34 | 2.44 |
| Arm13 CP-BNP 1 + 4 + 5 0.5 ug | 3.23 | 0.00 | 0.20 | 0.00 | 0.00 | 0.00 | 0.00 | 0.01 | 0.00 |
| | 3.32 | 2.68 | 2.01 | 0.00 | 0.00 | 0.00 | | | |
| | 2.91 | 0.00 | 0.16 | 0.00 | 0.00 | 0.00 | 0.00 | 0.00 | 0.00 |
| | 2.88 | 0.00 | 0.18 | 0.00 | 0.00 | 0.00 | | | |
| | 2.26 | 0.00 | 0.20 | 0.00 | 0.00 | 0.00 | 0.00 | 0.00 | 0.00 |
| | 2.43 | 2.76 | 0.18 | 0.00 | 0.00 | 0.00 | 0.00 | 0.00 | 0.12 |

TABLE 11

Mean HBsAg data.

| Arms | Mean Values | | | | | | | | | | | | | |
|---|---|---|---|---|---|---|---|---|---|---|---|---|---|---|
| | W2 | W4 | W6 | W8 | W10 (BL) | W12 | W14 | W16 | W18 | W20 | W22 | W24 | W26 | |
| Arm1 Placebo | 3.12 | 3.14 | 3.19 | 3.01 | 3.16 | 3.16 | 2.93 | 3.03 | 3.04 | 3.03 | 2.98 | 2.96 | 3.09 | |
| Arm2 WT BNP 0.05 ug | 2.90 | 2.82 | 2.88 | 2.90 | 2.92 | 2.94 | 2.87 | 2.88 | 2.84 | 2.81 | 2.75 | 2.60 | 2.45 | |
| Arm3 WT BNP 0.1 ug | 2.69 | 2.44 | 2.63 | 2.67 | 2.54 | 1.70 | 1.75 | 1.54 | 1.50 | 1.00 | 0.96 | 1.52 | 0.86 | |
| Arm4 + 12 WT BNP 0.5 ug | 2.85 | 2.81 | 2.87 | 2.89 | 2.91 | 2.03 | 1.63 | 1.40 | 1.21 | 1.09 | 1.00 | 0.96 | 1.08 | |
| Arm5 CP-BNP 1 + 3 + 4 0.5 ug | 3.03 | 2.87 | 2.92 | 2.84 | 2.66 | 2.72 | 2.24 | 1.68 | 1.44 | 1.41 | 1.20 | 1.27 | 1.18 | |
| Arm6 CP-BNP 1 + 4 + 5 0.05 ug | 3.06 | 3.10 | 3.09 | 3.12 | 3.17 | 3.12 | 3.11 | 3.06 | 2.97 | 2.63 | 2.62 | 2.69 | 2.49 | |
| Arm7 CP-BNP 1 + 4 + 5 0.1 ug | 3.02 | 2.95 | 3.00 | 3.06 | 3.09 | 2.96 | 2.56 | 2.34 | 2.28 | 2.23 | 2.22 | 2.31 | 2.23 | |
| Arm8 + 13 CP-BNP 1 + 4 + 5 0.5 ug | 2.90 | 2.96 | 2.99 | 2.93 | 3.05 | 0.80 | 0.29 | 0.00 | 0.00 | 0.00 | 0.00 | 0.00 | 0.01 | |
| Arm9 CP-BNP 3 + 4 0.5 ug | 2.74 | 2.71 | 2.70 | 3.00 | 2.93 | 1.82 | 1.36 | 1.17 | 1.07 | 0.98 | 0.92 | 0.99 | 0.95 | |
| Arm10 CP-BNP 4 + 5 0.5 ug | 2.33 | 2.83 | 2.81 | 2.93 | 2.91 | 2.29 | 1.67 | 1.58 | 1.15 | 1.12 | 0.70 | 0.71 | 0.77 | |
| Arm11 CP-BNP 5 + 7 0.5 ug | 2.84 | 2.79 | 2.75 | 2.69 | 2.88 | 2.35 | 1.97 | 1.84 | 1.26 | 1.17 | 1.04 | 1.17 | 1.24 | |

TABLE 12

Mean Changes from Baseline HBsAg data.

| Arms | Mean Changes from Baseline (W10) | | | | | | | | |
|---|---|---|---|---|---|---|---|---|---|
| | W10 (BL) | W12 | W14 | W16 | W18 | W20 | W22 | W24 | W26 |
| Arm1 Placebo | 0.00 | 0.00 | −0.24 | −0.13 | −0.12 | −0.13 | −0.18 | −0.21 | −0.08 |
| Arm2 WT BNP 0.05 ug | 0.00 | 0.02 | −0.04 | −0.04 | −0.08 | −0.11 | −0.17 | −0.32 | −0.47 |
| Arm3 WT BNP 0.1 ug | 0.00 | −0.84 | −0.79 | −1.00 | −1.04 | −1.54 | −1.58 | −1.02 | −1.69 |

TABLE 12-continued

Mean Changes from Baseline HBsAg data.

| Arms | W10 (BL) | W12 | W14 | W16 | W18 | W20 | W22 | W24 | W26 |
|---|---|---|---|---|---|---|---|---|---|
| Arm4 + 12 WT BNP 0.5 ug | 0.00 | −0.88 | −1.28 | −1.51 | −1.70 | −1.82 | −1.91 | −1.95 | −1.83 |
| Arm5 CP-BNP 1 + 3 + 4 0.5 ug | 0.00 | 0.05 | −0.43 | −0.98 | −1.22 | −1.25 | −1.46 | −1.39 | −1.48 |
| Arm6 CP-BNP 1 + 4 + 5 0.05 ug | 0.00 | −0.05 | −0.06 | −0.11 | −0.20 | −0.54 | −0.55 | −0.48 | −0.68 |
| Arm7 CP-BNP 1 + 4 + 5 0.1 ug | 0.00 | −0.14 | −0.53 | −0.75 | −0.81 | −0.86 | −0.87 | −0.78 | −0.87 |
| Arm8 + 13 CP-BNP 1 + 4 + 5 0.5 ug | 0.00 | −2.24 | −2.75 | −3.05 | −3.05 | −3.05 | −3.05 | −3.05 | −3.03 |
| Arm9 CP-BNP 3 + 4 0.5 ug | 0.00 | −1.11 | −1.57 | −1.76 | −1.86 | −1.95 | −2.00 | −1.94 | −1.98 |
| Arm10 CP-BNP 4 + 5 0.5 ug | 0.00 | −0.62 | −1.23 | −1.33 | −1.76 | −1.79 | −2.21 | −2.20 | −2.13 |
| Arm11 CP-BNP 5 + 7 0.5 ug | 0.00 | −0.53 | −0.91 | −1.04 | −1.62 | −1.71 | −1.84 | −1.71 | −1.64 |

The results shown in FIGS. 15A-15C and 16A-16C demonstrate that the CP-BNPs of the present technology are effective at reducing HBV DNA viral load and HBsAg levels in a model of CHB. Accordingly, these results demonstrate that compositions comprising the CP-BNPs of the present technology are useful in methods of treating chronic hepatitis B.

Example 17: Production of Candidate Vaccines from mRNA and Protein Expression Following Transfection of BNP-Encoding Nucleic Acids into Mammalian Cells Production of WT and CP-BNP 4 candidate vaccines from mRNA. pBluescript II SK(+) plasmid containing WT or BNP4 coding sequence was linearized with EcoRV-HF restriction enzyme, purified and confirmed via standard molecular biology techniques. The linearized plasmid was used as a template for mRNA production using an in vitro transcription kit as per the manufacturer's recommendations (Life Technologies), then purified (Life Technologies, Thermo Fisher). The resulting transcripts were stored at −80° C. until ready for use. Transfections were performed using Lipofectamine MessengerMAX reagent (ThermoFisher) into HEK293T or Huh7 cells for 5 days. Then, media was collected and processed using sucrose ultracentrifugation method described above. Alternatively, cell lysates were processed using NP-40 lysis buffer and cell debris pelleted. Samples were assessed by western blot as previously described.

Figure 17A:
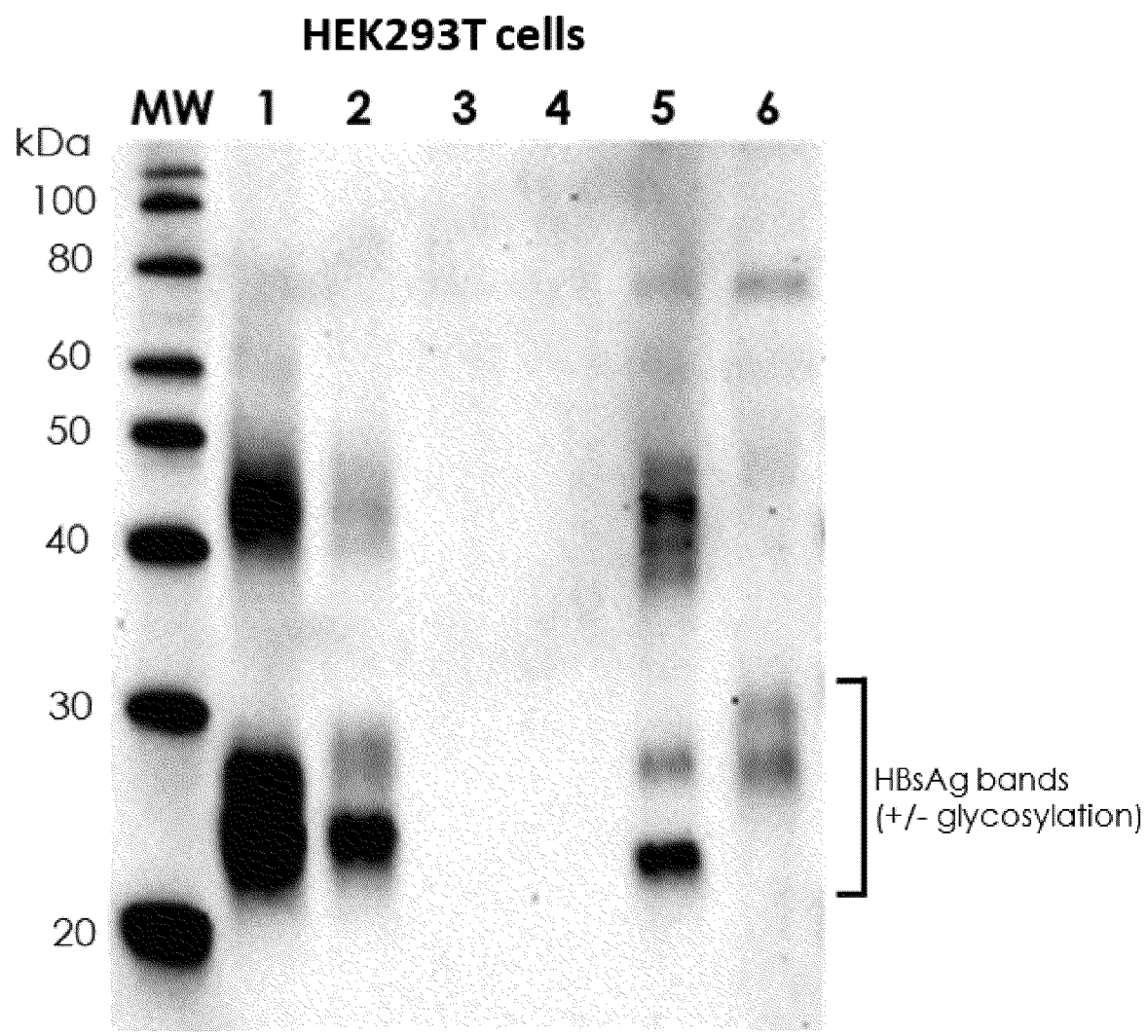
FIGS. 17A-17B are images showing Western analysis of HBsAg BNP expression of WT-BNP and CP-BNP 4 from RNA after in vitro transcription and transfection into HEK293T (FIG. 17A) and Huh7 (FIG. 17B) cell lines. Using an anti-HBsAg antibody, HBsAg bands (+/−glycosylation, ~50%) were detected in both WT-BNP (24 or 27 kDa) and CP-BNP 4 (29 or 32 kDa), produced after transfection of the appropriate mRNAs into both cell lines. Untreated and reagent assay control transfections were negative for HBsAg. Controls included purified HBsAg (with Flag tag, 25 or 28 kD) and samples from after transfection of WT-BNP DNA (with flag tag, 25 or 28 kD). The mRNA transcripts encode WT-BNP or BNP4-specific HBsAg subunits in the absence of a Flag tag.
Figure 17B:
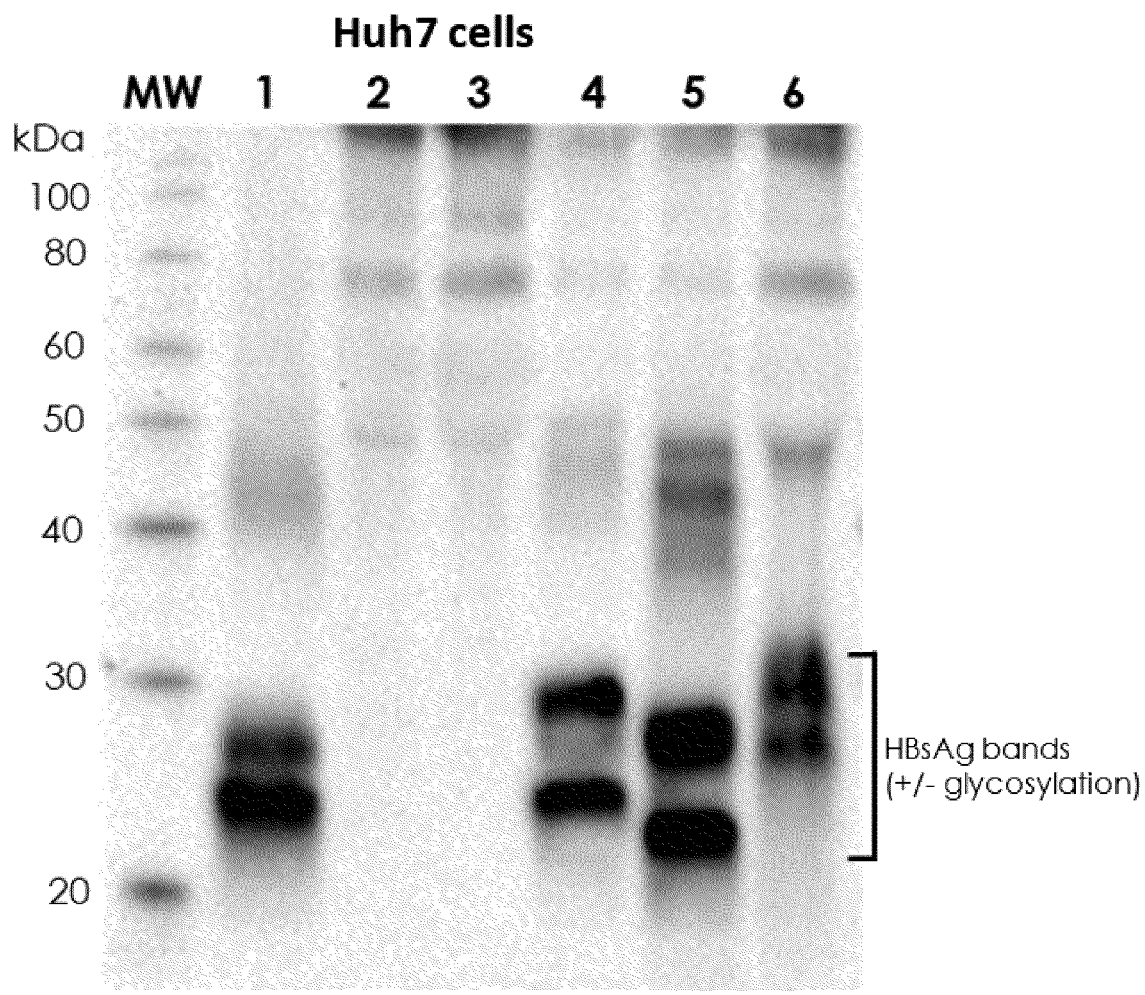

Protein expression results following transfection of BNP-encoding nucleic acids (mRNA and DNA) into mammalian cell lines. HBsAg BNP expression from transfection of mRNA was successfully achieved in two different cell lines (HEK293T and Huh7) as measured by Western blot analysis using an anti-HBsAg antibody (FIGS. 17A-17B). The Western blot identified multiple bands, including expected size of the monomer (WT-BNP, 24 kD; CP-BNP 4, 29 kD) and glycosylated variants (WT-BNP, 27 kD; CP-BNP 4, 32 kD). In addition, HBsAg was detected after transfection with a DNA construct that would express WT-BNP (with flag tag 15 and 28 kDa).

These results demonstrate that mRNA constructs of the present technology are capable of expressing functional HBsAg-S subunits, as demonstrated by their ability to secrete into the cell culture supernant, which is an indication for BNP formation. CP-BNPs of the present technology, generated by RNA transfection, could be useful in compositions for the treatment of chronic hepatitis B.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a nonlimiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

REFERENCES

WHO Fact sheet 18 Jul. 2018
Nayagam et al. (2016) *Lancet Infectious Dis* 2016 16:1399-1408
Block et al. (2013) *Antiviral Res.* 98(1):27-34
Cheong W S et al. Chimeric virus-like particles for the delivery of an inserted conserved influenzy A-specific CTL epitope. 2009 *Antiviral Res* 81(2):113-122.
Chothia et al. (1987) *J. Mol. Biol.* 196:901
Coligan et al. *Current Protocols in Immunology,* 1991-1997
Gefter et al. (1977) *Somatic Cell Genet.* 3:231-236
Huang L R et al. An immunocompetent mouse model for the tolerance of human chronic hepatitis B virus infection. 2006 *PNAS* 103(47):17862-17867
Hyakumura M. et al. Modification of asparagine-linked glycan density for the design of hepatitis V virus virus-like particles with enhanced immunogenicity. 2015 *J Virol* 89(22): 11312-11322
Jones et al. (1986) *Nature* 321:522-525
Kim and Ahituv. The hydrodynamic tail vein assay as a tool for the study of liver promoters and enhancers. 2013 *Methods Mol Biol;* 1015:279-289
Kohler et al. (1975) *Nature* 256:495-499
Kohler et al. (1976) *Eur. J. Immunol.* 6(7):511-519
Kozbor et al. (1986) *Methods in Enzymology* 121:140
Lim et al. (2014) *Hepatology* 60 (1) *supplement:* 1623, 980A
Liu et al. (1987) *Proc. Natl. Acad. Sci. USA* 84:3439-3443
Longo P A et al. Transient mammalian cell transfection with polylethylenimine (PEI). 2013 *Methods Enzymol* 529:227-240
Patzer E J et al. Cell culture derived recombinant HBsAg is highly immunogenic and protects chimpanzees from infection with hepatitis B virus. 1986 *Nature Biotechnol* 4:630-636
qHBsAg Elecsys from Roche Diagnostics. Immunoassay for the qualitative determination of hepatitis B surface antigen (HBsAg) (diagnostics.roche.com)
Richmann et al. (1988) *Nature* 332:323-327
Shulman et al. (1978) *Nature* 276:269-270
Sitnik R. et al. A real-time quantitative assay for hepatitis B DNA virus (HBV) developed to detect all HBV genotypes. 2010 *Rev Inst Med Trop Sao Paulo* 52(3): 119-124
Toyama et al. (1987) *Monoclonal Antibody, Experiment Manual,* published by Kodansha Scientific
Trowbridge (1982) *J. Exp. Med.* 148(1):220-227
Verhoeyen et al. (1988) *Science* 239:1534-1536
Volk et al. (1982) *J. Virol.* 42(1):220-227
Volz et al. (2015) *International Meeting, Molecular Biology of Hepatitis B virus, Session IX: Antiviral therapy,* 0-205, Germany
Yang P L et al. Hydrodynamic injection of viral DNA: A mouse model of acute hepatitis B virus infection. 2002 *PNAS* 99(21):13825-13830

SEQUENCE LISTING

```
Sequence total quantity: 55
SEQ ID NO: 1            moltype = AA  length = 275
FEATURE                 Location/Qualifiers
REGION                  1..275
                        note = Description of Artificial Sequence: Synthetic
                         polypeptide
source                  1..275
                        mol_type = protein
                        organism = synthetic construct
SEQUENCE: 1
MDYKDDDDKE NITSGFLGPL LVLQAGFFLL TRILTIPQSL DSWWTSLNFL GGTTVCLGQN  60
SQSPTSNHSP TSCPPTCPGY RWMCLRRFII FLFILLLCLI FLLVLLDYQG MLPVCPLIPG  120
SSTTSTGPCR TCMTTGSGSP CKTCTTPGSG SPCKTCTTPG SGSPCKTCTT PGSGSTGQGT  180
SMYPSCCCTK PSDGNCTCIP IPSSWAFGKF LWEWASARFS WLSLLVPFVQ WFVGLSPTVW  240
LSVIWMMWYW GPSLYSILSP FLPLLPIFFC LWVYI                            275

SEQ ID NO: 2            moltype = AA  length = 275
FEATURE                 Location/Qualifiers
REGION                  1..275
                        note = Description of Artificial Sequence: Synthetic
                         polypeptide
source                  1..275
                        mol_type = protein
                        organism = synthetic construct
SEQUENCE: 2
MDYKDDDDKE NITSGFLGPL LVLQAGFFLL TRILTIPQSL DSWWTSLNFL GGTTVCLGQN  60
SQSPTSNHSP TSCPPTCPGY RWMCLRRFII FLFILLLCLI FLLVLLDYQG MLPVCPLIPG  120
SSTTSTGPCR TCMTTGSGSP CRTCTTPGSG SPCRTCTTPG SGSPCRTCTT PGSGSTGQGT  180
SMYPSCCCTK PSDGNCTCIP IPSSWAFGKF LWEWASARFS WLSLLVPFVQ WFVGLSPTVW  240
LSVIWMMWYW GPSLYSILSP FLPLLPIFFC LWVYI                            275

SEQ ID NO: 3            moltype = AA  length = 278
FEATURE                 Location/Qualifiers
REGION                  1..278
                        note = Description of Artificial Sequence: Synthetic
                         polypeptide
source                  1..278
                        mol_type = protein
                        organism = synthetic construct
SEQUENCE: 3
MDYKDDDDKE NITSGFLGPL LVLQAGFFLL TRILTIPQSL DSWWTSLNFL GGTTVCLGQN  60
```

```
SQSPTSNHSP TSCPPTCPGY RWMCLRRFII FLFILLLCLI FLLVLLDYQG MLPVCPLIPG    120
SSTTSTGPCR TCMTTGSGSC TKPTDGNCGS GSCTKPTDGN CGSGSCTKPT DGNCGSGSTG    180
QGTSMYPSCC CTKPSDGNCT CIPIPSSWAF GKFLWEWASA RFSWLSLLVP FVQWFVGLSP    240
TVWLSVIWMM WYWGPSLYSI LSPFLPLLPI FFCLWVYI                            278

SEQ ID NO: 4           moltype = AA  length = 279
FEATURE                Location/Qualifiers
REGION                 1..279
                       note = Description of Artificial Sequence: Synthetic
                        polypeptide
source                 1..279
                       mol_type = protein
                       organism = synthetic construct
SEQUENCE: 4
MDYKDDDDKE NITSGFLGPL LVLQAGFFLL TRILTIPQSL DSWWTSLNFL GGTTVCLGQN     60
SQSPTSNHSP TSCPPTCPGY RWMCLRRFII FLFILLLCLI FLLVLLDYQG MLPVCPLIPG    120
SSTTSTGPCR TCMTTGSGSC KTCTTPAQGN SMFPSGSGSC KTCTTPAQGN SMFPSGSGST    180
GQGTSMYPSC CCTKPSDGNC TCIPIPSSWA FGKFLWEWAS ARFSWLSLLV PFVQWFVGLS    240
PTVWLSVIWM MWYWGPSLYS ILSPFLPLLP IFFCLWVYI                           279

SEQ ID NO: 5           moltype = AA  length = 260
FEATURE                Location/Qualifiers
REGION                 1..260
                       note = Description of Artificial Sequence: Synthetic
                        polypeptide
source                 1..260
                       mol_type = protein
                       organism = synthetic construct
SEQUENCE: 5
MDYKDDDDKE NITSGFLGPL LVLQAGFFLL TRILTIPQSL DSWWTSLNFL GGTTVCLGQN     60
SQSPTSNHSP TSCPPTCPGY RWMCLRRFII FLFILLLCLI FLLVLLDYQG MLPVCPLIPG    120
SSTTSTGPCK TCMTTGQGTS MYPSCCCTKP SDGNCGSGSC TKPTDGNCGS GSCTKPTDGN    180
CTCIPIPSSW AFGKFLWEWA SARFSWLSLL VPFVQWFVGL SPTVWLSVIW MMWYWGPSLY    240
SILSPFLPLL PIFFCLWVYI                                                260

SEQ ID NO: 6           moltype = AA  length = 284
FEATURE                Location/Qualifiers
REGION                 1..284
                       note = Description of Artificial Sequence: Synthetic
                        polypeptide
source                 1..284
                       mol_type = protein
                       organism = synthetic construct
SEQUENCE: 6
MDYKDDDDKE NITSGFLGPL LVLQAGFFLL TRILTIPQSL DSWWTSLNFL GGTTVCLGQN     60
SQSPTSNHSP TSCPPTCPGY RWMCLRRFII FLFILLLCLI FLLVLLDYQG MLPVCPLIPG    120
SSTTSTGPCR TCTTPGSGSP CKTCTTPGSG SPCRTCMTTA QGTSMYPSCC CTKPSDGNCG    180
SGSCTKPTDG NCGSGSCTKP TDGNCTCIPI PSSWAFGKFL WEWASARFSW LSLLVPFVQW    240
FVGLSPTVWL SVIWMMWYWG PSLYSILSPF LPLLPIFFCL WVYI                     284

SEQ ID NO: 7           moltype = AA  length = 277
FEATURE                Location/Qualifiers
REGION                 1..277
                       note = Description of Artificial Sequence: Synthetic
                        polypeptide
source                 1..277
                       mol_type = protein
                       organism = synthetic construct
SEQUENCE: 7
MDYKDDDDKE NITSGFLGPL LVLQAGFFLL TRILTIPQSL DSWWTSLNFL GGTTVCLGQN     60
SQSPTSNHSP TSCPPTCPGY RWMCLRRFII FLFILLLCLI FLLVLLDYQG MLPVCPLIPG    120
SSTTSTGPCK TCTTPAQGNS MFPSCGSGSC KTCTTPAQGN SMFPSCGSGS PCRTCMTTAQ    180
GTSMYPSCCC TKPSDGNCTC IPIPSSWAFG KFLWEWASAR FSWLSLLVPF VQWFVGLSPT    240
VWLSVIWMMW YWGPSLYSIL SPFLPLLPIF FCLWVYI                             277

SEQ ID NO: 8           moltype = AA  length = 266
FEATURE                Location/Qualifiers
REGION                 1..266
                       note = Description of Artificial Sequence: Synthetic
                        polypeptide
source                 1..266
                       mol_type = protein
                       organism = synthetic construct
SEQUENCE: 8
MDYKDDDDKE NITSGFLGPL LVLQAGFFLL TRILTIPQSL DSWWTSLNFL GGTTVCLGQN     60
SQSPTSNHSP TSCPPTCPGY RWMCLRRFII FLFILLLCLI FLLVLLDYQG MLPVCPLIPG    120
SSTTSTGPCR TCMTTAQGTS MYPSCCCTKP SDGNCGSGSP CKTCTTPAQG NSMFPSCCCT    180
KPTDGNCTCI PIPSSWAFGK FLWEWASARF SWLSLLVPFV QWFVGLSPTV WLSVIWMMWY    240
WGPSLYSILS PFLPLLPIFF CLWVYI                                         266
```

| SEQ ID NO: 9 | moltype = DNA  length = 846 |
|---|---|
| FEATURE | Location/Qualifiers |
| misc_feature | 1..846 |
| | note = Description of Artificial Sequence: Synthetic polynucleotide |
| source | 1..846 |
| | mol_type = other DNA |
| | organism = synthetic construct |

SEQUENCE: 9

```
gagctcgcca ccatggacta taaagacgac gatgacaaag agaacatcac atcaggattc    60
ctaggacccc ttctcgtgtt acaggcgggg ttttcttgt tgacaagaat cctcacaata   120
ccgcagagtc tagactcgtg gtggacttct ctcaattttc taggggggaac taccgtgtgt   180
cttggccaaa attcgcagtc cccaacctcc aatcactcac caacctcttg tcctccaact   240
tgtcctggtt atcgctggat gtgtctgcgg cgtttatca tcttcctctt catcctgctg   300
ctatgcctca tcttcttgtt ggttcttctg gactatcaag gtatgttgcc cgtttgtcct   360
ctaattccag gatcctcaac aaccagcacg ggaccatgcc ggacctgcat gactaccggt   420
tccggttcac cctgcaaaac ctgtactacc ccaggttcgt gatcaccctg caaaacctgt   480
actaccccag gttccggatc accctgcaaa acctgtacta ccccaggttc cggatcaacc   540
ggtcaaggaa cctctatgta tccctcctgt tgctgtacca aaccttcgga cggaaattgc   600
acctgtattc ccatcccatc atcctgggct ttcgaaaat tccatgggga gtgggcctca   660
gcccgtttct cctggctcag tttactagtg ccatttgttc agtggttcgt agggctttcc   720
cccactgttt ggctttcagt tatatggatg atgtggtatt gggggccaag tctgtacagc   780
atcttgagtc ccttttttacc gctgttacca attttctttt gtctttgggt atacatttaa   840
ctcgag                                                               846
```

| SEQ ID NO: 10 | moltype = DNA  length = 846 |
|---|---|
| FEATURE | Location/Qualifiers |
| misc_feature | 1..846 |
| | note = Description of Artificial Sequence: Synthetic polynucleotide |
| source | 1..846 |
| | mol_type = other DNA |
| | organism = synthetic construct |

SEQUENCE: 10

```
gagctcgcca ccatggacta taaagacgac gatgacaaag agaacatcac atcaggattc    60
ctaggacccc ttctcgtgtt acaggcgggg ttttcttgt tgacaagaat cctcacaata   120
ccgcagagtc tagactcgtg gtggacttct ctcaattttc taggggggaac taccgtgtgt   180
cttggccaaa attcgcagtc cccaacctcc aatcactcac caacctcttg tcctccaact   240
tgtcctggtt atcgctggat gtgtctgcgg cgtttatca tcttcctctt catcctgctg   300
ctatgcctca tcttcttgtt ggttcttctg gactatcaag gtatgttgcc cgtttgtcct   360
ctaattccag gatcctcaac aaccagcacg ggaccatgcc ggacctgcat gactaccggt   420
tccggttcac cctgcgggac ctgtactacc ccaggttcgt gatcaccctg ccggacctgt   480
actaccccag gttccggatc accctgccgg acctgtacta ccccaggttc cggatcaacc   540
ggtcaaggaa cctctatgta tccctcctgt tgctgtacca aaccttcgga cggaaattgc   600
acctgtattc ccatcccatc atcctgggct ttcgaaaat tccatgggga gtgggcctca   660
gcccgtttct cctggctcag tttactagtg ccatttgttc agtggttcgt agggctttcc   720
cccactgttt ggctttcagt tatatggatg atgtggtatt gggggccaag tctgtacagc   780
atcttgagtc ccttttttacc gctgttacca attttctttt gtctttgggt atacatttaa   840
ctcgag                                                               846
```

| SEQ ID NO: 11 | moltype = DNA  length = 855 |
|---|---|
| FEATURE | Location/Qualifiers |
| misc_feature | 1..855 |
| | note = Description of Artificial Sequence: Synthetic polynucleotide |
| source | 1..855 |
| | mol_type = other DNA |
| | organism = synthetic construct |

SEQUENCE: 11

```
gagctcgcca ccatggacta taaagacgac gatgacaaag agaacatcac atcaggattc    60
ctaggacccc ttctcgtgtt acaggcgggg ttttcttgt tgacaagaat cctcacaata   120
ccgcagagtc tagactcgtg gtggacttct ctcaattttc taggggggaac taccgtgtgt   180
cttggccaaa attcgcagtc cccaacctcc aatcactcac caacctcttg tcctccaact   240
tgtcctggtt atcgctggat gtgtctgcgg cgtttatca tcttcctctt catcctgctg   300
ctatgcctca tcttcttgtt ggttcttctg gactatcaag gtatgttgcc cgtttgtcct   360
ctaattccag gatcctcaac aaccagcacg ggaccatgcc ggacctgcat gactaccggt   420
tccggttcat gtactaaacc aaccgacgga aattgcggtt ccggttcatg tactaaacca   480
accgacggaa attgcggttc cggttcatgt actaaaccaa ccgacggaaa ttgcggttcc   540
ggttcaaccg gtcaaggaac ctctatgtat ccctcctgtt gctgtaccaa accttcggac   600
ggaaattgca cctgtattcc catcccatca tcctgggctt tcgaaaatt cctatggag   660
tgggcctcag cccgtttctc ctggctcagt ttactagtgc catttgttca gtggttcgta   720
gggctttccc ccactgtttg gctttcagtt atatggatga tgtggtattg ggggccaagt   780
ctgtacagca tcttgagtcc cttttttaccg ctgttaccaa ttttctttg tctttggta   840
tacatttaac tcgag                                                    855
```

| SEQ ID NO: 12 | moltype = DNA  length = 858 |
|---|---|
| FEATURE | Location/Qualifiers |
| misc_feature | 1..858 |

```
                        note = Description of Artificial Sequence: Synthetic
                              polynucleotide
source                  1..858
                        mol_type = other DNA
                        organism = synthetic construct
SEQUENCE: 12
gagctcgcca ccatggacta taaagacgac gatgacaaag agaacatcac atcaggattc   60
ctaggacccc ttctcgtgtt acaggcgggg ttttttcttgt tgacaagaat cctcacaata  120
ccgcagagtc tagactcgtg gtggacttct ctcaattttc taggggggaac taccgtgtgt  180
cttggccaaa attcgcagtc cccaacctcc aatcactcac caacctcttg tcctccaact   240
tgtcctggtt atcgctggat gtgtctgcgg cgtttttatca tcttcctctt catcctgctg  300
ctatgcctca tcttcttgtt ggttcttctg gactatcaag gtatgttgcc cgtttgtcct   360
ctaattccag gatcctcaac aaccagcacg ggaccatgcc ggacctgcat gactaccggt   420
tccggttcat gtaaaacttg cactacccca gctcaaggaa attctatgtt cccttccggt   480
tccggatcat gtaaaacttg cactacccca gctcaaggaa attctatgtt cccttccggt   540
tccggatcaa ccggtcaagg aacctctatg tatcccctcct gttgctgtac caaaccttcg   600
gacggaaatt gcacctgtat tcccatccca tcatcctggg ctttcggaaa attcctatgg  660
gagtgggcct cagcccgttt ctcctggctc agtttactag tgccatttgt tcagtggttc   720
gtagggcttt cccccactgt ttggctttca gttatatgga tgatgtggta ttggggggcca   780
agtctgtaca gcatcttgag tcccttttta ccgctgttac caattttctt ttgtctttgg   840
gtatacattt aactcgag                                                858

SEQ ID NO: 13             moltype = DNA  length = 801
FEATURE                   Location/Qualifiers
misc_feature              1..801
                          note = Description of Artificial Sequence: Synthetic
                                polynucleotide
source                    1..801
                          mol_type = other DNA
                          organism = synthetic construct
SEQUENCE: 13
gagctcgcca ccatggacta taaagacgac gatgacaaag agaacatcac atcaggattc   60
ctaggacccc ttctcgtgtt acaggcgggg ttttttcttgt tgacaagaat cctcacaata  120
ccgcagagtc tagactcgtg gtggacttct ctcaattttc taggggggaac taccgtgtgt  180
cttggccaaa attcgcagtc cccaacctcc aatcactcac caacctcttg tcctccaact   240
tgtcctggtt atcgctggat gtgtctgcgg cgtttttatca tcttcctctt catcctgctg  300
ctatgcctca tcttcttgtt ggttcttctg gactatcaag gtatgttgcc cgtttgtcct   360
ctaattccag gatcctcaac aaccagcacg ggaccatgcc ggacctgcat gactaccggt   420
caaggaacct ctatgtatcc ctcctgttgc tgtaccaaac cttcggacgg aaattgcggt   480
tccggttcat gtactaaacc aaccgacgga aattgcggtt ccggttcatg tactaaacca   540
accgacggaa attgcacctg tattcccatc ccatcatcct gggctttcgg aaaattccta   600
tgggagtggg cctcagcccg tttctcctgg ctcagtttac tagtgccatt tgttcagtgg  660
ttcgtagggc tttcccccac tgtttggctt tcagttatat ggatgatgtg gtattggggg   720
ccaagtctgt acagcatctt gagtcccttt ttaccgctgt taccaatttt cttttgtctt   780
tgggtataca tttaactcga g                                            801

SEQ ID NO: 14             moltype = DNA  length = 873
FEATURE                   Location/Qualifiers
misc_feature              1..873
                          note = Description of Artificial Sequence: Synthetic
                                polynucleotide
source                    1..873
                          mol_type = other DNA
                          organism = synthetic construct
SEQUENCE: 14
gagctcgcca ccatggacta taaagacgac gatgacaaag agaacatcac atcaggattc   60
ctaggacccc ttctcgtgtt acaggcgggg ttttttcttgt tgacaagaat cctcacaata  120
ccgcagagtc tagactcgtg gtggacttct ctcaattttc taggggggaac taccgtgtgt  180
cttggccaaa attcgcagtc cccaacctcc aatcactcac caacctcttg tcctccaact   240
tgtcctggtt atcgctggat gtgtctgcgg cgttttatca tcttcctctt catcctgctg   300
ctatgcctca tcttcttgtt ggttcttctg gactatcaag gtatgttgcc cgtttgtcct   360
ctaattccag gatcctcaac aaccagcacg ggaccatgca aaacctgtac taccccaggt   420
tccggatcac catgcaaaac ctgtactacc ccaggttccg gatcaccatg ccggacctgc   480
atgactactg ctcaaggaac ctctatgtat ccctcctgtt gctgtaccaa accttcggac   540
ggaaattgcg gttccggttc atgtactaaa ccaaccgacg gaaattgcgg ttccggttca   600
tgtactaaac caaccgacgg aaattgcacc tgtattccca tccatcatc tgggctttc   660
ggaaaattcc tatgggagtg ggcctcagcc cgtttctcct ggctcagttt actagtgcca   720
tttgttcagt ggttcgtagg gctttccccc actgtttggc tttcagttat atggatgatg   780
tggtattggg ggccaagtct gtacagcatc ttgagtccct tttaccgct gttaccaatt   840
ttcttttgtc tttgggtata catttaactc gag                               873

SEQ ID NO: 15             moltype = DNA  length = 852
FEATURE                   Location/Qualifiers
misc_feature              1..852
                          note = Description of Artificial Sequence: Synthetic
                                polynucleotide
source                    1..852
                          mol_type = other DNA
                          organism = synthetic construct
```

```
SEQUENCE: 15
gagctcgcca ccatggacta taaagacgac gatgacaaag agaacatcac atcaggattc    60
ctaggacccc ttctcgtgtt acaggcgggg ttttcttgt tgacaagaat cctcacaata   120
ccgcagagtc tagactcgtg gtggacttct ctcaatttc tagggggaac taccgtgtgt   180
cttggccaaa attcgcagtc cccaacctcc aatcactcac caacctcttg tcctccaact   240
tgtcctggtt atcgctggat gtgtctgcgg cgtttatca tcttcctctt catcctgctg   300
ctatgcctca tcttcttgtt ggttcttctg gactatcaag gtatgttgcc cgtttgtcct   360
ctaattccag gatcctcaac aaccagcacg ggaccatgca aaacctgcac cactccagcg   420
caaggaaatt ctatgtttcc ctcctgtggt tccggttcat gcaaaacctg caccactgt   480
gcgcaaggaa attctatgtt tccctcctgt ggttccggtt caccatgccg gacctgcatg   540
actactgctc aaggaacctc tatgtatccc tcctgttgct gtaccaaacc ttcggacgga   600
aattgcacct gtattccat cccatcatcc tgggctttcg gaaaattcct atgggagtgg   660
gcctcagccc gtttctcctg gctcagttta ctagtgccat tgttcagtg gttcgtaggg   720
cttttccccca ctgtttggct ttcagttata tggatgatgt ggtattgggg gccaagtctg   780
tacagcatct tgagtccctt tttaccgctg ttaccaattt tcttttgtct ttgggtatac   840
atttaactcg ag                                                       852

SEQ ID NO: 16           moltype = DNA   length = 819
FEATURE                 Location/Qualifiers
misc_feature            1..819
                        note = Description of Artificial Sequence: Synthetic
                         polynucleotide
source                  1..819
                        mol_type = other DNA
                        organism = synthetic construct
SEQUENCE: 16
gagctcgcca ccatggacta taaagacgac gatgacaaag agaacatcac atcaggattc    60
ctaggacccc ttctcgtgtt acaggcgggg ttttcttgt tgacaagaat cctcacaata   120
ccgcagagtc tagactcgtg gtggacttct ctcaatttc tagggggaac taccgtgtgt   180
cttggccaaa attcgcagtc cccaacctcc aatcactcac caacctcttg tcctccaact   240
tgtcctggtt atcgctggat gtgtctgcgg cgtttatca tcttcctctt catcctgctg   300
ctatgcctca tcttcttgtt ggttcttctg gactatcaag gtatgttgcc cgtttgtcct   360
ctaattccag gatcctcaac aaccagcacg ggaccatgcc ggacctgcat gactactgct   420
caaggaacct ctatgtatcc ctcctgttgc tgtaccaaac cttcggacgg aaattgcggt   480
tccggttcac catgcaaaac ctgtactacc ccagcgcaag gaaattctat gtttccctcc   540
tgctgttgca ctaaaccaac cgacggaaat tgcacctgta ttcccatccc atcatcctgg   600
gctttcggaa aattcctatg ggagtgggcc tcagcccgtt tctcctggct cagtttacta   660
gtgccatttg ttcagtggtt cgtagggctt tcccccactg tttggctttc agttatatgg   720
atgatgtggt attgggggcc aagtctgtac agcatcttga gtcccttttt accgctgtta   780
ccaattttct tttgtctttg ggtatacatt taactcgag                          819

SEQ ID NO: 17           moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 17
TCTTPAQGNS MFPSC                                                     15

SEQ ID NO: 18           moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 18
TCTIPAQGTS MFPSC                                                     15

SEQ ID NO: 19           moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 19
TCTTPAQGTS MFPSC                                                     15

SEQ ID NO: 20           moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 20
```

```
CTKPTDGNCT                                                                    10

SEQ ID NO: 22          moltype = AA  length = 10
FEATURE                Location/Qualifiers
REGION                 1..10
                       note = Description of Artificial Sequence: Synthetic peptide
source                 1..10
                       mol_type = protein
                       organism = synthetic construct
SEQUENCE: 21
CTKPSDGNCT                                                                    10

SEQ ID NO: 22          moltype = DNA  length = 681
FEATURE                Location/Qualifiers
misc_feature           1..681
                       note = Description of Artificial Sequence: Synthetic
                       polynucleotide
source                 1..681
                       mol_type = other DNA
                       organism = synthetic construct
SEQUENCE: 22
atggagaaca tcacatcagg attcctagga ccccttctcg tgttacaggc ggggttttc    60
ttgttgacaa gaatcctcac aataccgcag agtctagact cgtggtggac ttctctcaat   120
ttttcagggg gaactaccgt gtgtcttggc caaaattcgc agtccccaac ctccaatcac   180
tcaccaacct cttgtcctcc aacttgtcct ggttatcgct ggatgtgtct gcggcgtttt   240
atcatcttcc tcttcatcct gctgctatgc ctcatcttct tgttggttat tctggactat   300
caaggtatgt tgcccgtttg tcctctaatt ccaggatcct caacaaccag cacgggacca   360
tgccggacct gcatgactac cggtcaagga acctctatgt atccctg ttgctgtacc      420
aaaccttcgg acgaaattg cacctgtatt cccatccat catcctggc tttcggaaaa      480
ttcctatggg agtgggcctc agcccgtttc tcctggctca gttactggat gccatttgtt   540
cagtggttcg tagggctttc ccccactgtt tggcttttcag ttatatggat gatgtggtat   600
tggggggccaa gtctgtacag catcttgagt cccttttac cgctgttacc aattttcttt   660
tgtctttggg tatacattta a                                             681

SEQ ID NO: 23          moltype = DNA  length = 705
FEATURE                Location/Qualifiers
misc_feature           1..705
                       note = Description of Artificial Sequence: Synthetic
                       polynucleotide
source                 1..705
                       mol_type = other DNA
                       organism = synthetic construct
SEQUENCE: 23
atggactata aagacgacga tgacaaagag aacatcacat caggattcct aggaccccctt   60
ctcgtgttac aggcggggtt tttcttgttg acaagaatcc tcacaatacc gcagagtcta   120
gactcgtggt ggacttctct caattttcta ggggaactac cgtgtgtct tggccaaaat    180
tcgcagtccc caacctccaa tcactcacca acctcttgtc ctccaacttg tcctggttat   240
cgctggatgt gtctgcggcg ttttatcatc ttcctcttca tcctgctgct atgcctcatc   300
ttcttgttgg ttcttctgga ctatcaaggt atgttgcccg tttgtcctct aattccagga   360
tcctcaacaa ccagcacggg accatgccgg acctgcatga ctaccggtca aggaacctct   420
atgtatccct cctgttgctg taccaaaacct tcggacacctg attgcacctg tattcccatc   480
ccatcatcct gggctttcgg aaaattccta tgggagtggg cctcagcccg tttctcctgg   540
ctcagtttac tagtgccatt tgttcagtgg ttcgtagggc tttccccac tgtttggctt    600
tcagttatat ggatgatgtg gtattggggg ccaagtctgt acagcatctt gagtcccttt   660
taccgctgtt accaattttt cttttgtctt tgggtataca tttaa                   705

SEQ ID NO: 24          moltype = AA  length = 16
FEATURE                Location/Qualifiers
REGION                 1..16
                       note = Description of Artificial Sequence: Synthetic peptide
MOD_RES                2
                       note = Lys or Arg
MOD_RES                5
                       note = Thr or Met
MOD_RES                6
                       note = Thr or Ile
MOD_RES                7
                       note = Pro, Thr or Leu
MOD_RES                8
                       note = Ala or Val
MOD_RES                11
                       note = Asn or Thr
MOD_RES                14
                       note = Phe or Tyr
source                 1..16
                       mol_type = protein
                       organism = synthetic construct
SEQUENCE: 24
CXTCXXXXQG XSMXPC                                                     16
```

```
SEQ ID NO: 25          moltype = AA  length = 8
FEATURE                Location/Qualifiers
REGION                 1..8
                       note = Description of Artificial Sequence: Synthetic peptide
MOD_RES                3
                       note = Lys or Arg
MOD_RES                6
                       note = Thr or Met
MOD_RES                7
                       note = Thr, Ile, Ser, or Ala
MOD_RES                8
                       note = Pro, Thr or Leu
source                 1..8
                       mol_type = protein
                       organism = synthetic construct
SEQUENCE: 25
PCXTCXXX                                                                         8

SEQ ID NO: 26          moltype = AA  length = 12
FEATURE                Location/Qualifiers
REGION                 1..12
                       note = Description of Artificial Sequence: Synthetic peptide
MOD_RES                7
                       note = Thr or Ser
MOD_RES                12
                       note = Thr or Ser
source                 1..12
                       mol_type = protein
                       organism = synthetic construct
SEQUENCE: 26
CCCTKPXDGN CX                                                                    12

SEQ ID NO: 27          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 27
CKTCTTPAQG NSMFPSC                                                               17

SEQ ID NO: 28          moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 28
PCKTCTTP                                                                         8

SEQ ID NO: 29          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 29
CCCTKPTDGN CT                                                                    12

SEQ ID NO: 30          moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 30
CKTCTIPAQG TSMFPSC                                                               17

SEQ ID NO: 31          moltype = AA  length = 11
FEATURE                Location/Qualifiers
REGION                 1..11
                       note = Description of Artificial Sequence: Synthetic peptide
source                 1..11
                       mol_type = protein
```

```
                         organism = synthetic construct
SEQUENCE: 31
CCTKPSDGNC T                                                              11

SEQ ID NO: 32            moltype = AA   length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 32
CRTCTTPAQG TSMFPSC                                                        17

SEQ ID NO: 33            moltype = AA   length = 8
FEATURE                  Location/Qualifiers
REGION                   1..8
                         note = Description of Artificial Sequence: Synthetic peptide
source                   1..8
                         mol_type = protein
                         organism = synthetic construct
SEQUENCE: 33
PCRTCTTP                                                                   8

SEQ ID NO: 34            moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 34
CTKPTDGNC                                                                  9

SEQ ID NO: 35            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 35
CKTCTTPAQG NSMFPS                                                         16

SEQ ID NO: 36            moltype = AA   length = 10
FEATURE                  Location/Qualifiers
REGION                   1..10
                         note = Description of Artificial Sequence: Synthetic peptide
MOD_RES                  5
                         note = Thr or Ser
source                   1..10
                         mol_type = protein
                         organism = synthetic construct
SEQUENCE: 36
CTKPXTDGNC                                                                10

SEQ ID NO: 37            moltype = AA   length = 8
FEATURE                  Location/Qualifiers
REGION                   1..8
                         note = Description of Artificial Sequence: Synthetic peptide
MOD_RES                  3
                         note = Lys or Arg
MOD_RES                  6
                         note = Thr or Met
source                   1..8
                         mol_type = protein
                         organism = synthetic construct
SEQUENCE: 37
PCXTCXTP                                                                   8

SEQ ID NO: 38            moltype = AA   length = 16
FEATURE                  Location/Qualifiers
REGION                   1..16
                         note = Description of Artificial Sequence: Synthetic peptide
MOD_RES                  2
                         note = Lys or Arg
MOD_RES                  5
                         note = Thr or Met
MOD_RES                  7
```

```
                        note = Pro or Thr
MOD_RES                 11
                        note = Asn or Thr
MOD_RES                 14
                        note = Phe or Tyr
source                  1..16
                        mol_type = protein
                        organism = synthetic construct
SEQUENCE: 38
CXTCXTXAQG XSMXPS                                                           16

SEQ ID NO: 39           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 39
PCRTCMTTAQ GTSMYPSCCC TKPSDGNC                                              28

SEQ ID NO: 40           moltype = AA  length = 28
FEATURE                 Location/Qualifiers
REGION                  1..28
                        note = Description of Artificial Sequence: Synthetic peptide
source                  1..28
                        mol_type = protein
                        organism = synthetic construct
SEQUENCE: 40
PCKTCTTPAQ GNSMFPSCCC TKPTDGNC                                              28

SEQ ID NO: 41           moltype = AA  length = 46
FEATURE                 Location/Qualifiers
REGION                  1..46
                        note = Description of Artificial Sequence: Synthetic
                         polypeptide
source                  1..46
                        mol_type = protein
                        organism = synthetic construct
SEQUENCE: 41
MTTGSGSPCK TCTTPGSGSP CKTCTTPGSG SPCKTCTTPG SGSTGQ                           46

SEQ ID NO: 42           moltype = AA  length = 46
FEATURE                 Location/Qualifiers
REGION                  1..46
                        note = Description of Artificial Sequence: Synthetic
                         polypeptide
source                  1..46
                        mol_type = protein
                        organism = synthetic construct
SEQUENCE: 42
MTTGSGSPCR TCTTPGSGSP CRTCTTPGSG SPCRTCTTPG SGSTGQ                           46

SEQ ID NO: 43           moltype = AA  length = 49
FEATURE                 Location/Qualifiers
REGION                  1..49
                        note = Description of Artificial Sequence: Synthetic
                         polypeptide
source                  1..49
                        mol_type = protein
                        organism = synthetic construct
SEQUENCE: 43
MTTGSGSCTK PTDGNCGSGS CTKPTDGNCG SGSCTKPTDG NCGSGSTGQ                        49

SEQ ID NO: 44           moltype = AA  length = 49
FEATURE                 Location/Qualifiers
REGION                  1..49
                        note = Description of Artificial Sequence: Synthetic
                         polypeptide
source                  1..49
                        mol_type = protein
                        organism = synthetic construct
SEQUENCE: 44
MTTGSGSCKT CTTPAQGNSM FPSGSGSCKT CTTPAQGNSM FPSGSGSTG                        49

SEQ ID NO: 45           moltype = AA  length = 41
FEATURE                 Location/Qualifiers
REGION                  1..41
                        note = Description of Artificial Sequence: Synthetic
```

```
                              polypeptide
source                        1..41
                              mol_type = protein
                              organism = synthetic construct
SEQUENCE: 45
CCCTKPSDGN CGSGSCTKPT DGNCGSGSCT KPTDGNCTCI P                    41

SEQ ID NO: 46           moltype = AA  length = 39
FEATURE                 Location/Qualifiers
REGION                  1..39
                        note = Description of Artificial Sequence: Synthetic
                         polypeptide
source                  1..39
                        mol_type = protein
                        organism = synthetic construct
SEQUENCE: 46
STGPCKTCTT PGSGSPCKTC TTPGSGSPCR TCMTTAQGT                       39

SEQ ID NO: 47           moltype = AA  length = 41
FEATURE                 Location/Qualifiers
REGION                  1..41
                        note = Description of Artificial Sequence: Synthetic
                         polypeptide
source                  1..41
                        mol_type = protein
                        organism = synthetic construct
SEQUENCE: 47
SCCCTKPSDG NCGSGSCTKP TDGNCGSGSC TKPTDGNCTC I                    41

SEQ ID NO: 48           moltype = AA  length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 48
PCRTCMTTAQ GTSMYPS                                               17

SEQ ID NO: 49           moltype = AA  length = 66
FEATURE                 Location/Qualifiers
REGION                  1..66
                        note = Description of Artificial Sequence: Synthetic
                         polypeptide
source                  1..66
                        mol_type = protein
                        organism = synthetic construct
SEQUENCE: 49
TGPCKTCTTP AQGNSMFPSC GSGSCKTCTT PAQGNSMFPS CGSGSPCRTC MTTAQGTSMY 60
PSCCCT                                                           66

SEQ ID NO: 50           moltype = AA  length = 226
FEATURE                 Location/Qualifiers
REGION                  1..226
                        note = Description of Artificial Sequence: Synthetic
                         polypeptide
source                  1..226
                        mol_type = protein
                        organism = synthetic construct
SEQUENCE: 50
MENITSGFLG PLLVLQAGFF LLTRILTIPQ SLDSWWTSLN FLGGTTVCLG QNSQSPTSNH 60
SPTSCPPTCP GYRWMCLRRF IIFLFILLLC LIFLLVLLDY QGMLPVCPLI PGSSTTSTGP 120
CRTCMTTGQG TSMYPSCCCT KPSDGNCTCI PIPSSWAFGK FLWEWASARF SWLSLLVPFV 180
QWFVGLSPTV WLSVIWMMWY WGPSLYSILS PFLPLLPIFF CLWVYI              226

SEQ ID NO: 51           moltype = AA  length = 234
FEATURE                 Location/Qualifiers
REGION                  1..234
                        note = Description of Artificial Sequence: Synthetic
                         polypeptide
source                  1..234
                        mol_type = protein
                        organism = synthetic construct
SEQUENCE: 51
MDYKDDDDKE NITSGFLGPL LVLQAGFFLL TRILTIPQSL DSWWTSLNFL GGTTVCLGQN 60
SQSPTSNHSP TSCPPTCPGY RWMCLRRFII FLFILLLCLI FLLVLLDYQG MLPVCPLIPG 120
SSTTSTGPCR TCMTTGQGTS MYPSCCCTKP SDGNCTCIPI PSSWAFGKFL WEWASARFSW 180
LSLLVPFVQW FVGLSPTVWL SVIWMMWYWG PSLYSILSPF LPLLPIFFCL WVYI     234
```

```
SEQ ID NO: 52          moltype = AA   length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 52
CKTCTTPAQG NSMFPS                                                             16

SEQ ID NO: 53          moltype = AA   length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 53
GSGS                                                                           4

SEQ ID NO: 54          moltype = AA   length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 54
CTKPSDGNC                                                                      9

SEQ ID NO: 55          moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 55
PCRTCMTT                                                                       8
```

What is claimed is:

1. A bio-nanoparticle (BNP) comprising a hepadnaviral envelope HBsAg-S fusion protein comprising one or more antigenic epitope repeat regions, wherein said one or more antigenic epitope repeat regions are expressed in the Loop 1 and Loop 2 regions of HBsAg-S domain, and are selected from the group consisting of:
   (1) antigenic epitope repeat regions expressed in Loop 1 and defined by (a) the amino acid sequence $CX_1TCX_2X_3X_4X_5QGX_6SMX-PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or (b) the amino acid sequence $PCX:TCX_9X_{10}X_{11}$ (SEQ ID NO: 25), wherein $X_8$ is K or R, $X_9$ is T or M, $X_{10}$ is T, I or S, and $X_{11}$ is P, T or L;
   (2) antigenic epitope repeat regions expressed in Loop 2 and defined by the amino acid sequence $CCCTKPX_{12}DGNCX_{13}$ (SEQ ID NO: 26), wherein $X_{12}$ is T or S; and $X_{13}$ is T or S; and
   (3) antigenic epitope repeat regions consisting of the amino acid sequence PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKPSDGNC (SEQ ID NO: 54), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), or PCKTCTTPAQGNSMFPSCCCTKPTDGNC (SEQ ID NO: 40).

2. A method of treating hepatitis B infection in a subject in need thereof, comprising administering to the subject a bio-nanoparticle (BNP) comprising a hepadnaviral envelope HBsAg-S fusion protein comprising one or more antigenic epitope repeat regions, wherein said one or more antigenic epitope repeat regions are expressed in the Loop 1 and Loop 2 regions of HBsAg-S domain, and are selected from the group consisting of:
   (1) antigenic epitope repeat regions expressed in Loop 1 and defined by (a) the amino acid sequence $CX_1TCX_2X_3X_4X_5QGX_6SMX-PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or (b) the amino acid sequence $PCX:TCX_9X_{10}X_{11}$ (SEQ ID NO: 25), wherein $X_8$ is K or R, $X_9$ is T or M, $X_{10}$ is T, I or S, and $X_{11}$ is P, T or L;
   (2) antigenic epitope repeat regions expressed in Loop 2 and defined by the amino acid sequence $CCCTKPX_{12}DGNCX_{13}$ (SEQ ID NO: 26), wherein $X_{12}$ is T or S; and $X_{13}$ is T or S; and
   (3) antigenic epitope repeat regions consisting of the amino acid sequence PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKPSDGNC (SEQ ID NO: 54), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), or PCKTCTTPAQGNSMFPSCCCTKPTDGNC (SEQ ID NO: 40).

3. A method for inducing an immune response against hepatitis B virus in a subject comprising administering to the subject a bio-nanoparticle (BNP) comprising a hepadnaviral envelope HBsAg-S fusion protein comprising one or more antigenic epitope repeat regions, wherein said one or more antigenic epitope repeat regions are selected from the group consisting of:
- (1) antigenic epitope repeat regions expressed in Loop 1 and defined by (a) the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or (b) the amino acid sequence $PCX_8TCX_9X_{10}X_{11}$ (SEQ ID NO: 25), wherein $X_8$ is K or R, $X_9$ is T or M, $X_{10}$ is T, I or S, and $X_{11}$ is P, T or L;
- (2) antigenic epitope repeat regions expressed in Loop 2 and defined by the amino acid sequence $CCCTKPX_{12}DGNCX_{13}$ (SEQ ID NO: 26), wherein $X_{12}$ is T or S; and $X_{13}$ is T or S; and
- (3) antigenic epitope repeat regions consisting of the amino acid sequence PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKPSDGNC (SEQ ID NO: 54), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), or PCKTCTTPAQGNSMFPSCCCTKPTDGNC (SEQ ID NO: 40).

4. The method of claim 3, wherein the hepadnaviral envelope fusion protein comprises a spacer domain between the antigenic epitope repeat regions and the envelope protein.

5. A kit for treating hepatitis B infection in a subject in need thereof comprising a bio-nanoparticle (BNP), wherein the BNP comprises a hepadnaviral envelope HBsAg-S fusion protein comprising one or more antigenic epitope repeat regions, wherein said antigenic epitope repeat regions are selected from the group consisting of:
- (1) antigenic epitope repeat regions expressed in Loop 1 and defined by (a) the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or (b) the amino acid sequence $PCX_8TCX_9X_{10}X_{11}$ (SEQ ID NO: 25), wherein $X_8$ is K or R, $X_9$ is T or M, $X_{10}$ is T, I or S, and Xu is P, T or L;
- (2) antigenic epitope repeat regions expressed in Loop 2 and defined by the amino acid sequence $CCCTKPX_{12}DGNCX_{13}$ (SEQ ID NO: 26), wherein $X_{12}$ is T or S; and $X_{13}$ is T or S; and
- (3) antigenic epitope repeat regions consisting of the amino acid sequence PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKPSDGNC (SEQ ID NO: 54), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), or PCKTCTTPAQGNSMFPSCCCTKPTDGNC (SEQ ID NO: 40).

6. The kit according to claim 5, wherein the hepadnaviral envelope fusion protein comprises a spacer domain between the antigenic epitope repeat regions and the envelope protein.

7. A recombinant mRNA encoding a hepadnaviral envelope HBsAg-S fusion protein comprising one or more antigenic epitope repeat regions, wherein said antigenic epitope repeat regions are selected from the group consisting of:
- (1) antigenic epitope repeat regions expressed in Loop 1 and defined by (a) the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or (b) the amino acid sequence $PCX_8TCX_9X_{10}X_{11}$ (SEQ ID NO: 25), wherein $X_8$ is K or R, $X_9$ is T or M, $X_{10}$ is T, I or S, and $X_{11}$ is P, T or L;
- (2) antigenic epitope repeat regions expressed in Loop 2 and defined by the amino acid sequence $CCCTKPX_{12}DGNCX_{13}$ (SEQ ID NO: 26), wherein $X_{12}$ is T or S; and $X_{13}$ is T or S; and
- (3) antigenic epitope repeat regions consisting of the amino acid sequence PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKPSDGNC (SEQ ID NO: 54), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), or PCKTCTTPAQGNSMFPSCCCTKPTDGNC (SEQ ID NO: 40).

8. The recombinant mRNA of claim 7, wherein the modified hepadnaviral envelope fusion protein comprises a spacer domain between the antigenic epitope repeat regions and the envelope protein.

9. An expression vector comprising the recombinant mRNA of claim 7.

10. A composition comprising the recombinant mRNA of claim 7 and a pharmaceutically acceptable carrier.

11. A method of treating hepatitis B infection in a subject in need thereof, comprising administering to the subject a recombinant mRNA encoding a hepadnaviral envelope HBsAg-S fusion protein comprising one or more antigenic epitope repeat regions, wherein said antigenic epitope repeat regions are selected from the group consisting of:
- (1) antigenic epitope repeat regions expressed in Loop 1 and defined by (a) the amino acid sequence $CX_1TCX_2X_3X_4X_5QGX_6SMX_7PC$ (SEQ ID NO: 24), wherein $X_1$ is K or R, $X_2$ is T or M, $X_3$ is T or I, $X_4$ is P T or L, $X_5$ is A or V, $X_6$ is N or T, and $X_7$ is F or Y; or (b) the amino acid sequence $PCX_8TCX_9X_{10}X_{11}$ (SEQ ID NO: 25), wherein $X_8$ is K or R, $X_9$ is T or M, $X_{10}$ is T, I or S, and $X_{11}$ is P, T or L;
- (2) antigenic epitope repeat regions expressed in Loop 2 and defined by the amino acid sequence $CCCTKPX_{12}DGNCX_{13}$ (SEQ ID NO: 26), wherein $X_{12}$ is T or S; and $X_{13}$ is T or S; and
- (3) antigenic epitope repeat regions consisting of the amino acid sequence PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKPSDGNC (SEQ ID NO: 54), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), or PCKTCTTPAQGNSMFPSCCCTKPTDGNC (SEQ ID NO: 40).

12. A method for inducing an immune response against hepatitis B virus in a subject comprising administering to the subject a recombinant mRNA encoding modified hepadnaviral envelope HBsAg-S fusion protein comprising one or more antigenic epitope repeat regions, wherein said antigenic epitope repeat regions are selected from the group consisting of:
- (1) antigenic epitope repeat regions expressed in Loop 1 and defined by (a) the amino acid sequence CX₁TCX₂X₃X₄X₅QGX₆SMX₇PC (SEQ ID NO: 24), wherein X₁ is K or R, X₂ is T or M, X₃ is T or I, X₄ is P T or L, X₅ is A or V, X₆ is N or T, and X₇ is F or Y; or (b) the amino acid sequence PCX₈TCX₉X₁₀X₁₁ (SEQ ID NO: 25), wherein X₈ is K or R, X₉ is T or M, X₁₀ is T, I or S, and X₁₁ is P, T or L;

(2) antigenic epitope repeat regions expressed in Loop 2 and defined by the amino acid sequence CCCTKPX₁₂DGNCX₁₃ (SEQ ID NO: 26), wherein X₁₂ is T or S; and X₁₃ is T or S; and (3) antigenic epitope repeat regions consisting of the amino acid sequence PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKPSDGNC (SEQ ID NO: 54), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), or PCKTCTTPAQGNSMFPSCCCTKPTDGNC (SEQ ID NO: 40).

13. A kit for treating hepatitis B infection in a subject in need thereof comprising a recombinant mRNA, wherein the recombinant mRNA encodes a hepadnaviral envelope HBsAg-S fusion protein comprising one or more antigenic epitope repeat regions, wherein said antigenic epitope repeat regions are selected from the group consisting of:

(1) antigenic epitope repeat regions expressed in Loop 1 and defined by (a) the amino acid sequence CX₁TCX₂X₃X₄X₅QGX₆SMX-PC (SEQ ID NO: 24), wherein X₁ is K or R, X₂ is T or M, X₃ is T or I, X₄ is P T or L, X₅ is A or V, X₆ is N or T, and X₇ is F or Y; or (b) the amino acid sequence PCX:TCX₉X₁₀X₁₁ (SEQ ID NO: 25), wherein X₈ is K or R, X₉ is T or M, X₁₀ is T, I or S, and X₁₁ is P, T or L;

(2) antigenic epitope repeat regions expressed in Loop 2 and defined by the amino acid sequence CCCTKPX₁₂DGNCX₁₃ (SEQ ID NO: 26), wherein X₁₂ is T or S; and X₁₃ is T or S; and (3) antigenic epitope repeat regions consisting of the amino acid sequence PCKTCTTP (SEQ ID NO: 28), PCRTCTTP (SEQ ID NO: 33), CTKPTDGNC (SEQ ID NO: 34), CKTCTTPAQGNSMFPS (SEQ ID NO: 35), CTKPSDGNC (SEQ ID NO: 54), PC(K/R)TC(T/M)TP (SEQ ID NO: 37), C(K/R)TC(T/M)T(P/T)AQG(N/T)SM(F/Y)PS (SEQ ID NO: 38), PCRTCMTTAQGTSMYPSCCCTKPSDGNC (SEQ ID NO: 39), or PCKTCTTPAQGNSMFPSCCCTKPTDGNC (SEQ ID NO: 40).

14. A composition comprising one or more peptides selected from the group consisting of TCTTPAQGNSMFPSC (SEQ ID NO: 17), TCTIPAQGTSMFPSC (SEQ ID NO: 18), TCTTPAQGTSMFPSC (SEQ ID NO: 19), CTKPTDGNCT (SEQ ID NO: 20), and CTKPSDGNCT (SEQ ID NO: 21).

15. The composition of claim 14, wherein the one or more peptides is conjugated to a carrier protein.

16. The composition of claim 15, wherein the carrier protein is keyhole limpet hemocyanin (KLH).

17. The composition of claim 16 further comprising a pharmaceutically acceptable carrier.

18. A method of treating hepatitis B infection in a subject in need thereof, comprising administering to the subject one or more peptides selected from the group consisting of TCTTPAQGNSMFPSC (SEQ ID NO: 17), TCTIPAQGTSMFPSC (SEQ ID NO: 18), TCTTPAQGTSMFPSC (SEQ ID NO: 19), CTKPTDGNCT (SEQ ID NO: 20), and CTKPSDGNCT (SEQ ID NO: 21).

19. The method of claim 18, wherein the one or more peptides is conjugated to a carrier protein.

20. The method of claim 19, wherein the carrier protein is keyhole limpet hemocyanin (KLH).

21. A bio-nanoparticle (BNP) comprising a hepadnaviral envelope HBsAg-S fusion protein comprising an HBsAg-S template comprising the amino acids set forth in SEQ ID NO: 50 and an epitope insert consisting of the amino acids set forth SEQ ID NO: 44, wherein the epitope insert replaces amino acid residues 125-128 of SEQ ID NO: 50.

22. A bio-nanoparticle (BNP) comprising a hepadnaviral envelope HBsAg-S fusion protein comprising an HBsAg-S template comprising the amino acids set forth in SEQ ID NO: 50 and an epitope insert consisting of the amino acids set forth in SEQ ID NO: 45, wherein the epitope insert replaces residues 137-151 of SEQ ID NO: 50.

23. A bio-nanoparticle (BNP) comprising a hepadnaviral envelope HBsAg-S fusion protein comprising one or more antigenic epitope regions selected from the group consisting of: CTKPTDGNC (SEQ ID NO: 34), CTKPSDGNC (SEQ ID NO: 54), and CKTCTTPAQGNSMFPS (SEQ ID NO: 35).

24. The BNP of claim 23, wherein the one or more antigenic epitope regions comprise CKTCTTPAQGNSMFPS (SEQ ID NO: 35).

25. The BNP of claim 24, wherein the one or more antigenic epitope regions comprise a first region comprising CKTCTTPAQGNSMFPS (SEQ ID NO: 35) and a second region comprising CKTCTTPAQGNSMFPS (SEQ ID NO: 35), wherein the first region and the second region are connected by a GSGS linker (SEQ ID NO: 53).

26. The BNP of claim 23, wherein the one or more antigenic epitope regions are selected from the group consisting of CTKPTDGNC (SEQ ID NO: 34) and CTKPSDGNC (SEQ ID NO: 54).

27. The BNP of claim 26, wherein the one or more antigenic epitope regions comprise a first region comprising CTKPSDGNC (SEQ ID NO: 54), a second region comprising CTKPTDGNC (SEQ ID NO: 34), and a third region comprising CTKPTDGNC (SEQ ID NO: 34), wherein the first region and the second region are connected by a GSGS linker (SEQ ID NO: 53) and the second and third region are connected by a GSGS linker (SEQ ID NO: 53).

28. A composition comprising a first bio-nanoparticle (BNP) and a second bio-nanoparticle (BNP);
wherein the first BNP comprises a hepadnaviral envelope HBsAg-S fusion protein comprising a first and a second antigenic epitope region comprising CKTCTTPAQGNSMFPS (SEQ ID NO: 35); and
wherein the second BNP comprises a hepadnaviral envelope HBsAg-S fusion protein comprising a first, a second, and a third antigenic epitope region, wherein the first antigenic epitope region comprises CTKPSDGNC (SEQ ID NO: 54) and the second and third antigenic epitope regions comprise CTKPTDGNC (SEQ ID NO: 34).

29. A composition comprising a bio-nanoparticle (BNP) wherein the BNP comprises a hepadnaviral envelope HBsAg-S fusion protein comprising a first and a second antigenic epitope region comprising CKTCTTPAQGNSMFPS (SEQ ID NO: 35).

30. A composition comprising a bio-nanoparticle (BNP); wherein the BNP comprises a hepadnaviral envelope HBsAg-S fusion protein comprising a first, a second, and a third antigenic epitope region, wherein the first antigenic epitope region comprises CTKPSDGNC (SEQ ID NO: 54) and the second and third antigenic epitope regions comprise CTKPTDGNC (SEQ ID NO: 34).

31. The composition of claim 28 for use in a method for treating or preventing hepatitis B infection.

* * * * *